US012350317B2

(12) United States Patent
Elson et al.

(10) Patent No.: US 12,350,317 B2
(45) Date of Patent: Jul. 8, 2025

(54) IMMUNOTHERAPY FOR THE TREATMENT AND PREVENTION OF INFLAMMATORY BOWEL DISEASE

(71) Applicant: THE UAB RESEARCH FOUNDATION, Birmingham, AL (US)

(72) Inventors: Charles O. Elson, Birmingham, AL (US); Wayne Duck, Pell City, AL (US); Qing Zhao, Birmingham, AL (US); Katie Alexander, Homewood, AL (US)

(73) Assignee: THE UAB RESEARCH FOUNDATION, Birmingham, AL (US)

( * ) Notice: Subject to any disclaimer, the term of this patent is extended or adjusted under 35 U.S.C. 154(b) by 881 days.

(21) Appl. No.: 17/426,234

(22) PCT Filed: Feb. 7, 2020

(86) PCT No.: PCT/US2020/017319

§ 371 (c)(1),
(2) Date: Jul. 28, 2021

(87) PCT Pub. No.: WO2020/163782

PCT Pub. Date: Aug. 13, 2020

(65) Prior Publication Data

US 2022/0088145 A1 Mar. 24, 2022

Related U.S. Application Data

(60) Provisional application No. 62/802,873, filed on Feb. 8, 2019.

(51) Int. Cl.

| | |
|---|---|
| ***A61K 38/20*** | (2006.01) |
| ***A61K 31/436*** | (2006.01) |
| ***A61K 38/16*** | (2006.01) |
| ***A61K 45/06*** | (2006.01) |
| ***A61P 29/00*** | (2006.01) |

(52) U.S. Cl.

CPC ........ *A61K 38/2013* (2013.01); *A61K 31/436* (2013.01); *A61K 38/164* (2013.01); *A61K 45/06* (2013.01); *A61P 29/00* (2018.01)

(58) Field of Classification Search

None

See application file for complete search history.

(56) References Cited

U.S. PATENT DOCUMENTS

| | | | |
|---|---|---|---|
| 7,105,653 | B2 | 9/2006 | Shanafelt et al. |
| 9,428,567 | B2 | 8/2016 | Garcia et al. |
| 9,580,486 | B2 | 2/2017 | Gavin et al. |
| 9,616,105 | B2 | 4/2017 | Paulsen et al. |
| 10,174,091 | B1 | 1/2019 | Higginson-Scott et al. |
| 10,174,092 | B1 | 1/2019 | Higginson-Scott et al. |
| 2015/0374788 | A1 | 12/2015 | Paulsen et al. |

OTHER PUBLICATIONS

Devos et al., (Proteins: Structure, Function and Genetics, 2000, vol. 41: 98-107).*

Whisstock et al., (Quarterly Reviews of Biophysics 2003, vol. 36 (3): 307-340,).*

Witowski et al., (Biochemistry 38:11643-11650, 1999).*

Kisselev L., (Structure, 2002, vol. 10: 8-9).*

Alexander, et al., CBirTox is a Selective Antigen-Specific Agonist of the Treg-Iga-Microbiota Homeostatic Pathway, Plos One, vol. 12, No. 7, Jul. 27, 2017, 20 pages.

Aichele et al., Peptide-Induced T-Cell Tolerance to Prevent Autoimmune Diabetes in a Transgenic Mouse Model, Immunology, Proceedings of the National Academy of Sciences of the United States of America (PNAS), vol. 91, Jan. 1994, pp. 444-448.

Aichele et al., T Cell Priming Versus T Cell Tolerance Induced by Synthetic Peptides, Journal of Experimental Medicine, vol. 182, Jul. 1995, pp. 261-266.

Araki et al., mTOR Regulates Memory CD8 T Cell Differentiation, Nature, vol. 460, No. 7251, Jul. 2, 2009, pp. 108-112.

Araki et al., The Role of mTOR in Memory CD8+ T-Cell Differentiation, Immunological Reviews, vol. 235, No. 1, May 2010, pp. 234-243.

Bacher et al., Regulatory T Cell Specificity Directs Tolerance Versus Allergy Against Aeroantigens in Humans, Cell, vol. 167, Nov. 3, 2016, pp. 1067-1078.

Basset et al., Cholera-like Enterotoxins and Regulatory T Cells, Toxins, vol. 2, No. 7, Jul. 2010, pp. 1774-1795.

Battaglia et al., Rapamycin Selectively Expands CD4+CD25+ FoxP3+ Regulatory T Cells, Blood, vol. 105, No. 12, Jun. 15, 2005, pp. 4743-4748.

Belkaid et al., Regulatory T Cells in the Control of Host-Microorganism Interactions*, Annual Review of Immunology, vol. 27, No. 1, Feb. 2009, pp. 551-589.

Burton et al., Sequential Transcriptional Changes Dictate Safe and Effective Antigen-Specific Immunotherapy, Nature Communications, vol. 5, No. 4741, Sep. 3, 2014, 13 pages.

Boyman, et al., The Role of Interleukin-2 During Homeostasis and Activation of the Immune System, Nature Reviews Immunology, vol. 12, No. 3, Mar. 1, 2012, pp. 180-190.

Campbell et al., Peptide Immunotherapy in Allergic Asthma Generates IL-10-Dependent Immunological Tolerance Associated with Linked Epitope Suppression, Journal of Experimental Medicine, vol. 206, No. 7, Jul. 6, 2009, pp. 1535-1547.

Carbone et al., Immunological Risk Factors for Infection After Immunosuppressive and Biologic Therapies, Expert Review of Anti-infective Therapy, vol. 9, Jan. 10, 2014, pp. 405-413.

Chang et al., Emerging Concepts in Immunotherapy—T Cell Metabolism as a Therapeutic Target, Nature Immunology, vol. 17, No. 4, Apr. 2016, pp. 364-368.

(Continued)

*Primary Examiner* — Jennifer E Graser

(74) *Attorney, Agent, or Firm* — Kilpatrick Townsend & Stockton LLP

(57) ABSTRACT

Provided herein are methods and compositions for treating and preventing inflammatory bowel disease.

14 Claims, 41 Drawing Sheets

Specification includes a Sequence Listing.

(56) References Cited

OTHER PUBLICATIONS

Chang et al., Posttranscriptional Control of T Cell Effector Function by Aerobic Glycolysis, Cell, vol. 153, Jun. 6, 2013, pp. 1239-1251.
Chen et al., Conversion of Peripheral CD4+CD25− Naive T Cells to CD4+CD25+ Regulatory T Cells by TGF-Beta Induction of Transcription Factor Foxp3, The Journal of Experimental Medicine, vol. 198, No. 12, Dec. 15, 2003, pp. 1875-1886.
Cong et al., A Dominant, Coordinated T Regulatory Cell-IgA Response to the Intestinal Microbiota, Proceedings of the National Academy of Sciences of the United States of America (PNAS), vol. 106, No. 46, Nov. 17, 2009, pp. 19256-19261.
Cook et al., Analysis of Flagellin-Specific Adaptive Immunity Reveals Links to Dysbiosis in Patients with Inflammatory Bowel Disease, Cellular and Molecular Gastroenterology and Hepatology, vol. 9, No. 3, Nov. 2019, pp. 485-506.
Corthay, How do Regulatory T Cells Work? Scandinavian Journal of Immunology, vol. 70, No. 4, Oct. 2009, pp. 326-336.
Christmann, et al., Human seroreactivity to gut microbiota antigens, J Allergy Clin Immunol, vol. 136, No. 5, Nov. 2015, pp. 1378-1386e5.
Dawson, Characterization of the Binding of Cholera Toxin to Ganglioside GM1 Immobilized onto Microtitre Plates, Journal of Applied Toxicology, vol. 25, No. 1, Jan. 2005, pp. 30-38.
De Souza et al., Immunopathogenesis of IBD: Current State of the Art, Gastroenterology & Hepatology, vol. 13, No. 1, Jan. 2016, 16 pages.
Delgoffe et al., The mTOR Kinase Differentially Regulates Effector and Regulatory T Cell Lineage Commitment, Immunity, vol. 30, No. 6, Jun. 2009, pp. 832-844.
Dertzbaugh et al., The Affinity of Cholera Toxin for Ni2+ Ion, Protein Engineering, vol. 11, No. 7, Jul. 1998, pp. 577-581.
Dubinsky et al., Serum Immune Responses Predict Rapid Disease Progression Among Children with Crohn's Disease: Immune Responses Predict Disease progression, The American Journal of Gastroenterology, vol. 101, No. 2, Feb. 2006, pp. 360-367.
Duck et al., Isolation of Flagellated Bacteria Implicated in Crohn's Disease, Inflammatory Bowel Disease, vol. 13, No. 10, Oct. 2007, pp. 1191-1201.
Elson et al., Host-Microbiota Interactions in Inflammatory Bowel Disease, Gut Microbes, vol. 3, No. 4, Jul.-Aug. 2012, pp. 332-344.
Elson et al., Molecular Approaches to the Role of the Microbiota in Inflammatory Bowel Disease, Annals of the New York Academy of Sciences, vol. 1072, No. 1, Aug. 2006, pp. 39-51.
Elson, Targeting microbiota flagellin-specific CD4+ memory T cells as a novel immunotherapy for Crohn's disease, Presentation at Crohns and Colitis Congress, 2019, Las Vegas, NV, 32 pages.
Fagarasan et al., Adaptive Immune Regulation in the Gut: T Cell-dependent and T Cell-independent IgA Synthesis, Annual Review of Immunology, vol. 28, 2010, pp. 243-273.
Fantini et al., Cutting Edge: TGF-beta Induces a Regulatory Phenotype in CD4+CD25− T cells through Foxp3 induction and down-regulation of Smad7, The Journal of Immunology vol. 172, No. 9, May 1, 2004, pp. 5149-5153.
Feng et al., Generation of Mucosal Dendritic Cells from Bone Marrow Reveals a Critical Role of Retinoic Acid, Journal of Immunology, vol. 185, No. 10, Nov. 2010, pp. 5915-5925.
Feng et al., Microbiota Innate Stimulation is a Prerequisite for T Cell Spontaneous Proliferation and Induction of Experimental Colitis, Journal of Experimental Medicine, vol. 207, No. 6, Jun. 7, 2010, pp. 1321-1332.
Feuerer et al., Genomic Definition of Multiple Ex Vivo Regulatory T Cell Subphenotypes, Proceedings of the National Academy of Sciences of the United States of America, vol. 107, No. 13, Mar. 2010, pp. 5919-5924.
Frentsch et al., Direct Access to CD4+ T Cells Specific for Defined Antigens According to CD154 Expression, Nature Medicine, vol. 11, No. 10, Oct. 2005, pp. 1118-1124.
George-Chandy et al., Cholera Toxin B Subunit as a Carrier Molecule Promotes Antigen Presentation and Increases CD40 and CD86 Expression on Antigen-Presenting Cells, Infection and immunity, vol. 69, No. 9, Sep. 2001, pp. 5716-5725.
Gertel et al., Immune Tolerance Induction with Multiepitope Peptide Derived from Citrullinated Autoantigens Attenuates Arthritis Manifestations in Adjuvant Arthritis Rats, The Journal of Immunology, vol. 194, Jun. 15, 2015, pp. 5674-5680.
Gill et al., Metagenomic Analysis of the Human Distal Gut Microbiome, Science, vol. 312, No. 5778, Jun. 2, 2006, pp. 1355-1359.
Gloudemans et al., The Mucosal Adjuvant Cholera Toxin B Instructs Non-Mucosal Dendritic Cells to Promote IgA Production via Retinoic Acid and TGF-Beta, PLoS One, vol. 8, No. 3, Mar. 20, 2013, pp. 1-10.
Gordon et al., Regulatory Dendritic Cells for Immunotherapy in Immunologic Diseases, Frontiers in Immunology, vol. 5, No. 7, Jan. 31, 2014, pp. 1-19.
Haidinger et al., A Versatile Role of Mammalian Target of Rapamycin in Human Dendritic Cell Function and Differentiation, Journal of Immunology, vol. 185, No. 7, Oct. 2010, pp. 3919-3931.
Hajishengallis et al., Mucosal Immunization with a Bacterial Protein Antigen Genetically Coupled to Cholera Toxin A2/B Subunits, Journal of Immunology, vol. 154, No. 9, May 1, 1995, pp. 4322-4332.
Hand et al., Acute Gastrointestinal Infection Induces Long-Lived Microbiota-Specific T Cell Responses, Science, vol. 337, No. 6101, Sep. 21, 2012, pp. 1553-1556.
Hegazy et al., Circulating and Tissue-Resident CD4D T Cells with Reactivity to Intestinal Microbiota are Abundant in Healthy Individuals and Function is Altered During Inflammation, Gastroenterology, vol. 153, Nov. 2017, pp. 1320-1337.
Hay et al., Upstream and downstream of mTOR, Genes & Development, vol. 18, No. 16, Aug. 2004, pp. 1926-1945.
Holmgren et al., Mucosal Adjuvants and Anti-infection and Anti-Immunopathology Vaccines Based on Cholera Toxin, Cholera Toxin B Subunit and CpG DNA, Immunology Letters, vol. 97, No. 2, Mar. 2005, pp. 181-188.
Holmgren et al., Mucosal Immunity and Vaccines, Nature Medicine, vol. 11, No. 4, Apr. 2005, pp. S45-S53.
Holmgren et al., Tissue Receptor for Cholera Exotoxin: Postulated Structure from Studies with GM1 Ganglioside and Related Glycolipids, Infection and Immunity, vol. 8, No. 2, Aug. 1973, pp. 208-214.
Imam et al., Effector T Helper Cell Subsets in Inflammatory Bowel Diseases, Frontiers in Immunology, vol. 9, Article 1212, Jun. 1, 2018, 16 pages.
Inoki et al., AMPK and mTOR in Cellular Energy Homeostasis and Drug Targets, The Annual Review of Pharmacology and Toxicology, vol. 52, Feb. 2012, pp. 381-400.
Kaetzel, The Polymeric Immunoglobulin Receptor: Bridging Innate and Adaptive Immune Responses at Mucosal Surfaces, Immunological Reviews, vol. 206, No. 1, Aug. 2005, pp. 83-99.
Kanai et al., Persistent Retention of Colitogenic CD4+ Memory T Cells Causes Inflammatory Bowel Diseases to Become Intractable, Inflammatory Bowel Disease, vol. 15, No. 6, Jun. 2009, pp. 926-934.
Kelly et al., Breaking Down the Barriers: The Gut Microbiome, Intestinal Permeability and Stress-Related Psychiatric Disorders, Frontiers in Cellular Neuroscience, vol. 9, No. 392, Oct. 2015, pp. 1-20.
Khor et al., Genetics and Pathogenesis of Inflammatory Bowel Disease, Nature, vol. 474, No. 7351, Dec. 16, 2011, pp. 307-317.
Konrad et al., Tight Mucosal Compartmentation of the Murine Immune Response to Antigens of the Enteric Microbiota, Gastroenterology, vol. 130, No. 7, Jun. 2006, pp. 2050-2059.
Kugathasan et al., Prediction of Complicated Disease Course for Children Newly Diagnosed with Crohn's Disease: A Multicentre Inception Cohort Study, Lancet, vol. 389, No. 10080, Apr. 29, 2017, pp. 1710-1718.
Laplante et al., mTOR Signaling in Growth Control and Disease, Cell, vol. 149, Apr. 13, 2012, pp. 274-293.
Lau et al., Therapeutic Peptides: Historical Perspectives, Current Development Trends, and Future Directions, Bioorganic & Medicinal Chemistry, vol. 26, Jun. 1, 2018, pp. 2700-2707.
Li et al., Rapamycin: One Drug, Many Effects, Cell Metabolism, vol. 19, Mar. 4, 2014, pp. 373-379.

(56) References Cited

OTHER PUBLICATIONS

Limon et al., mTOR Kinase Inhibitors Promote Antibody Class Switching via mTORC2 Inhibition, Proceedings of the National Academy of Sciences of the United States of America, vol. 111, No. 47, Nov. 10, 2014, pp. E5076-E5085.
Lodes et al., Bacterial Flagellin Is a Dominant Antigen in Crohn Disease, The Journal of Clinical Investigation, vol. 113, No. 9, May 2004, pp. 1296-1306.
Macedo et al., Immunoregulatory Properties of Rapamycin-conditioned Monocyte-derived Dendritic Cells and their Role in Transplantation, Transplantation Research, vol. 1, No. 16, Sep. 2012, pp. 1-7.
Mantis et al., Secretory IgA's Complex Roles in Immunity and Mucosal Homeostasis in the Gut, Mucosal Immunology, vol. 4, No. 6, Nov. 2011, pp. 603-611.
Martinez-Outschoorn et al., Cancer Metabolism: A Therapeutic Perspective, Nature Reviews Clinical Oncology, vol. 14, No. 1, Jan. 2017, 26 pages.
Massey et al., Use of Sirolimus (Rapamycin) to Treat Refractory Crohn's Disease, Gut, vol. 57, No. 9, Sep. 2008, pp. 1294-1296.
Maynard et al., Regulatory T Cells Expressing Interleukin 10 Develop from Foxp3+ and Foxp3— Precursor Cells in the Absence of Interleukin 10, Nature Immunology, vol. 8, No. 9, Sep. 2007, pp. 931-941.
Mckenzie et al., Cholera Toxin B Subunit as a Carrier Protein to Stimulate a Mucosal Immune Response, Journal of Immunology, vol. 133, No. 4, Oct. 1984, pp. 1818-1824.
International Application No. Application No. PCT/US2020/017319, International Preliminary Report on Patentability mailed on Aug. 19, 2021, 15 pages.
International Application No. Application No. PCT/US2020/017319, International Search Report and Written Opinion mailed on Aug. 13, 2020, 22 pages.
International Application No. PCT/US2020/017319, Invitation to Pay Additional Fees and, Where Applicable, Protest Fee mailed on Jun. 22, 2020, 15 pages.
Michalek et al., Cutting Edge: Distinct Glycolytic and Lipid Oxidative Metabolic Programs are Essential for Effector and Regulatory CD4+ T Cell Subsets, The Journal of Immunology, vol. 186, Feb. 11, 2011, pp. 3299-3303.
Moon et al., Naive CD4+ T Cell Frequency Varies for Different Epitopes and Predicts Repertoire Diversity and Response Magnitude, Immunity, vol. 27, Aug. 2007, pp. 203-213.
Mucida et al., Reciprocal TH17 and Regulatory T Cell Differentiation Mediated by Retinoic Acid, Science, vol. 317, No. 5835, Aug. 2007, pp. 256-260.
Mutalib et al., The Use of Sirolimus (Rapamycin) in the Management of Refractory Inflammatory Bowel Disease in Children, Journal of Crohn's and Colitis, vol. 8, No. 12, Dec. 2014, pp. 1730-1734.
Nemoto et al., Bone Marrow Retaining Colitogenic CD4+ T Cells May Be a Pathogenic Reservoir for Chronic Colitis, Gastroenterology, vol. 132, Jan. 2007, pp. 176-189.
Nemoto et al., Bone Marrow-Mesenchymal Stem Cells are a Major Source of Interleukin-7 and Sustain Colitis by Forming the Niche for Colitogenic CD4 Memory T Cells, Gut, vol. 62, No. 8, Nov. 9, 2012, pp. 1142-1152.
Neurath, Current and Emerging Therapeutic Targets for IBD, Gastroenterology & Hepatology, vol. 14, May 2017, pp. 269-278.
Newton et al., Immunometabolism of Regulatory T Cells, Nature Immunology, vol. 17, No. 6, May 19, 2016, pp. 618-625.
Ng et al., Worldwide Incidence and Prevalence of Inflammatory Bowel Disease in the 21st Century: A Systematic Review of Population-Based Studies, Lancet, vol. 390, Dec. 23-30, 2017, pp. 2769-2778.
Papadakis et al., Anti-Flagellin (CBir1) Phenotypic and Genetic Crohn's Disease Associations, Inflammatory Bowel Disease, vol. 13, No. 5, May 2007, pp. 524-530.
Pearce et al., Metabolic Pathways in Immune Cell Activation and Quiescence, Immunity, vol. 38, Apr. 18, 2013, pp. 633-643.
Pernicova et al., Metformin-Mode of Action and Clinical Implications for Diabetes and Cancer, Endocrinology, vol. 10, Mar. 2014, pp. 143-156.
Pollizzi et al., Integrating Canonical and Metabolic Signalling Programmes in the Regulation of T Cell Responses, Nature Reviews Immunology, vol. 14, No. 7, Jul. 2014, pp. 435-446.
Pollizzi et al., mTORC1 and mTORC2 Selectively Regulate CD8+ T Cell Differentiation, The Journal of Clinical Investigation, vol. 125, No. 5, May 2015, pp. 2090-2108.
Powell et al., Regulation of Immune Responses by mTOR, Annual Review of Immunology, vol. 30, 2012, pp. 39-68.
Robertson et al., DO11.10 and OT-II T Cells Recognize a C-Terminal Ovalbumin 323-339 Epitope, The Journal of Immunology, vol. 164, May 1, 2000, pp. 4706-4712.
Sandborn et al., Natalizumab Induction and Maintenance Therapy for Crohn's Disease, The New England Journal of Medicine, vol. 353, No. 18, Nov. 3, 2005, pp. 1912-1925.
Sandborn et al., Vedolizumab as Induction and Maintenance Therapy for Crohn's Disease, The New England Journal of Medicine, vol. 369, No. 8, Aug. 22, 2013, pp. 711-721.
Saxton et al., mTOR Signaling in Growth, Metabolism, and Disease, Cell, vol. 168, Mar. 9, 2017, pp. 960-976.
Schmidt et al., Molecular Mechanisms of Tregmediated T Cell Suppression, Frontiers in Immunology, vol. 3, No. 51, Mar. 2012, 20 pages.
Schnitzler et al., Induction of Cell Signaling Events by the Cholera Toxin B Subunit in Antigen-Presenting Cells, Infection and Immunity, vol. 75, No. 6, Jun. 2007, pp. 3150-3159.
Sharma et al., Plasmacytoid Dendritic Cells from Mouse Tumor-Draining Lymph Nodes Directly Activate Mature Tregs via Indoleamine 2,3-Dioxygenase, Journal of Clinical Investigation, vol. 117, No. 9, Sep. 2007, pp. 2570-2582.
Shrestha et al., Tsc1 Promotes the Differentiation of Memory CD8+ T Cells via Orchestrating the Transcriptional and Metabolic Programs, Proceedings of the National Academy of Sciences of the United States of America (PNAS), vol. 111, No. 41, Oct. 14, 2014, pp. 14858-14863.
Smits et al., Cholera Toxin B Suppresses Allergic Inflammation Through Induction of Secretory IgA, Mucosal Immunology, vol. 2, No. 4, Jul. 2009, pp. 331-339.
Smythies et al., Human Intestinal Macrophages Display Profound Inflammatory Anergy Despite Avid Phagocytic and Bacteriocidal Activity, The Journal of Clinical Investigation, vol. 115, No. 1, Jan. 2005, pp. 66-75.
Smythies et al., Inflammation Anergy in Human Intestinal Macrophages is Due to Smad-induced IκBα Expression and NF-κB Inactivation, The Journal of Biological Chemistry, vol. 285, No. 25, Jun. 18, 2010, pp. 19593-19604.
Strober et al., Reciprocal IFN-Gamma and TGF-Beta Responses Regulate the Occurrence of Mucosal Inflammation, Immunology Today, vol. 18, No. 2, Feb. 1997, pp. 61-64.
Sun et al., B Lymphocytes Treated in Vitro with Antigen Coupled to Cholera Toxin B Subunit Induce Antigen-specific Foxp3(+) Regulatory T Cells and Protect Against Experimental Autoimmune Encephalomyelitis, Journal of Immunology, vol. 188, No. 4, Feb. 2012, pp. 1686-1697.
Sun et al., Cholera Toxin B Subunit: An Efficient Transmucosal Carrier-delivery System for Induction of Peripheral Immunological Tolerance, Proceedings of the National Academy of Sciences of the United States of America, vol. 91, No. 23, Nov. 1994, pp. 10795-10799.
Sun et al., Mucosally Induced Immunological Tolerance, Regulatory T Cells and the Adjuvant Effect by Cholera Toxin B Subunit, Scandinavian Journal of Immunology, vol. 71, No. 1, Jan. 2010, pp. 1-11.
Sun et al., Oral Administration of Cholera Toxin B Subunit Conjugated to Myelin Basic Protein Protects Against Experimental Autoimmune Encephalomyelitis by Inducing Transforming Growth Factor-beta-secreting Cells and Suppressing Chemokine Expression, International Immunology, vol. 12, No. 10, Oct. 2000, pp. 1449-1457.

(56) References Cited

OTHER PUBLICATIONS

Sun et al., Small Intestine Lamina Propria Dendritic Cells Promote De Novo Generation of Foxp3 T Reg Cells via Retinoic Acid, Journal of Experimental Medicine, vol. 204, No. 8, Aug. 2007, pp. 1775-1785.
Targan et al., Antibodies to CBir1 Flagellin Define a Unique Response That is Associated Independently with Complicated Crohn's Disease, Gastroenterology, vol. 128, Jun. 2005, pp. 2020-2028.
Tarkowski et al., Treatment of Experimental Autoimmune Arthritis by Nasal Administration of a Type II Collagen-Cholera Toxoid Conjugate Vaccine, Arthritis & Rheumatology, vol. 42, No. 8, Aug. 1999, pp. 1628-1634.
Thaiss et al., Exploring New Horizons in Microbiome Research, Cell Host Microbe, vol. 15, Jun. 11, 2014, pp. 662-667.
Thomson et al., Immunoregulatory Functions of mTOR Inhibition, Nature Reviews Immunology, vol. 9, May 2009, pp. 324-337.
Thornton et al., CD4+CD25+ Immunoregulatory T Cells Suppress Polyclonal T Cell Activation In Vitro by Inhibiting Interleukin 2 Production, Journal of Experimental Medicine, vol. 188, No. 2, Jul. 20, 1998, pp. 287-296.
Tomita et al., Systemic, But Not Intestinal, IL-7 Is Essential for the Persistence of Chronic Colitis, The Journal of Immunology, vol. 180, Jan. 1, 2008, pp. 383-390.
Turnbaugh et al., An Obesity-Associated Gut Microbiome with Increased Capacity for Energy Harvest, Nature, vol. 444, No. 7122, Dec. 2006, pp. 1027-1031.
Turner et al., Sirolimus Enhances the Magnitude and Quality of Viral-Specific CD8+ T-Cell Responses to Vaccinia Virus Vaccination in Rhesus Macaques, American Journal of Transplantation, vol. 11, No. 3, Mar. 2011, pp. 613-618.
Turnquist et al., Rapamycin-Conditioned Dendritic Cells are Poor Stimulators of Allogeneic CD4+ T Cells, but Enrich for Antigen-specific Foxp3+ T Regulatory Cells and Promote Organ Transplant Tolerance, The Journal of Immunology, vol. 178, No. 11, Jun. 2007, pp. 7018-7031.
Valmori et al., Rapamycin-Mediated Enrichment of T Cells with Regulatory Activity in Stimulated CD4+ T Cell Cultures is Not Due to the Selective Expansion of Naturally Occurring Regulatory T Cells but to the Induction of Regulatory Functions in Conventional CD4+ T Cells, The Journal of Immunology, vol. 177, Jul. 15, 2006, pp. 944-949.
Van Der Windt et al., Metabolic Switching and Fuel Choice During T-cell Differentiation and Memory Development, Immunological Reviews, vol. 249, No. 1, Sep. 2012, pp. 27-42.
Whitehead et al., Establishment of Conditionally Immortalized Epithelial Cell Lines from Both Colon and Small Intestine of Adult H-2Kb-tsA58 Transgenic Mice, Proceedings of the National Academy of Sciences of the United States of America, vol. 90, Jan. 1993, pp. 587-591.
Woogen et al., Inhibition of Murine Lymphocyte Proliferation by the B Subunit of Cholera Toxin, Journal of Immunology, vol. 139, No. 11, Dec. 1987, pp. 3764-3770.
Woogen et al., Inhibition of Murine T cell activation by cholera toxin B subunit is not mediated through the phosphatidylinositol second messenger system, J. Immunol., vol. 150, No. 8, 1993, pp. 3274-3283.
Workman et al., The Development and Function of Regulatory T Cells, Cellular and Molecular Life Sciences, vol. 66, No. 16, Aug. 2009, pp. 2603-2622.
Xu et al., mTOR, Linking Metabolism and Immunity, Seminars in Immunology, vol. 24, No. 6, Dec. 2012, pp. 429-435.
Zeng et al., Metabolic Control of Regulatory T Cell Development and Function, Trends in Immunology, vol. 36, No. 1, Sep. 20, 2014, pp. 3-12.
Zeng et al., mTORC1 and mTORC2 Kinase Signaling and Glucose Metabolism Drive Follicular Helper T Cell Differentiation, Immunity, vol. 45, Sep. 20, 2016, pp. 540-554.
Zhao et al., CD4+ T Cell Activation and Concomitant mTOR Metabolic Inhibition Can Ablate Microbiota-Specific Memory Cells and Prevent Colitis, Science Immunology, vol. 5, Dec. 11, 2020, 14 pages.
Zhao et al., Selective Induction of Homeostatic Th17 Cells in the Murine Intestine by Cholera Toxin Interacting with the Microbiota, The Journal of Immunology, vol. 199, Jul. 1, 2017, pp. 312-322.
European Patent Application No. 20711363.0, Communication under Rule 164(2)(a) EPC, mailed Feb. 27, 2025, 8 pages.

* cited by examiner

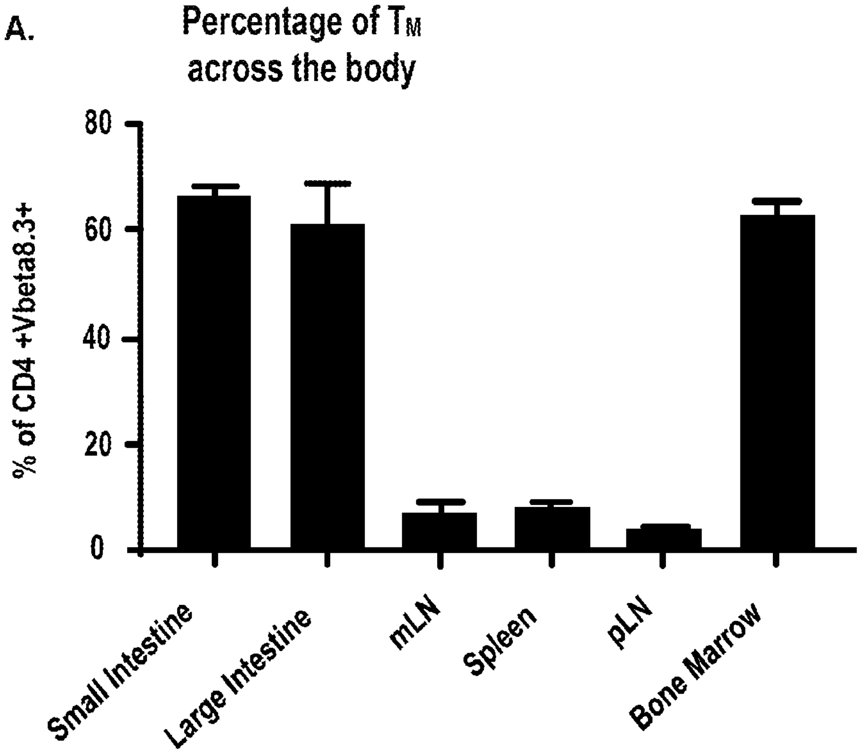
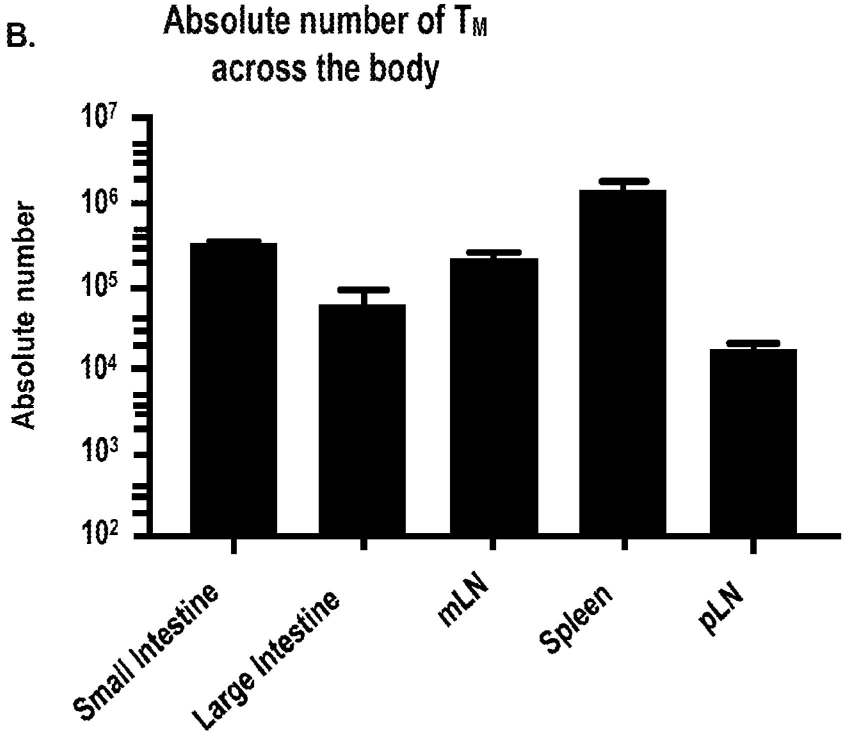
FIGS. 1A-B

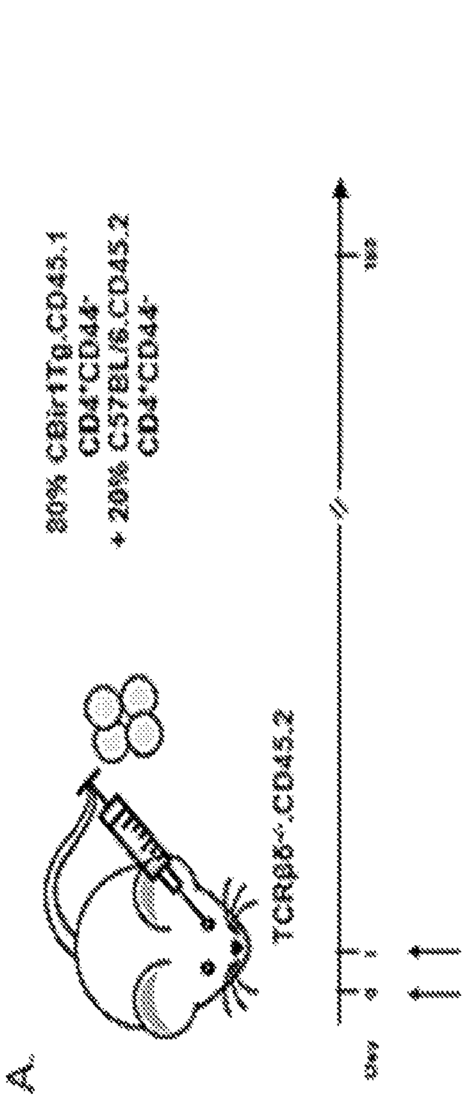
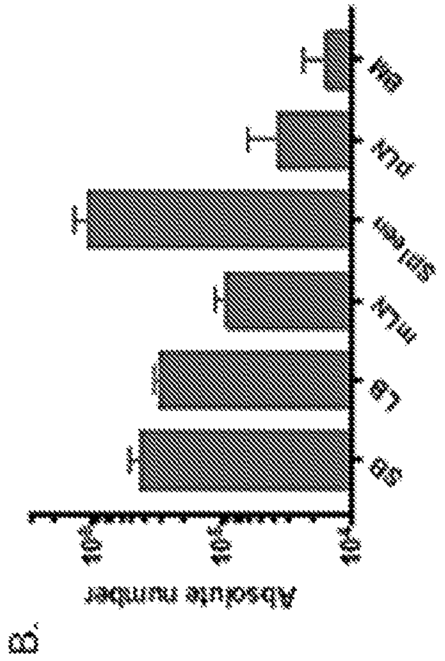
FIG. 7B
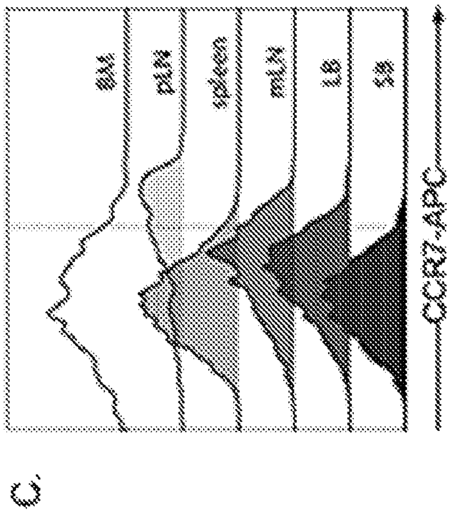
FIG. 7C

H.

I.

J.

K.

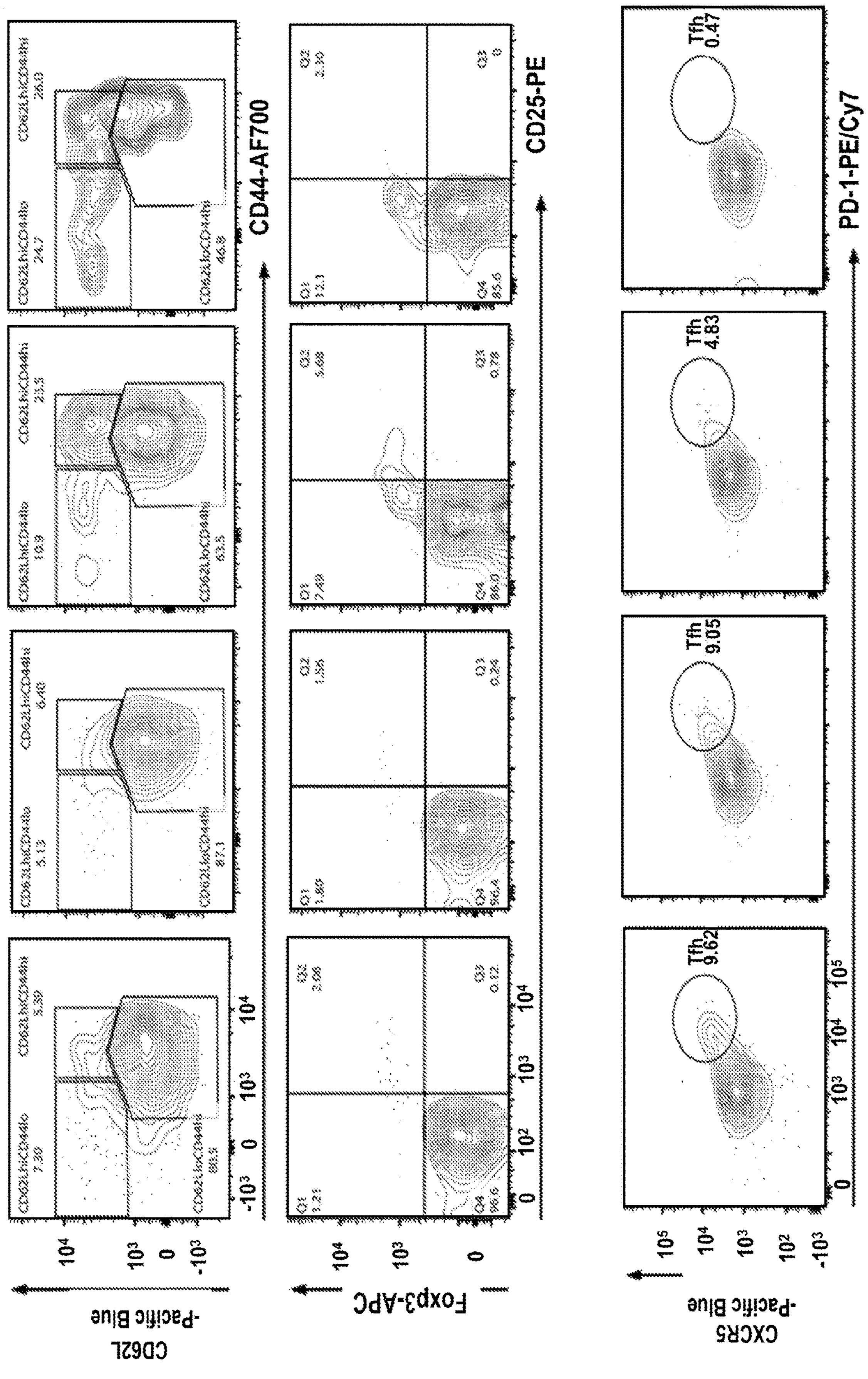
FIG. 10C CON'T

H.

I.

J.

M.

IMMUNOTHERAPY FOR THE TREATMENT AND PREVENTION OF INFLAMMATORY BOWEL DISEASE

PRIOR RELATED APPLICATION

This application claims the benefit of U.S. Provisional Application No. 62/802,873 filed on Feb. 8, 2019 which is hereby incorporated by reference in its entirety.

STATEMENT REGARDING FEDERALLY FUNDED RESEARCH

This invention was made with government support under Grant No. DK071176 awarded by the National Institutes of Health. The government has certain rights in the invention.

SEQUENCE LISTING

A Sequence Listing conforming to the rules of WIPO Standard ST.25 is hereby incorporated by reference. Said Sequence Listing has been filed as an electronic document via PatentCenter in ASCII formatted text. The electronic document, created on Jan. 29, 2025, is entitled "UAB191US1_ST25.txt", and is 18 kilobytes in size.

BACKGROUND

As a global disease, the prevalence of inflammatory bowel disease (IBD) is over 0.3% in developed countries and continues to rise in developing countries. Its major forms, Crohn's disease and ulcerative colitis, are associated with substantial morbidity and huge medical care costs. Current treatments and therapies typically treat the symptoms of the disorders and do not provide curative treatment.

SUMMARY

Provided herein are methods for treating or preventing inflammatory bowel disease. The methods comprise administering to a subject having inflammatory bowel disease or at risk of developing inflammatory bowel disease (a) an effective amount of a polypeptide comprising one or more flagellin T-cell receptor (TCR) epitopes; and (b) an effective amount of an agent that reduces flagellin antigen-specific memory T cells and/or increases regulatory T cells in the subject. In some embodiments, the agent that that reduces flagellin antigen-specific memory T cells and/or increases regulatory T cells in the subject is a metabolic inhibitor.

Also provided are methods for delaying or reducing the intensity of a relapse or flare of an inflammatory bowel disease in a subject. The methods comprise administering to a subject (a) an effective amount of a polypeptide comprising one or more flagellin T-cell receptor (TCR) epitopes; and (b) an effective amount of an agent that reduces flagellin antigen-specific memory T cells and/or increases regulatory T cells in the subject. In some embodiments, the agent that that reduces flagellin antigen-specific memory T cells and/or increases regulatory T cells in the subject is a metabolic inhibitor.

BRIEF DESCRIPTION OF THE DRAWINGS

The present application includes the following figures. The figures are intended to illustrate certain embodiments and/or features of the compositions and methods, and to supplement any description(s) of the compositions and methods. The figures do not limit the scope of the compositions and methods, unless the written description expressly indicates that such is the case.

FIGS. 1A-1B show that CD4 memory T ($T_M$) cells are widely distributed in CBir1 T cell receptor transgenic (CBir1 TCR Tg) mice. This transgenic mouse line is specific for CBir1 flagellin.

FIGS. 7A-7E show that microbiota flagellin-specific $CD4^+$ $T_M$ cells are present locally in the intestine and circulating in the periphery. (A) TCRβδ−/− mice were transferred with $8\times10^5$ naïve $CD4^+$ T cells from CBir1Tg·CD45.1 mice and $2\times10^5$ naïve CD4+ T cells from B6·CD45.2 mice, followed by subcutaneous injection of 3 μg MEP1 on the next day. Recipient mice were maintained under SPF environment for 6 months for microbiota flagellin-specific $CD4^+$ $T_M$ response development. Upon sacrifice, lymphocytes were isolated from the small bowel (SB), large bowel (LB), mLN, spleen, inguinal lymph nodes (pLN), and bone marrow (BM) of recipient mice and analyzed with FACS. (B) Absolute numbers of CBir1-specific (CD45.1+) $CD4^+CD44^+CD127^+$ $T_M$ cells in different tissues. (C) Percent of CCR7 expression on $CD4^+$ $T_M$ cells in different tissues, whereas the absolute numbers of $CD4^+$ $T_M$ cells expressing CCR7 is shown in (D). Flow sorted $CD45.1^+$ $CD4^+CD44^+CD127^+$ $T_M$ cells from the spleen of colitic recipient mice were used for the 2° transfer. For 2° transfer, Rag−/− mice received $5\times10^5$ Tm or CBir1Tg CD4+CD44− (Tn) cells on Day 0, followed by i.p. injection of rapamycin (1 μg/g/day) resuspended in 0.2% CMC or vehicle alone on days 1-5 and days 8-12. Histological analysis on cecal and colonic tissues on day 20 is shown in (E).

DETAILED DESCRIPTION

Figure 2:
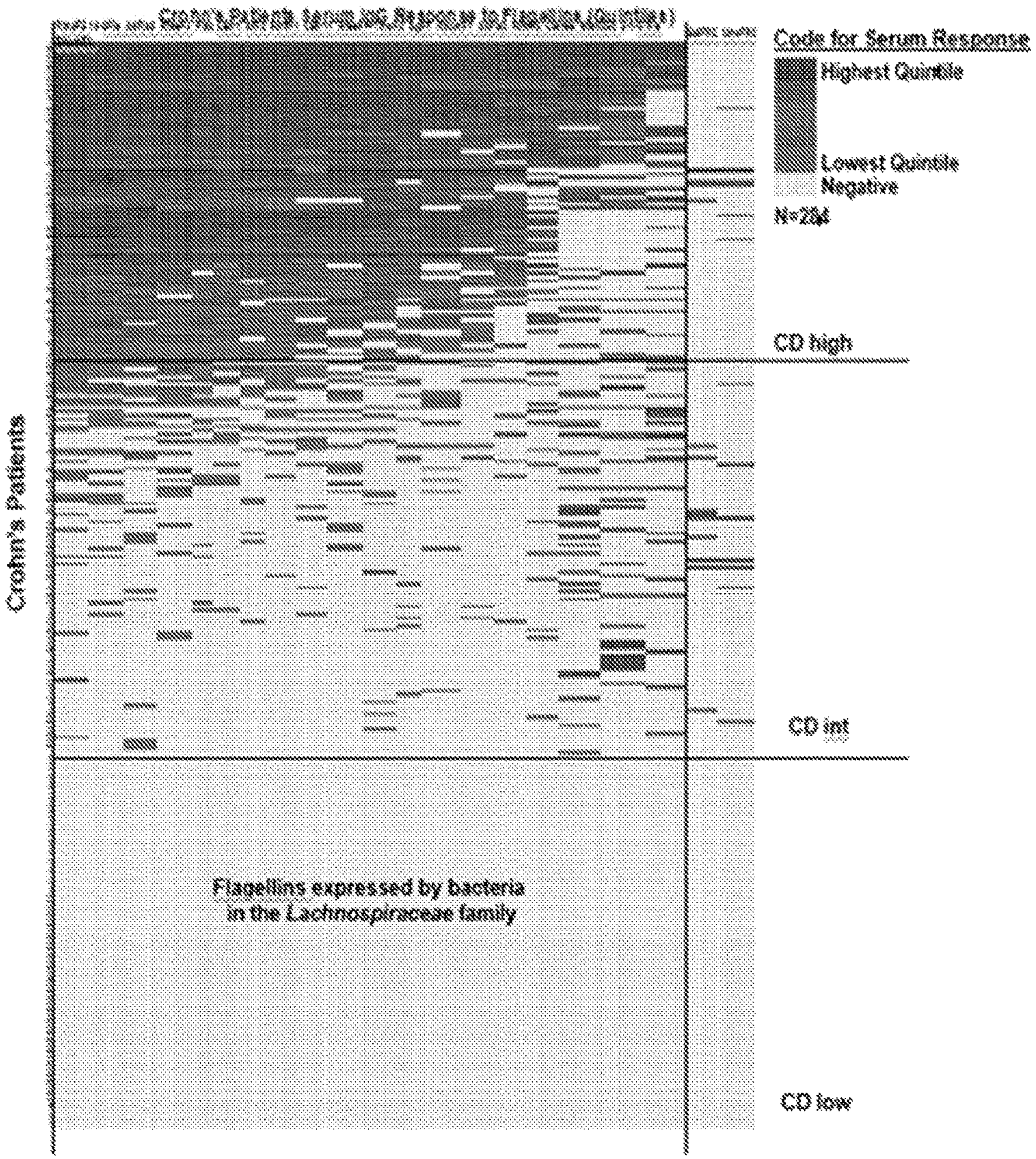
FIG. 2 shows that a subset of Crohn's patients has broad IgG reactivity to microbiota flagellins.

Currently there is no cure for Crohn's disease or ulcerative colitis, the two main types of IBD. IBD is a chronic condition, and people with IBD will typically need treatment throughout their lives. As shown herein, the pathogenesis of IBD is due to an abnormal immune response, particularly a $CD4^+$ T cell response, to microbiota antigens in genetically-susceptible hosts. Microbiota flagellins, especially those that belong to the Lachnospiraceae family, were identified as immunodominant antigens driving the adaptive cellular and humoral immune responses in murine colitis models. Similarly, over half of the patients with Crohn's disease have elevated serological reactivity to CBir1 and its related flagellins, which is generally companied with a more complicated clinical course.

Much has been learned by focusing on CD4+ T effector ($T_E$) cells (Th1, Th17, and Th1/Th17), but less is known about CD4+ T memory ($T_M$) cells reactive to the gut microbiota. Long-lived microbiota-specific CD4+ $T_M$ cells are present in healthy human individuals, and can be generated during intestinal inflammation and infections, as shown in murine models. At steady state, these CD4+ $T_M$ cells are widely distributed in tissues including the colonic lamina propria (LP), mesenteric lymph nodes (mLNs), spleen, blood, and bone marrow (BM). The fact that they responded quickly by drastically proliferating and producing cytokines such as IFNγ and IL-17A when challenged with a microbiota antigen in the periphery in mice and gave rise to secondary colitis indicates that microbiota-specific $CD4^+$ TM cells serve as a potential pathogenic $CD4^+$ T effector cell reservoir for later-on intestinal inflammations.

Resting $CD4^+$ T naïve ($T_N$) and $T_M$ cells keep a low level of metabolism but undergo a profound metabolic transition from using mitochondrial oxidative phosphorylation (OXPHOS) and fatty acids oxidation to predominantly engaging glycolysis when stimulated through the T cell receptor (TCR) and co-stimulatory molecules. This metabolic status switch is primarily controlled by the mammalian target of rapamycin (mTOR) complex. Thus, activation of mTOR is needed for T cell expansion and is an inescapable metabolic checkpoint for activating $T_N$ and $T_M$ cells. In addition, 5' AMP-activated protein kinase (AMPK), which is upstream of the mTOR pathway and negatively regulates its activity, is upregulated in $T_M$ cells. As shown herein, metabolic inhibition during cell activation (MIdCA), through inhibition of mTOR and/or activation of AMPK, results in $CD4^+$ T naïve and memory cell death as well as anergy, thus leading to the depletion of pathogenic microbiota-specific CD4+ T cells. The results provided herein demonstrate that metabolic inhibition during microbiota-specific $CD4^+$ T cell activation is an effective method to eliminate a pathogenic $CD4^+$ T cell reservoir and induce Treg cells that provide antigen-specific and bystander suppression.

Provided herein are methods for treating or preventing inflammatory bowel disease. The methods comprise administering to a subject having inflammatory bowel disease or at risk of developing inflammatory bowel disease (a) an effective amount of a polypeptide comprising one or more flagellin T-cell receptor (TCR) epitopes; and (b) an effective amount of an agent that reduces flagellin antigen-specific memory T cells and/or increases regulatory T cells in the subject.

Also provided are methods for delaying or reducing the intensity of a relapse or flare of an inflammatory bowel disease in a subject. The methods comprise administering to a subject (a) an effective amount of a polypeptide comprising one or more flagellin T-cell receptor (TCR) epitopes; and (b) an effective amount of an agent that reduces flagellin antigen-specific memory T cells and/or increases regulatory T cells in the subject.

As used throughout, inflammatory bowel disease (IBD) is a group of intestinal disorders that cause chronic or prolonged inflammation of the digestive tract. Inflammation can occur anywhere along the digestive tract, for example, in the mouth, esophagus, stomach, small intestine and/or large intestine. Examples of inflammatory bowel disease include, but are not limited to, Crohn's disease and ulcerative colitis. In Crohn's disease, the condition most commonly affects the small intestine and colong, but it can occur anywhere in the gastrointestinal tract. Ulcerative colitis is typically limited to the colon, i.e, the large intestine.

As used herein, the terms, polypeptide, peptide, and protein are used interchangeably herein to refer to a polymer of amino acid residues. As used herein, the terms encompass amino acid chains of any length, including full-length proteins, wherein the amino acid residues are linked by covalent peptide bonds.

As used herein, a T cell receptor epitope is a peptide that can be recognized by T-cell receptors after a particular antigen has been intracellularly processed, bound to at least one MHC molecule and expressed on the surface of an antigen presenting cell as a MHC-peptide complex.

In some methods, the polypeptide comprising one or more flagellin TCR epitopes comprises one or more microbiota flagellin TCR epitopes. In some methods, the one or more flagellin TCR epitopes included in the polypeptide are TCR epitopes selected from one or more flagellins selected from the group consisting of *R. inulinivorans, R. hominis, R. faecis, Eubacteria rectale, R. intestinalis*, (*Agathobacter rectalis*) and a Lachnospiracae flagellin. In some methods the Lachospiracae flagellin is selected from the group consisting of Lachnospiraceae Flax. Lachnospiraceae 14-2. Lachnospiraceae A4 and Lachnospiraceae CBir1. In some methods, one or more flagellin TCR epitopes included in the polypeptide are from human microbiota. In some methods one or more flagellin TCR epitopes included in the polypeptide are from murine microbiota.

In some methods, the polypeptides provided herein comprise, consist of, or consist essentially of, one or more flagellin TCR epitopes comprising SEQ ID NO: 1 (DMATEMVKYSNANILSQAGQ). In some methods, the polypeptide provided herein further comprise SEQ ID NO: 2 (ISQAVHAAHAEINEAGR). In some methods, the polypeptide further comprises SEQ ID NO: 3 (EAWGALANWAVDSA). An example of a polypeptide comprising SEQ ID NO: 1. SEQ ID NO: 2 and SEQ ID NO: 3 is SEQ ID NO: 4 (MRGSHHHHHHGSMRKQIRGLTQASTNAEDGISSVQTAEGALTEVHDMLQRMNELA IQAANGTDMATEMVKYSNANILSQAGQDMATEMVKYSNANILSQAGQDMATEMV KYSNANILSQAGQISQAVHAAHAEINEAGREAWGALANWAVDSARGSHHHHHH). Another example of a multi-epitope polypeptide that can be used in the methods provided herein is SEQ ID NO: 5 (MVVQHNMQAMNANRMLNVTTLTEVHSMLQRMNELAVQASNGMVVQHNMTAA NANRMGETHSILQRMNELATQAANMVVQHNLTAMNANRQLVGTT GMVVQHNMQ AANANRMLGITSVHSMLQRMNELAVQAASNGTNSMVVQHNMQAANANRMLNVT TLTEVHSMLQRMNELATQSANGLTEVHSMLQRMNELAVQSSNGDMAEEMVEYSK NNILAQAGQSMLAQANQSMAEEMVNYSKNNILAAQAGQSMLAQANQMAKEMVN YSKNNILAQAGQSMLAQANDMAEEMVTYSKNILAQAGQSMLAQANQMVVQHNL RAMNSNRMLGITQSAQRSLLGAVQNRLEHTINNNEAHSILQRMNELAVQGANDVEY SKNNILAQAGQSMLAQANQMVVQHNLRAMNSNRMLSITQDMATEMVKFSNSNILA QAGQMVVQHNLRAMNANRMLGITTEVHDMLQRMNELAVKAAN).

SEQ ID NO: 5 comprises SEQ ID NO: 6 (MVVQHNMQAMNANRMLNVTT), SEQ ID NO: 7 (LTEVHSMLQRMNELAVQASNG), SEQ ID NO: 8 (MVVQHNMTAANANRM), and SEQ ID NO: 9 (GETHSILQRMNELATQAAN), as set forth in Table 1.

Other, non-limiting examples of flagellin TCR epitopes that can be included in any of the multi-epitope polypeptides described herein are set forth in Table 1. Table 1 indicates the source of the individual peptides shown, for example, as shown above in SEQ ID NO: 5, which is a multiepitope peptide that can be used as a therapeutic agent. The epitopes shown in Table 1 can be linked directly to one another in the order as they are listed in Table 1 for example, SEQ ID NO: 6-SEQ ID NO: 27). These epitope peptides can also be spaced apart with linkers, or used in a different order.

In some examples, the polypeptide comprises SEQ ID NO: 10 (MVVQHNLTAMNANRQLVGTTG), derived from *R. hominis*, as set fort in Table 1. In some examples, the polypeptide comprises SEQ ID NO: 37 (MVVQHNMQAANANRMLGITS), derived from *R. faecis*, as set forth in Table 1. In some examples, the polypeptide comprises SEQ ID NO: 11 (MVVQHNMQAANANRMLNVTT), SEQ ID NO: 12 (LTEVHSMLQRMNELATQSANG) and/or SEQ ID NO: 13 (LTEVHSMLQRMNELAVQSSNG) derived from *Eubacteria rectale*, as set fort in Table 1. In some examples, the polypeptide comprises SEQ ID NO: 14 (DMAEEMVEYSKNNILAQAGQSMLAQANQS), derived from *R. hominis, R. inulinivorans*, or *R. intestinalis*, as shown in Table 1. In some examples, the polypeptide comprises SEQ ID NO: 15 (MAEEMVNYSKNNILAAQAGQSMLAQANQ), derived from *R. inulinivorans*, or *Eubacteria rectale*, as shown in Table 1. In some examples, the polypeptide comprises SEQ ID NO: 16 (MAKEMVNYSKNNILAQAGQSMLAQAN), derived from *R. faecis* or *Eubacteria rectale*, as shown in Table 1. In some examples, the polypeptide comprises SEQ ID NO: 17 (DMAEEMVTYSKNNILAQAGQSMLAQANQ), derived from *R. intestinalis* or *R. inulinivorans*, as shown in Table 1. In some examples, the polypeptide comprises SEQ ID NO: 18 (MVVQHNLRAMNSNRMLGITQ) and/or SEQ ID NO: 19 (SAQRSLLGAVQNRLEHTINN), derived from Lachnospiracae Flax, as shown in Table 1. In some examples, the polypeptide comprises SEQ ID NO: 20 (NEAHSILQRMNELAVQGAND) and/or SEQ ID NO: 21 (VEYSKNNILAQAGQMLAQANQ), derived from Lachnospiracae 14-2, as shown in Table 1. In some examples, the polypeptide comprises SEQ ID NO: 22 (MVVQHNLRAMNSNRMLSITQ) and/or SEQ ID NO: 23 (DMATEMVKFSNSNILAQAGQ), derived from Lachnospiracae A4, as shown in Table 1.

In some examples, the polypeptide comprises SEQ ID NO: 24 (MVVQHNLRAMNANRMLGIT) and/or SEQ ID NO: 25 (TEVHDMLQRMNELAVKAAN), derived from Lachnospiracae A4, as shown in Table 1. In other examples, a polypeptide comprising SEQ ID NO: 26 (MKVKVLSLLVPALLVAGAAN) and/or SEQ ID NO: 27 (VDVGATYYFNKNMSTYVDYK), can be administered. In some examples, the polypeptide comprises one or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more peptide epitopes selected from the group consisting of SEQ ID NO: 6, SEQ ID NO: 7 SEQ ID NO: 8, SEQ ID NO: 9. SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26 and SEQ ID NO: 27. In some examples, the polypeptide comprises SEQ ID NO: 6-SEQ ID NO: 27. Optionally, one or more copies of each epitope peptide can be included in the polypeptide.

In some embodiments, any of the polypeptides described herein can be conjugated to a heterologous moiety. The heterologous moiety can be, e.g., a heterologous polypeptide, a therapeutic agent (e.g., a toxin or a drug), or a detectable label such as, but not limited to, a radioactive label, an enzymatic label, a fluorescent label, a heavy metal label, a luminescent label, or an affinity tag such as biotin or streptavidin. Suitable heterologous polypeptides include, e.g., an antigenic tag (e.g., FLAG (DYKDDDDK) (SEQ ID NO:31), polyhistidine (6-His; HHHHHH) (SEQ ID NO:32), hemagglutinin (HA; YPYDVPDYA) (SEQ ID NO: 33), glutathione-S-transferase (GST), or maltose-binding protein (MBP)) for use in purifying the polypeptides.

Optionally, a heterologous peptide tag comprising or consisting of SEQ ID NO: 28 (MRGSHHHHHHG-MASMTGGQQMGRDLYDDDDKDHPFT) can be linked or conjugated to any of the polypeptides described herein. As set forth above, a polyhistidine tag can be used It is understood that any polypeptide set forth herein comprising a polyhistidine tag is also provided as a polypeptide that does not comprise a polyhistidine tag (for example, SEQ ID NO: 32) at the N-terminus or the C-terminus of the polypeptide.

Heterologous polypeptides also include polypeptides (e.g., enzymes) that are useful as diagnostic or detectable markers, for example, luciferase, a fluorescent protein (e.g., green fluorescent protein (GFP)), or chloramphenicol acetyl transferase (CAT). Suitable radioactive labels include, e.g., $^{32}P$, $^{33}P$, $^{14}C$, $^{125}I$, $^{131}I$, $^{35}S$, and $^{3}H$. Suitable fluorescent labels include, without limitation, fluorescein, fluorescein isothiocyanate (FITC), green fluorescent protein (GFP). DyLight™ 488, phycoerythrin (PE), propidium iodide (PI), PerCP, PE-Alexa Fluor® 700, Cy5, allophycocyanin, and Cy7. Luminescent labels include, e.g., any of a variety of luminescent lanthanide (e.g., europium or terbium) chelates. For example, suitable europium chelates include the europium chelate of diethylene triamine pentaacetic acid (DTPA) or tetraazacyclododecane-1,4,7,10-tetraacetic acid (DOTA). Enzymatic labels include, e.g., alkaline phosphatase, CAT, luciferase, and horseradish peroxidase.

In some methods, the multi-epitope polypeptide comprises one or more TCR epitopes comprising the same flagellin amino acid sequence, for example, one, two, three, four, five, six or more TCR epitopes comprising the same flagellin sequence. In some methods, the multi-epitope polypeptide comprises two or more TCR epitopes wherein at least one of the TCR epitopes comprises a different flagellin sequence, for example, the polypeptide can comprise two, three, four, five, six or more TCR epitopes where at least one of the TCR epitopes comprises a different flagellin sequence as compared to the other TCR epitopes in the polypeptide. The TCR epitopes can be sequentially linked with or without linker sequence in between the TCR epitopes. Linker sequences of two, three, four, five, six or more amino acids can be used to link the TCR epitopes in any of the polypeptides described herein.

Provided herein is a polypeptide comprising one or more TCR epitopes selected from the group consisting of SEQ ID NO: 1, SEQ ID NO: 2, SEQ ID NO: 3, SEQ ID NO: 6. SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18. SEQ ID NO: 19, SEQ ID NO: 20, SEQ ID NO: 21, SEQ ID NO: 22, SEQ ID NO: 23. SEQ ID NO: 24, SEQ ID NO: 25, SEQ ID NO: 26, SEQ ID NO: 27, SEQ ID NO: 34, SEQ ID NO: 35, SEQ ID NO: 36 and SEQ ID NO: 37. Optionally, the polypeptide is not a full-length flagellin polypeptide sequence. Polypeptides having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity with any of the polypeptides described herein are also provided.

Nucleic acids encoding any of the polypeptides provided herein are also provided. The term nucleic acid or polynucleotide, refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260: 2605-2608 (1985); and Rossolini et al., Mol. Cell. Probes 8:91-98 (1994)). The term nucleic acid is used interchangeably with gene, cDNA, and mRNA encoded by a gene.

Vectors, including viral and non-viral vectors comprising any of the nucleic acid sequences provided herein are also provided. Cells comprising any of the nucleic acids described herein are also provided.

TABLE 1

Flagellin peptide TCR epitopes of human microbiota

| | AMINO | DOMAIN | Sequence | SEQ ID NOS |
|---|---|---|---|---|
| R. inulinivorans | Fla2 | 1-20 | MVVQHNMQAMNANRMLNVTT | 6 |
| | | 80-100 | LTEVHSMLQRMNELAVQASNG | 7 |
| | Fla5 | 1-15 | MVVQHNMTAANANRM | 8 |
| | Fla 5 | 81-99 | GETHSILQRMMNELATQAAN | 9 |
| R. hominis | Fla1 | 1-20 | MVVQHNLTAMNANRQLVGTTG | 10 |
| R. faecis | Fla1, Fla3 | 1-20 | MVVQHNMQAANANRMLGITS | 37 |
| | | 83-102 | VHSMLQRMNELAVQAASNGTNS | 38 |

TABLE 1-continued

| Flagellin peptide TCR epitopes of human microbiota | | | | |
|---|---|---|---|---|
| | AMINO DOMAIN | | Sequence | SEQ ID NOS |
| Eubacteria rectale (Agathobacter rectalis) | Fla1, Fla2 | 1-20 | MVVQHNMQAANANRMLNVTT | 11 |
| | Fla1, Fla3 | 80-100 | LTEVHSMLQRMNELATQSANG | 12 |
| | Fla2 | 80-100 | LTEVHSMLQRMNELAVQSSNG | 13 |
| | CARBOXY DOMAIN | | | |
| R. hominis | Fla1 | 243-268 | DMAEEMVEYSKNNILAQAGQSMLAQANQS | 14 |
| R. inulinivorans | Fla1 | 227-255 | | |
| R. intestinalis | Fla2 | 242-269 | | |
| R. inulinivorans | Fla2, Fla4 | 241-268 | MAEEMVNYSKNNILAAQAGQSMLAQANQ | 15 |
| Eubacteria rectale | Fla1 | 240-267 | | |
| R. faecis | Fla1, Fla3 | 243-270 | MAKEMVNYSKNNILAQAGQSMLAQAN | 16 |
| Eubacteria rectale | Fla2 | 241-268 | | |
| R. intestinalis | Fla1 | 198-230 | DMAEEMVTYSKNNILAQAGQSMLAQANQ | 17 |
| R. inulinivorans | Fla5 | | | |
| Flagellin peptide TCR epitopes of murine microbiota | | | | |
| Lachnospiraceae FlaX | FlaX | 1-20 | MVVQHNLRAMNSNRMLGITQ | 18 |
| | | 384-403 | SAQRSLLGAVQNRLEHTINN | 19 |
| Lachnospiraceae 14-2 | Fla1 | 81-100 | NEAHSILQRMNELAVQGAND | 20 |
| | | 354-375 | VEYSKNNILAQAGQSMLAQANQ | 21 |
| Lachnospiraceae A4 | Fla 4 | 1-20 | MVVQHNLRAMNSNRMLSITQ | 22 |
| | | 417-436 | DMATEMVKFSNSNILAQAGQ | 23 |
| Lachnospiraceae A4 | Fla3 | 1-19 | MVVQHNLRAMNANRMLGIT | 24 |
| | | 81-99 | TEVHDMLQRMNELAVKAAN | 25 |

The term identity, as used in the context of polynucleotide or polypeptide sequences, refers to a sequence that has at least 80% sequence identity to a reference sequence. Alternatively, percent identity can be any integer from 80% to 100%. Exemplary embodiments include at least: 80%, 85%, 90%, 95%, or 99% identity, as compared to a reference sequence using the programs described herein; preferably BLAST using standard parameters, as described below. One of skill will recognize that these values can be appropriately adjusted to determine corresponding identity of proteins encoded by two nucleotide sequences by taking into account codon degeneracy, amino acid similarity, reading frame positioning and the like.

For sequence comparison, typically one sequence acts as a reference sequence to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A comparison window, as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison may be conducted by the local homology algorithm of Smith and Waterman *Add. APL. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (*U.S.A.*) 85:2444 (1988), by computerized implementations of these algorithms (e.g., BLAST), or by manual alignment and visual inspection.

Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0)). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see. e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$.

In the methods provided herein, the polypeptide comprising one or more TCR epitopes, i.e., a multi-epitope polypeptide, activates flagellin-specific T cells. Activation of T cells refers to any treatment or manipulation of T cells which results in an increase (i.e., enhancement, upregulation, induction, stimulation) in the number, biological activity and/or survivability of the T cells. Therefore, increasing the activity of T cells can be accomplished by increasing the number of T cells in a subject (i.e., by causing the cells to proliferate/expand or by recruiting additional T cells to a site), increasing a type of T cell in a subject relative to another type of T cell, for example, increasing the number of regulatory T cells relative to one or more other types of T cells in the subject, by increasing the activation of T cells in an animal, by increasing biological activity of T cells (e.g., effector functions or other activities of the cell) in an animal and/or by increasing the ability of T cells to survive in a subject. In the methods provided herein, an increase in T cell activation can be an increase of at least about 10%, 20%, 30%, 50%, 60%, 70%, 80%, 90%, 100%, 200%, 300%, 400% or greater as compared to a control, for example, T cell activation in the absence of the polypeptide comprising one or more TCR epitopes.

As used herein, the phrase, T cell, refers to a lymphoid cell that expresses a T cell receptor molecule. T cells include human alpha beta (αβ) T cells and human gamma delta (γδ) T cells. T cells include, but are not limited to, naïve T cells, stimulated T cells, primary T cells (e.g., uncultured), helper T cells, cytotoxic T cells, memory T cells, regulatory T cells, natural killer T cells, combinations thereof, or sub-populations thereof. T cells can be $CD4^+$, $CD8^+$, or $CD4^+$ and $CD8^+$. T cells can also be $CD4^-$, $CD8^-$, or $CD4^-$ and $CD8^-$. T cells can be helper cells, for example helper cells of type $T_H1$, $T_H2$, $T_H3$, $T_H9$, $T_H17$, or $T_{FH}$. T cells can be cytotoxic T cells. Regulatory T cells can be $FOXP3^+$ or $FOXP3^-$. In some cases, the T cell is a $CD4^+CD25^{hi}CD127^{lo}$ regulatory T cell. In some cases, the T cell is a regulatory T cell selected from the group consisting of type 1 regulatory (Tr1), $T_H3$, CD8+CD28−, Treg17, and Qa-1 restricted T cells, or a combination or sub-population thereof. In some methods, the polypeptide comprising one or more TCR epitopes activates flagellin-specific $CD4^+$ T cells. In some methods, the polypeptide comprising one or more TCR epitopes activates flagellin-specific $CD4^+$ memory T cells.

In some embodiments, the agent that reduces flagellin antigen-specific memory T cells and/or increases regulatory T cells in the subject, increases regulatory T cells by activing regulatory T cells. In some embodiments, the agent that activates or increases regulatory T cells is a mutant IL-2 polypeptide, for example, SEQ ID NO: 29 (APTSSSTKKTQLQLEHLLLDLQMILNGINNYKNPKLTRMLTFKFYMPKKATELKHL QCLEEELKPLEEALNLAPSKNFHIRPRDLISDINVIVLELKGSETTFMCEYADETATIVE FLNR WITFSQSIISTLT) or SEQ ID NO: 30 (APTSSSTKKTQLQLEHLLLDLQMILNGINNYKNPKLTRMLTFKFYMPKKATELKHL QCLEEELKPLEEALNLAPSKNFHLRPRDLISDINVIVLELKGSETTFMCEYADETATIV EFINR WITFSQSIISTLT). Other exampled include mutant IL-2 polypeptide comprising one or more substitutions selected from the group consisting of aV69A, Q74P, L80I, N88D, L118I, and a C125S substitution. Non-limiting examples of mutant IL-2 polypeptides can be found in U.S. Pat. Nos. 10,174,092, 10,174,092, 9,580,486, 7,105,653, 9,616,105, and 9,428,567, all of which are incorporated in their entireties by this reference. In some embodiments, the IL-2 mutant polypeptide further comprises an Fc peptide. In some embodiments, the Fc peptide is at the C-terminus. In some embodiments, the Fc peptide is at the N-terminus. Examples of Fc peptides can be found in U.S. Pat. Nos. 10,174,091 and 10,174,092 (See, for example, SEQ ID NO: 8, SEQ ID NO: 9 or SEQ ID NO: 15 of U.S. Pat. No. 10,174,092). In some embodiments, the IL-2 mutant is administered with an another agent that increases regulatory T cells, for example, a metabolic inhibitor. In some embodiments, the IL-2 mutant is administered with an mTOR inhibitor, for example, rapamycin.

In some embodiments, the agent that reduces flagellin antigen-specific memory T cells or increases regulatory T cells in the subject is a metabolic inhibitor. In the methods provided herein the metabolic inhibitor can inactivate T cells that have been activated by contacting the T cells with the polypeptide comprising one or more TCR epitopes, for example, CD4+ $T_M$ cells. Inactivation of the microbiota-flagellin $T_M$ cells or inducing Treg cells via T cell receptor (TCR) stimulation and inhibition of mTORC results in a decrease of microbiota-reactive $T_M$ cells, an increase in Treg cells and/or an altered ratio of Treg/$T_E$ cells. In any of the methods provided herein, a decrease or reduction in memory T ($T_M$) cells, can be a reduction or decrease of at least 10%, as compared to a reference control level, or a decrease of least about 20%, or at least about 30%, or at least about 40%, or at least about 50%, or at least about 60%, or at least about 70%, or at least about 80%, or at least about 90%, or at least about 95%, or at least about 100%. A decrease or reduction in $T_M$ cells can also be a decrease or reduction in the biological activity of memory T ($T_M$) cells. In any of the methods provided herein, an increase in Treg cells can be an increase of at least about 10%, as compared to a reference control level, or an increase of least about 20%, or at least about 30%, or at least about 40%, or at least about 50%, or at least about 60%, or at least about 70%, or at least about 80%, or at least about 90%, or at least about 95%, or at least about 100%, or at least about 200%, or at least about 300%, or at least about 400%. In some methods, TCR stimulation, i.e., flagellin-specific T cell activation, and mTORC inhibition occur simultaneously. In other methods, mTORC inhibition occurs subsequent to flagellin-specific T cell activation.

In some methods, the metabolic inhibitor is an FK506-binding protein 12-rapamycin-associated protein 1 (mTOR) inhibitor. Examples of mTOR inhibitors include, but are not limited to rapamycin, sirolimus, temsirolimus, everolimus, ridaforolimus, dactolisib, BGT226, SF1126, PKI-587 and sapanisertib. In other methods, an ATPase inhibitor, for example, Bz423, a pro-apoptotic 1, 4 benzodiazepine, can be administered. In the methods provided herein, the polypeptide comprising one or more TCR epitopes can be administered to the subject simultaneously with the metabolic inhibitor or prior to or after administration of the metabolic inhibitor. In some methods, the polypeptide comprising one or more TCR epitopes and the metabolic inhibitor are administered simultaneously, or shortly after administration of the polypeptide that activates flagellin specific T cells so that the metabolic inhibitor can inactivate the recently activated T cells.

Any of the methods provided herein can further comprise administering a protein kinase AMP-activated catalytic subunit alpha 1 (AMPK) activator to the subject. Examples of AMPK activators include, but are not limited to, metformin, troglitazone, prioglitazone, rosiglitazone, resveratrol, quercetin, genistein, epigallocatechin gallate, berberine, curcumin, ginsenoside Rb1, α-lipoic acid and cryptotanshinone. The AMPK activator can be administered to the subject simultaneously with, prior to or after administration of the metabolic inhibitor. The AMPK activator can be administered to the subject simultaneously with, prior to or after administration of a polypeptide comprising one or more flagellin T-cell receptor (TCR) epitopes.

Any of the methods provided herein can be performed in conjunction with other therapies for inflammatory bowel disease (combination therapy). For example, a polypeptide comprising one or more flagellin T-cell receptor (TCR) epitopes, a metabolic inhibitor and/or an AMPK activator can be administered to a subject at the same time, prior to, or after, surgery, chemotherapy, immunotherapy, gene therapy, cell transplant therapy, genome editing therapy, or other pharmacotherapy.

As used herein, the term subject means a mammalian subject. The term subject can be used interchangeably with the term patient. Exemplary subjects include, but are not limited to humans, monkeys, dogs, cats, mice, rats, cows, horses, camels, goats and sheep. In some embodiments, the subject is a human. In some embodiments, the subject has or is suspected of having an inflammatory bowel disorder, for example, Crohn's disease or ulcerative colitis. Optionally, the subject is diagnosed with an inflammatory bowel disease or at risk for developing an inflammatory bowel disease, for example, Crohn's disease or ulcerative colitis. The subject can be a human with an inflammatory bowel disease, wherein the subject has an increased anti-flagellin response, as compared to a control. The subject can be a human with an inflammatory bowel disease, wherein the subject has an increased anti-Lachnospiraceae flagellin response, as compared to a control. The subject can be a human with an inflammatory bowel disease, wherein the subject has an increased anti-Cbir 1 flagellin response, as compared to a control. Exemplary controls include, but are not limited to, a subject that is in remission, a healthy subject or a control value. In some methods, the subject can be a human subject that can be suspected of having an inflammatory bowel disease that can be treated with a polypeptide comprising one or more flagellin TCR epitopes and a metabolic inhibitor.

Optionally, a subject can be tested for immune reactivity to one or more antigens, for example, microbiota peptide sequences (for example, microbiota flagellin antigens) to identify one or more antigens for which the subject has an increased response, as compared to a control. Once the one or more antigens are identified, a polypeptide comprising the one or more antigens can be administered to the subject. Any of the methods provided herein, can further comprise administering a polypeptide comprising one or more antigens for which the subject has an increased response to the subject. In some examples, the identified one or more antigens can be included in any of the polypeptides described herein, for example, in a polypeptide comprising one or more antigens selected from the group consisting of SEQ ID NO: 1, SEQ ID NO: 2, SEQ ID NO: 3, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26 and SEQ ID NO: 27. In some examples, the one or more antigens for which the subject has an increased response can be included in a polypeptide comprising SEQ ID NO: 4 or SEQ ID NO: 5.

Treating or treatment of any disease or disorder refers to ameliorating a disease or disorder that exists in a subject. The term ameliorating refers to any therapeutically beneficial result in the treatment of a disease state, e.g., an inflammatory bowel disease, lessening the severity or progression, promoting remission or durations of remission, or curing thereof. Thus, treating or treatment includes ameliorating at least one physical parameter or symptom. Treating or treatment includes modulating the disease or disorder, either physically (e.g., stabilization of a discernible symptom) or physiologically (e.g., stabilization of a physical parameter) or both. Treating or treatment includes delaying or preventing progression of an inflammatory bowel disease. Thus, in the disclosed methods, treatment can refer to a 10%, 20%, 30%, 40%, 50%, 60%, 70%, 80%, 90%, or 100% reduction in the severity of an established disease or condition or symptom of the disease or condition. For example, a method for treating an inflammatory bowel disease is considered to be a treatment if there is a 10% reduction in one or more symptoms of the autoimmune disorder (for example, digestive issues, abdominal pain, fatigue, skin problems, swollen glands, fever, etc.) in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, a relapse or flare is considered an exacerbation of the inflammatory bowel disease that causes new symptoms or worsening of previous symptoms. Subjects who achieve remission, or symptom free periods to initial treatment and then experience a recurrence are said to have had a relapse or flare of an inflammatory bowel disease. One or more relapses may occur days, months or years after the initial remission.

Administration

As used herein, administer or administration refers to the act of introducing, injecting or otherwise physically delivering a substance as it exists outside the body (e.g., a multi-epitope polypeptide and/or a metabolic inhibitor) into a subject, such as by mucosal, intradermal, intravenous, intramuscular, intrarectal, oral, subcutaneous delivery and/or any other method of physical delivery described herein or known in the art. When a disease, or a symptom thereof, is being treated, administration of the substance typically occurs after the onset of the disease or symptoms thereof. When a disease, or symptoms thereof, are being prevented, administration of the substance typically occurs before the onset of the disease or symptoms thereof.

The compositions are administered in a number of ways depending on whether local or systemic treatment is desired, and on the area to be treated. The compositions are administered via any of several routes of administration, including orally, parenterally, intramucosally, intravenously, intraperitoneally, intraventricularly, intramuscularly, intradermally, subcutaneously, intracavity or transdermally. Administration can be achieved by, e.g., topical administration, local infusion, injection, or by means of an implant. The implant can be of a porous, non-porous, or gelatinous material, including membranes, such as sialastic membranes, or fibers. The implant can be configured for sustained or periodic release of the composition to the subject. See, e.g., U.S. Patent Application Publication No. 20080241223; U.S. Pat. Nos. 5,501,856; 4,863,457; and 3,710,795; and European Patent Nos. EP488401 and EP 430539. The composition can be delivered to the subject by way of an implantable device based on, e.g., diffusive, erodible, or convective systems, osmotic pumps, biodegradable implants, electrodiffusion systems, electroosmosis systems, vapor pressure pumps, electrolytic pumps, effervescent pumps, piezoelectric pumps, erosion-based systems, or electromechanical systems. In some embodiments, the multi-epitope polypeptide and the metabolic inhibitor are therapeutically delivered to a subject by way of local administration. Effective doses for any of the administration methods described herein can be extrapolated from dose-response curves derived from in vitro or animal model test systems.

As used herein, the term therapeutically effective amount or effective amount refers to an amount of a polypeptide comprising one or more flagellin TCR epitopes, a metabolic inhibitor or AMPK activator that, when administered to a subject, is effective to treat a disease or disorder either by one dose or over the course of multiple doses. A suitable dose can depend on a variety of factors including the particular polypeptide used and whether it is used concomitantly with other therapeutic agents. Other factors affecting the dose administered to the subject include, e.g., the type or severity of the inflammatory bowel disease. For example, a subject having ulcerative colitis may require administration of a different dosage of a multi-epitope polypeptide a metabolic inhibitor and/or an AMPK activator than a subject with Crohn's disease. Other factors can include, e.g., other medical disorders concurrently or previously affecting the subject, the general health of the subject, the genetic disposition of the subject, diet, time of administration, rate of excretion, drug combination, and any other additional therapeutics that are administered to the subject. It should also be understood that a specific dosage and treatment regimen for any particular subject also depends upon the judgment of the treating medical practitioner. A therapeutically effective amount is also one in which any toxic or detrimental effects of the composition are outweighed by the therapeutically beneficial effects.

A pharmaceutical composition can include a therapeutically effective amount of any multi-epitope polypeptide, metabolic inhibitor and/or AMPK activator described herein. In some embodiments, the pharmaceutical composition can further comprise a carrier. Such effective amounts can be readily determined by one of ordinary skill in the art as described above. Considerations include the effect of the administered multi-epitope polypeptide, or the combinatorial effect of the multi-epitope polypeptide with one or more additional active agents, if more than one agent is used in or with the pharmaceutical composition. Cell culture assays and animal studies can be used in formulating a range of dosage for use in humans.

The term carrier means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject. Such pharmaceutically acceptable carriers include sterile biocompatible pharmaceutical carriers, including, but not limited to, saline, buffered saline, artificial cerebral spinal fluid, dextrose, and water.

Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the agent described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected agent without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material known in the art for use in pharmaceutical formulations. The choice of a carrier for use in a composition will depend upon the intended route of administration for the composition. The preparation of pharmaceutically acceptable carriers and formulations containing these materials is described in, e.g., Remington: The Science and Practice of Pharmacy, 22nd edition, Loyd V. Allen et al, editors, Pharmaceutical Press (2012).

Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, New Jersey), polyethylene glycol (PEG), and PLURONICS™ (BASF; Florham Park, NJ).

Compositions containing the agent(s) described herein suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof are admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

The agents described herein can be incorporated into pharmaceutical compositions which allow for immediate release or delivery of those agents to a mammal. The agents described herein can also be incorporated into pharmaceutical compositions which allow for modified release, for example, delayed release or extended release (for example, sustained release or controlled release) of those agents to a mammal for a period of several days, several weeks, or a month or more. Such formulations are described, for example, in U.S. Pat. Nos. 5,968,895 and 6,180,608 and are otherwise known in the art. Any pharmaceutically-acceptable, delayed release or sustained-release formulation known in the art is contemplated.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, such as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

In some examples, a nucleic acid is employed, for example, a nucleic acid encoding encoding a polypeptide comprising one or more flagellin T-cell receptor (TCR) epitopes and/or a nucleic acid encoding the mutant IL-2 polpeptide is administered to the subject. The nucleic acid can be delivered with a carrier. Nucleic acid carriers include, polyethylene glycol (PEG), PEG-liposomes, branched carriers composed of histidine and lysine (HK polymers), chitosan-thiamine pyrophosphate carriers, surfactants, nanochitosan carriers, and D5W solution. The present disclosure includes all forms of nucleic acid delivery, including synthetic nucleic acids, naked DNA, plasmid and viral delivery, integrated into the genome or not.

As mentioned above, vector delivery can be via a viral system, such as a retroviral vector system which can package a recombinant retroviral genome (see e.g., Pastan et al., Proc. Natl. Acad. Sci. U.S.A. 85:4486, 1988; Miller et al., Mol. Cell. Biol. 6:2895, 1986). The exact method is, of course, not limited to the use of retroviral vectors. Other techniques are widely available for this procedure including the use of adenoviral vectors (Mitani et al., Hum. Gene Ther. 5:941-948, 1994), adeno-associated viral (AAV) vectors (Goodman et al., Blood 84:1492-1500, 1994), lentiviral vectors (Naidini et al., Science 272:263-267, 1996), and pseudotyped retroviral vectors (Agrawal et al., Exper. Hematol. 24:738-747, 1996). The nucleic acid can also be encapsulated in a nanoparticle or chemically conjugated to a carrier. For example, the nucleic acid can be chemically conjugated to a cell or a tissue-targeting ligand, such as an antibody or a ligand for a cell-surface receptor to target nucleic acid to specific cell types or tissue environments.

Physical transduction techniques can also be used, such as liposome delivery and receptor-mediated and other endocytosis mechanisms (see, for example, Schwartzenberger et al., Blood 87:472-478, 1996) to name a few examples. Nucleic acid delivery can local or systemic, via any of the delivery methods described herein, for example, and not to be limiting, via oral, parenteral, intramucosal, intravenous, intraperitoneal, intraventricular, intramuscular, subcutaneous, intracavity or transdermal administration.

Disclosed are materials, compositions, and ingredients that can be used for, can be used in conjunction with or can be used in preparation for the disclosed embodiments. These and other materials are disclosed herein, and it is understood that when combinations, subsets, interactions, groups, etc. of these materials are disclosed that while specific reference of each various individual and collective combinations and permutations of these compositions may not be explicitly disclosed, each is specifically contemplated and described herein. For example, if a method is disclosed and discussed, and a number of modifications that can be made to a number of molecules included in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Examples

Microbiota Antigen CD4 T Memory Cells $T_M$

CD4+ T cell effectors mediate colitis in mouse models. These effectors, for example, Th1 and Th17 are short-lived. The CD4+ T cell memory pool is a reservoir of chronicity and regenerating T effector cells. CD4+ $T_M$ cells are widely distributed in CBir1 TCR Tg mice (FIG. 1). Flagellin specific T cells can cause murine colitis, mainly Th17 mediated. Anti-CBir1 was detected in 50% of Crohn's patients and in multiple mouse models. The presence of anti-Cbir1 in CD patients is associated with small bowel (SB) involvement, fibrostenosis and internal perforating phenotypes, independent of anti-*Saccharomyces cerevisiae* antibodies (ASCA), anti-12 antibodies and anti-OmpC antibodies. A subset of Crohn's patients has broad IgG reactivity to microbiota flagellins (FIG. 2). Flagellins have promiscuous T cell receptor epitopes. Therefore, whether microbiota flagellins contain epitope peptides that are broadly reactive in humans and can stimulate both $T_M$ and Tregs across a population of patients with Crohn's disease was studied. Peptides predicted to bind to 8 or more HLA-DRB1 molecules and to mouse H-$2^b$ or H-$2^d$ were studied. Thirty predicted flagellin epitopes were tested for binding to the four most common HLA-DR dimers (HLA-DR3, HLA-DR7, HLA-DR11 and HLA-DR15). All predicted flagellin epitopes bound at least one of the four HLA-DR dimers, and twenty of the predicted epitopes bound two or more. Table 2 shows the binding of flagellin peptides to HLA-DR.

TABLE 2

| | EC50 Ratio* | | | |
|---|---|---|---|---|
| | DR0301 | DR0701 | DR1101 | DR1501 |
| CBir1 p456-475 | — | 3.7 | — | 0.32 |
| R. Intest. Fla1 p408-427 | 55 | 5.0 | 58 | 4.1 |
| FlaX p1-20 | — | — | — | 0.33 |
| A4 Fla3 p1-19 | — | 2.5 | 0.2 | 0.32 |
| E. rectale Fla1 p445-464 | — | — | 0.3 | 4.5 |

*<20 = high affinity 20-100 +moderate affinity
All 30 peptides bound at least one of the four HLA-DRs
19/20 peptides bound 2 or more of the four HLA-DRs Table 3 shows predicted TCR epitopes for CBir-1. Polypeptides comprising any of these peptides can be used in the methods provided here. Cbir-1 polypeptide (#1-17) is SEQ ID NO: 34. Cbir-1 polypeptide (#411-426) is SEQ ID NO: 35. Cbir-1 polypeptide (#456-475) is SEQ ID NO: 36.

TABLE 3

| CBir-1 | | HLA-DRB1* | | | | | Percentile rank† | | | | H-2 |
|---|---|---|---|---|---|---|---|---|---|---|---|
| peptide # | Sequence | 01:01 | 03:01 | 04:01 | 04:05 | 07:01 | 08:02 | 09:01 | 11:01 | 13:01 | 15:01 | b/d |
| 1-17 | MVVQHNICAMNSARMLG | 4.8 | 4.1 | 0.2 | 2.7 | 5.1 | 8.6 | 3.8 | 4.6 | 3.1 | 2.3 | + |
| 411-426 | AGAIKKVSTORSALGA | 9.8 | 6.0 | 2.6 | 7.2 | 1.9 | 0.1 | — | 4.7 | 19.5 | 16.4 | + |
| 466-475 | MATEMVKYSNANILSQAGQ | 17.0 | 4.6 | 2.5 | 7.0 | 0.8 | 0.7 | 1.6 | 3.9 | 0.2 | 0.8 | + |

†Percentile rank: the lower the rank the better the binding of the peptide to HLA-DR;
Scores above 20 percentile considered as non-binding;
+, peptide predicted to bind with high affinity to either H-$2^b$ or H-$2^d$ T cells undergo reprogramming as they differentiate. Proliferating T cells have to regenerate the entire cell (proteins, lipids, nucleotides) in about 1 day. Proliferating T cells use aerobic glycolysis for anabolic regeneration. mTOR kinase regulates anabolic cell metabolism. mTOR and AMPK are key regulator for cell metabolism.

Figure 3:
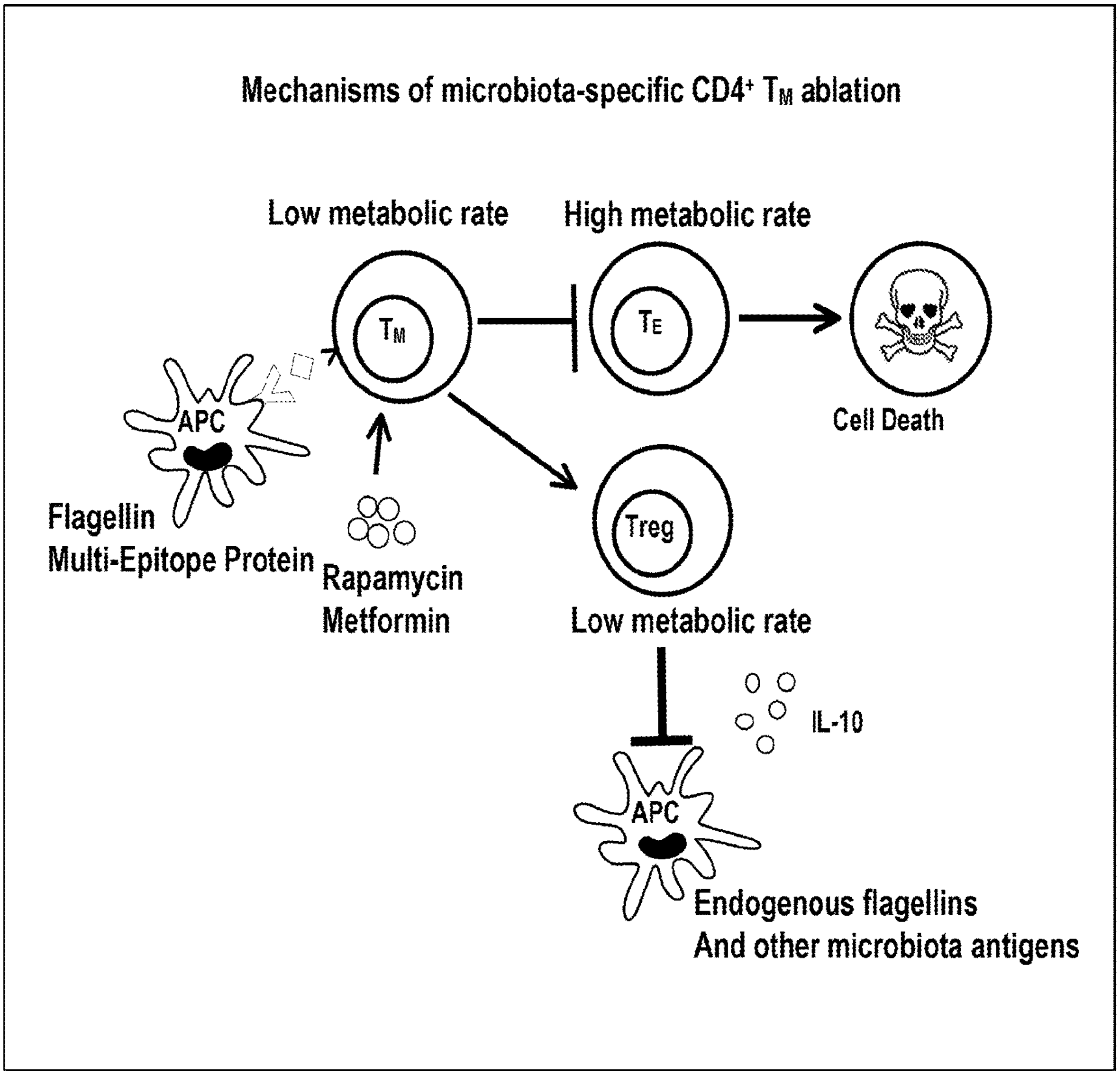
FIG. 3 is a schematic of a mechanism for ablating $CD4^+$ $T_M$ cells by administering a polypeptide comprising one or more flagellin TCR epitopes and a metabolic inhibitor to a subject. Inactivation of microbiota-flagellin specific $T_M$ cells or inducing Treg cells via T cell receptor stimulation and inhibition of mTORC results in the ablation of microbiota-reactive $T_M$ cells and an altered ratio of Treg/effector T ($T_E$) cells.

It was hypothesized that inactivating the microbiota-flagellin $T_M$ cells or transforming them into Treg cells via simultaneous T cell receptor (TCR) stimulation and inhibition of mTORC would result in the ablation of microbiota-reactive TM cells and an altered ratio of Treg/TE. A model for this process is shown in FIG. 3.

Figure 4A:
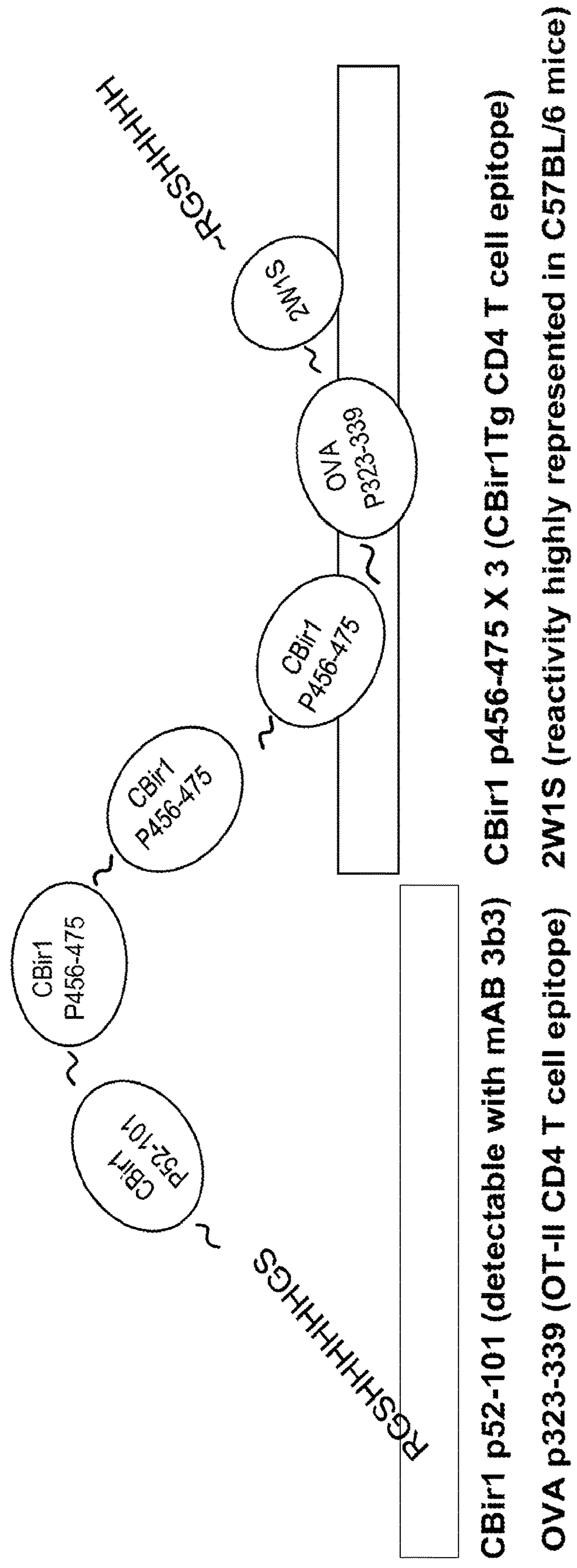
FIGS. 4A-4B show the structure and validation of a multi-epitope peptide (MEP1). (A) MEP1 is a 162 amino acid long peptide including 3 repeats of a CBir1Tg $CD4^+$ T cell epitope and 1 repeat of OT-II $CD4^+$ T cell epitope. (B) CBir1Tg $CD4^+$ T cells were isolated from the spleen and labeled with (5(6)-Carboxyfluorescein N-hydroxysuccinimidyl ester (CFSE). After 90 hrs in culture with irradiated APCs isolated from C57BL/6 mice plus MEP1 or CBir1 p456-475, at indicated concentrations, CBir1Tg $CD4^+$ T cell proliferation was determined with FACS analysis.
Figure 4B:
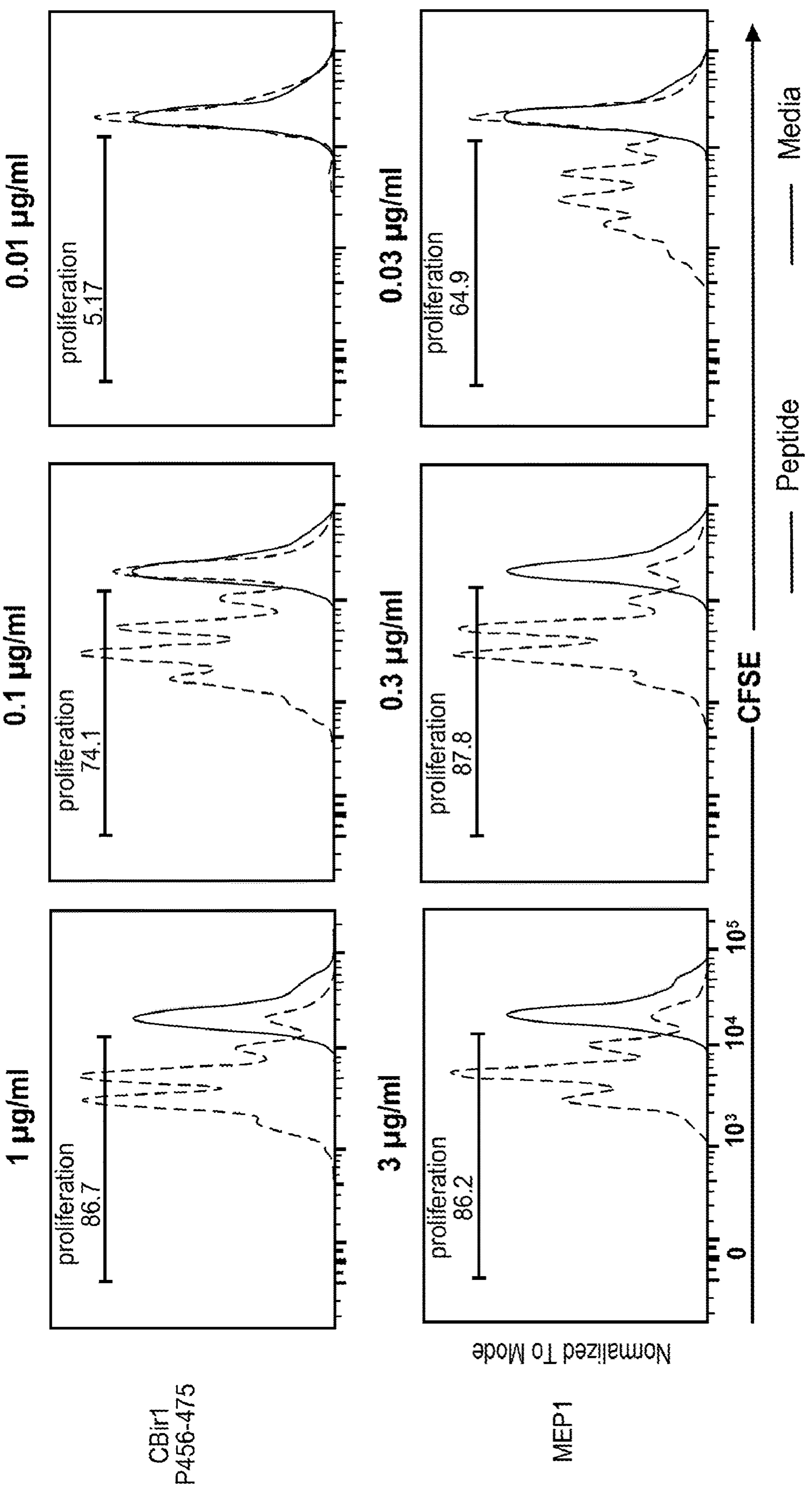
Figures 5A, 5B, 5C, 5D:
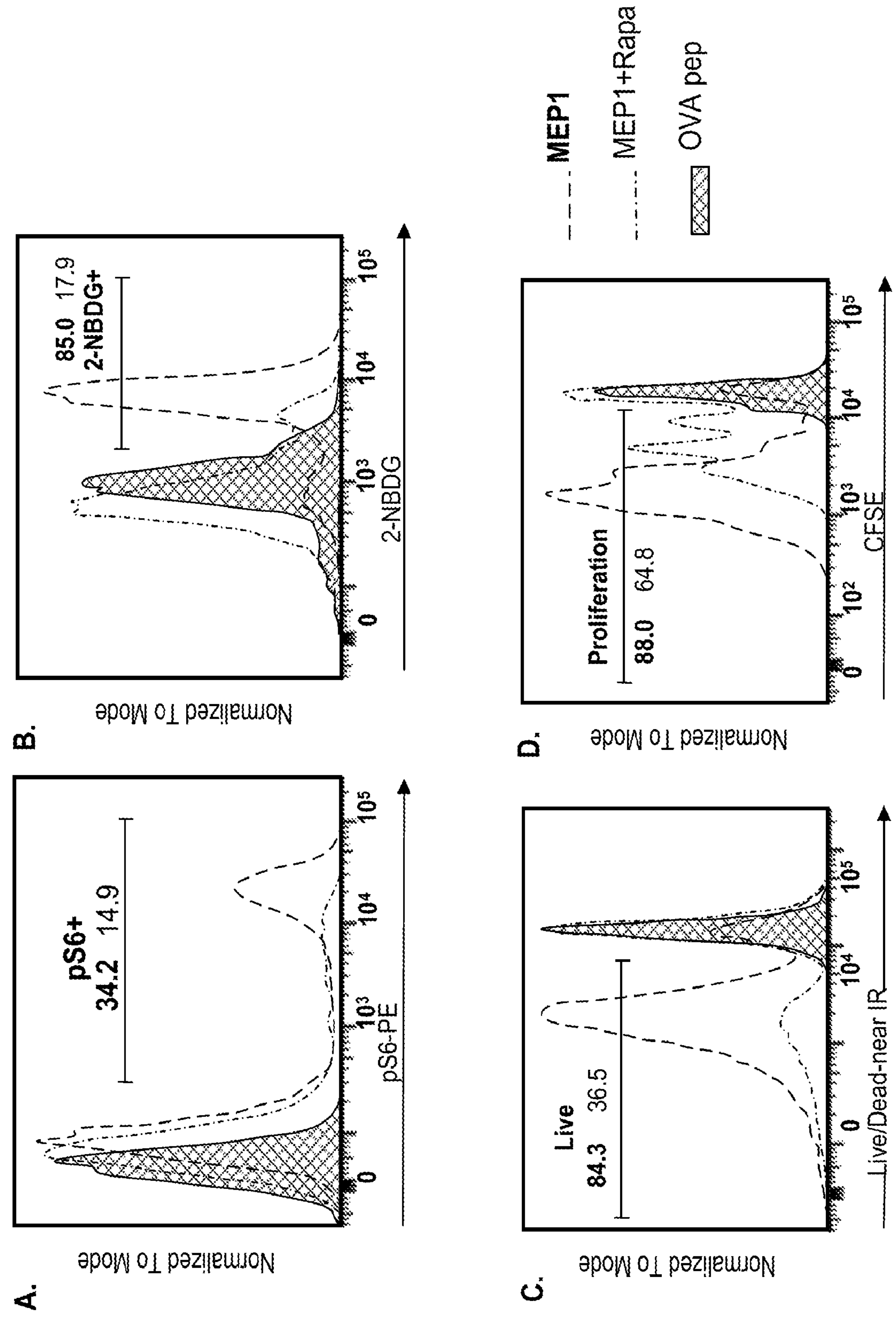
FIGS. 5A-5P show that rapamycin inhibits microbiota-specific $CD4^+$ T cell activation and proliferation through metabolic targeting in vitro, and generates suppressive Treg cells. CBir1Tg $CD4^+$CD44-naïve T cells were isolated from the spleen and co-cultured with irradiated antigen-presenting-cells (APCs) isolated from C57BL/6 mice, in the presence of 1 μg/ml of MEP1 with (blue) or without (red) 100 nM rapamycin. Phosphorylation of S6K in CBir1Tg $CD4^+$ T cells was examined after 20 hrs of stimulation. CBir1Tg $CD4^+$ T cell viability, uptake of fluorescent glucose analog 2-NBDG, proliferation, and Treg induction were determined with FACS after 90 hrs of co-culture. OVA p323-339 stimulation was used as a negative control (grey). Representative flow plots are shown in (A-D, and I), and statistics of 3 replicated experiments are shown in (E-H, and J). For in vitro and in vivo suppression assays, naïve CD4+ cells were isolated from CBir1Tg·Foxp3gfp spleen and cultured with MEP1 and rapamycin for 6 days for Treg induction. Then live $CD4^+CD25^+GFP^+$ Treg cells were sorted with flow cytometry as CBir1Tg iTreg Rapa. Live $CD4^+CD25^+GFP^+$ cells freshly isolated from naïve CBir1Tg·Foxp3gfp spleen were used as control (CBir1Tg tTreg) for suppression assay in vitro. CFSE labeled responder CD4+CD44-(Tn) cells were isolated from congenic CBir1Tg or C57BL/6 mouse and co-cultured with indicated ratios of CBir1Tg Treg cells in the presence of 1 μg/ml MEP1 or anti-mouse-CD3 and APCs for 3.5 days. Representative graphs of antigen-specific and bystander suppression are shown in (K and M), respectively, and accumulated percentage of suppression are shown in (L and N). For in vivo suppression, CFSE labeled responder Tn cells (CBir1Tg or OT-II Tg) were co-transferred with CBir1Tg iTreg Rapa cells or naïve CBir1Tg CD4+ cells (Ctrl) into congenic C57BL/6 recipients at 1:1 ratio. Recipient mice were then challenged i.p. with 30 μg CBir1 flagellin for antigen-specific suppression or 10 μg MEP1 for bystander suppression, and the proliferation of responder cells post 6 days of challenge are shown in (O and P), respectively.
Figures 5E, 5F, 5G, 5H:
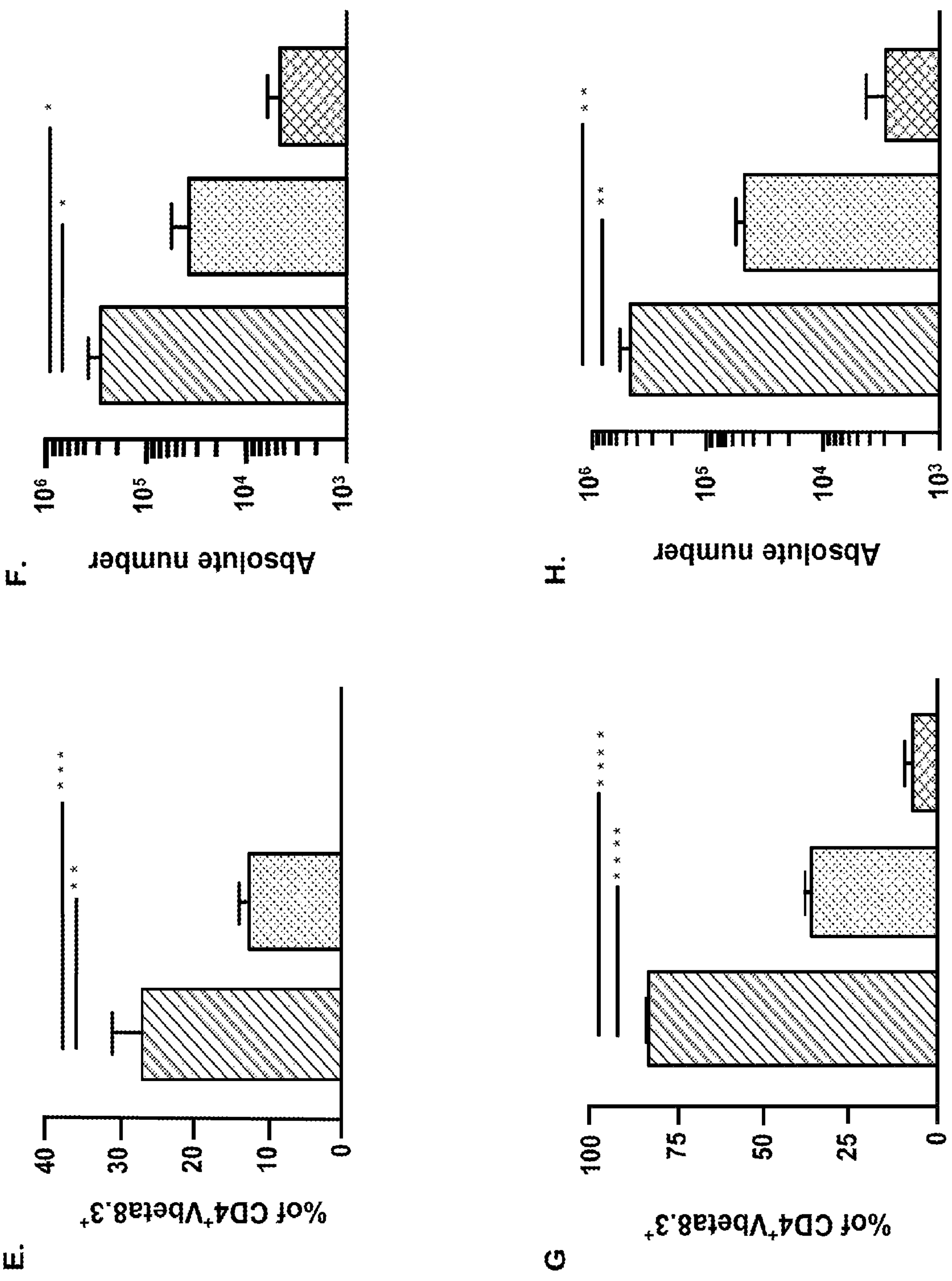

Rapamycin Inhibits Microbiota-Specific CD4+ Naïve T Cell Activation and Proliferation Through Metabolic Targeting In Vitro To perform the studies described herein, a multi-epitope-peptide-1 (MEP1) construct, which included three repeats of CBir1 TCR Tg CD4+ T cell epitope (CBir1 p456-479), and one repeat of OT-II Tg CD4+ T cell epitope (OVA p323-339 (ISQAVHAAHAEINEAGR) (SEQ ID NO. 2), was engineered. Dose response comparisons with corresponding peptides confirmed that antigen presenting cells (APCs) were able to process and present MEP1 at a comparable, or even higher level, as compared to single peptides (FIGS. 4A and 4B). Then, whether rapamycin has any impact on CD4+ naïve T cell metabolism and function, when it is simultaneously applied upon cognate antigen encounter, was tested. In the presence of 100 nM rapamycin, the phosphorylation of mTORC's main downstream target S6 kinase (S6K) resulted in roughly 60% reduction when CBir1Tg·CD4+ CD44− naïve T cells were co-cultured with irradiated APCs and MEP1 after 20 hrs (FIGS. 5A and 5E). Correspondingly, after 90 hrs of co-culture, rapamycin treated CD4+ T cells had significantly compromised capacity for glucose metabolism, as assessed by the uptake of fluorescent glucose analog 2-NBDG (FIGS. 5B and 5F). Rapamycin also led to dramatic CBir1Tg naïve CD4+ T cell death and roughly 10-fold reduction of cell proliferation in the presence of cognate antigen MEP1 (FIGS. 5C-D and 5G-H). Of note, rapamycin has to be present at the same time as antigen encounter to achieve all of the inhibitory effects, thus demonstrating that metabolic inhibition during cell activation is a viable strategy. These results indicate that simultaneous application of rapamycin during CD4+ T cell initial cognate antigen encounter blocks the major metabolic fuel for cell activation and proliferation, in specific glucose metabolism, thus resulting in drastic antigen-specific T cell killing instead of expansion.

Figures 5I, 5J:
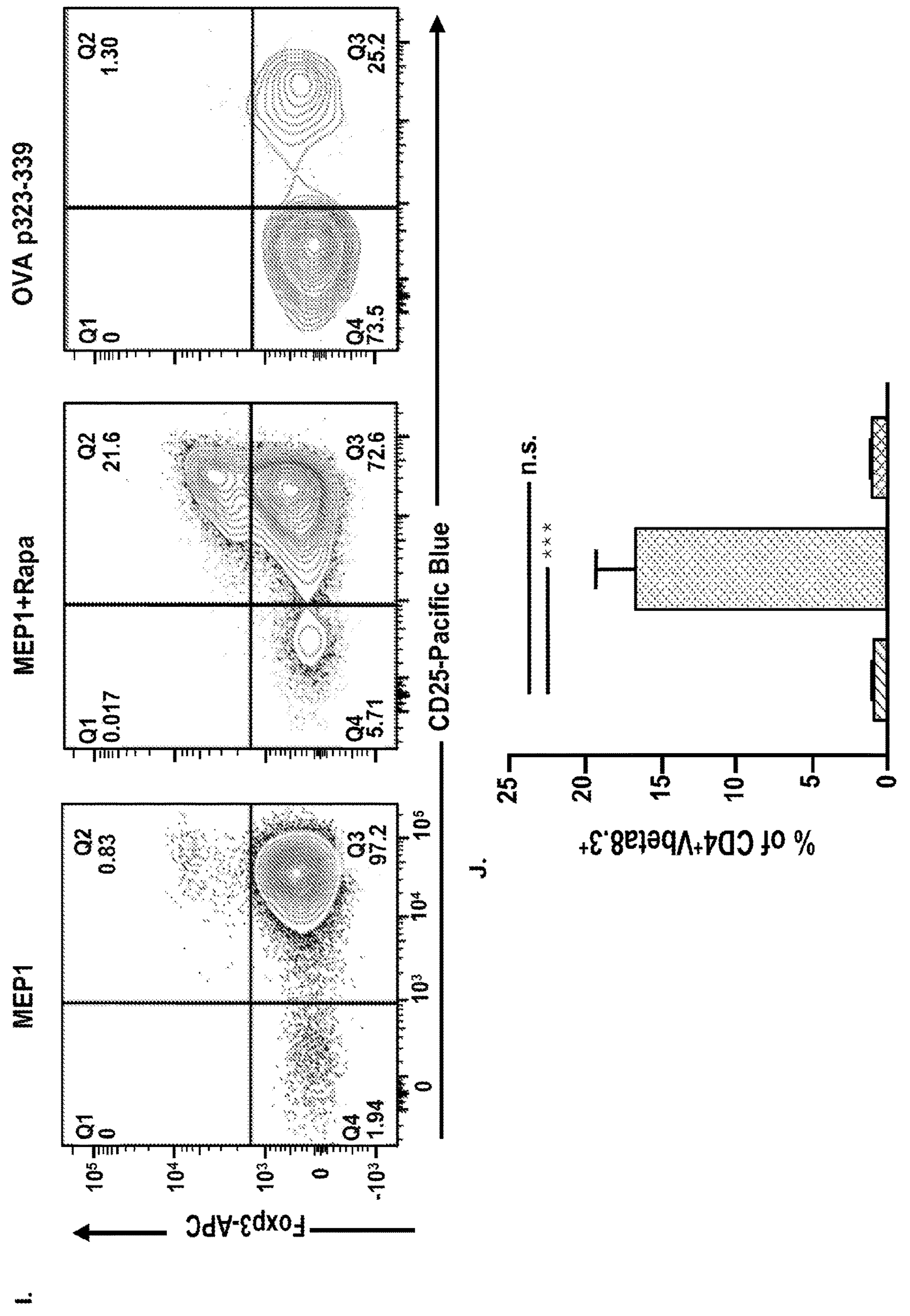
Figure 5K:
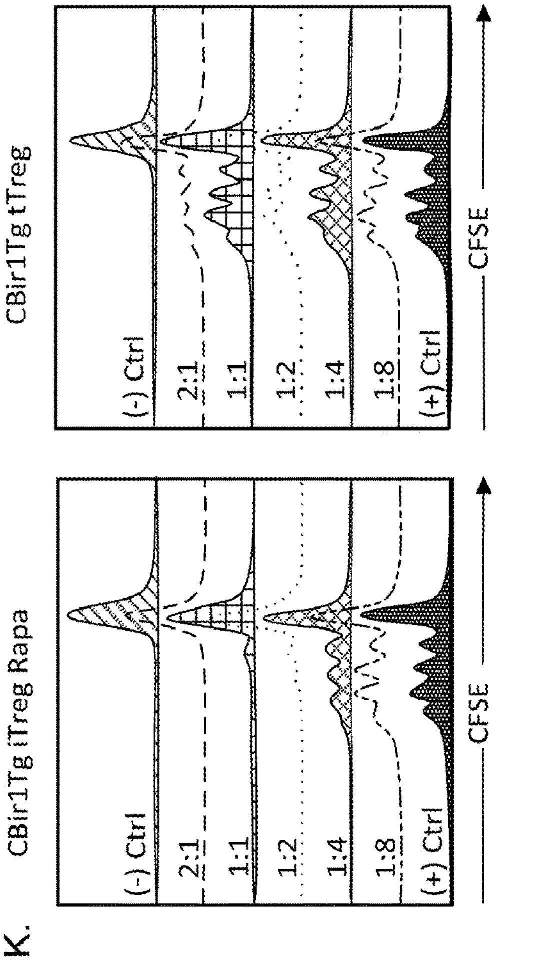
Figure 5L:
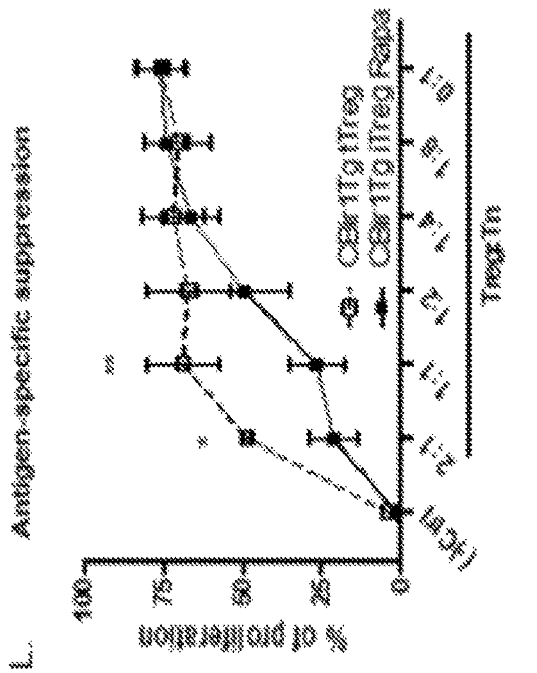
Figure 5M:
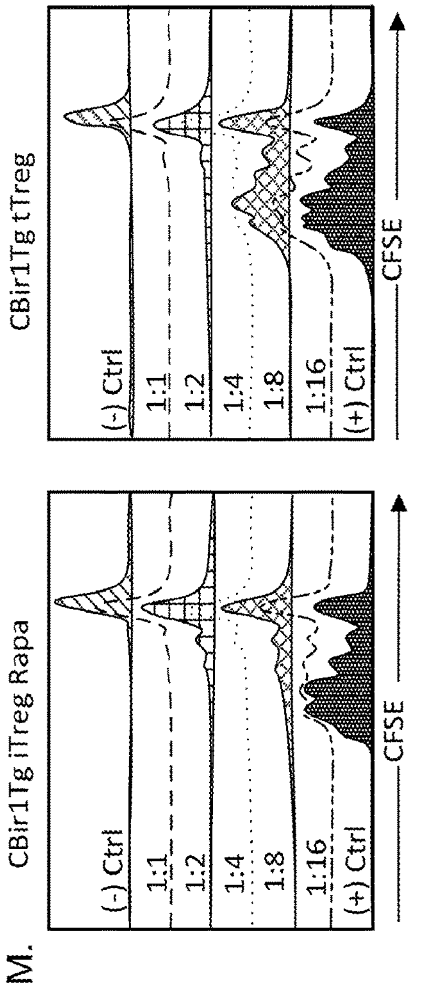
Figure 5N:
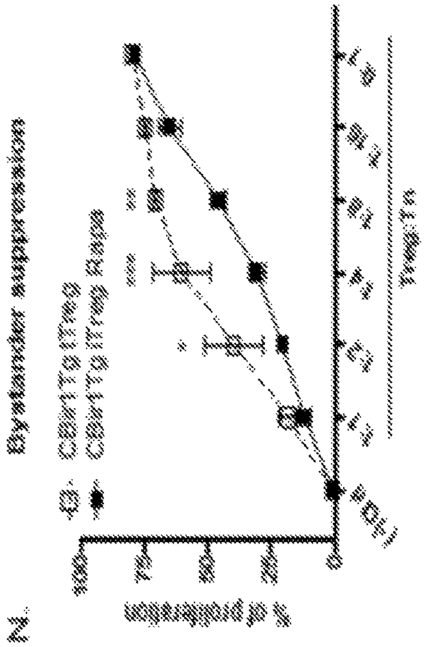

Rapamycin Promotes Microbiota-Specific Treg Development, with Enhanced Suppressive Function In Vitro and In Vivo Unlike activated CD4+ T cells. Treg cells mainly engage fatty acid oxidation as their energy source, and maintain a low level of metabolism, which is comparable to naïve $CD4^+$ cells. Thus, rapamycin has minimum impact on Treg metabolism, and in fact, rapamycin promotes substantial Treg differentiation. Compared to cells stimulated with MEP1 alone, CBir1Tg naïve $CD4^+$ T cells co-cultured with MEP1 and rapamycin for 96 hrs had a 20-fold increase of Treg cells in percentage (FIGS. 5I and 5J). To test if rapamycin-induced Treg cells are functionally suppressive in vitro and in vivo, naïve $CD4^+$ T cells isolated from CBir1Tg·Foxp3gfp mice were used, so that $GFP^+CD4^+CD25^+$ Treg cells could be sorted out after induction with MEP1 and rapamycin for 5 days (CBir1Tg iTreg Rapa). GFP+CD4+CD25+ cells freshly isolated from these mice were used as control Tregs (CBir1Tg tTreg) for an in vitro suppression assay. Naïve $CD4^+$ T cells isolated from congenic CBir1Tg or C57BL/6 mice were labelled with proliferation dye and stimulated with CBir1 p456-479 or anti-CD3, respectively, in the presence of the indicated ratios of rapamycin-induced Tregs or fresh ex vivo Tregs, to test their response under antigen-specific (FIGS. 5K and 5L) or bystander (FIGS. 5M and 5N) suppression. In both manners, it was found that rapamycin-induced Tregs strongly suppressed the proliferation of responder cells, and they showed a better suppression than fresh isolated Treg cells. Rapamycin-induced Treg cells were also able to provide antigen-specific and bystander suppressions in vivo.

Figure 5O:
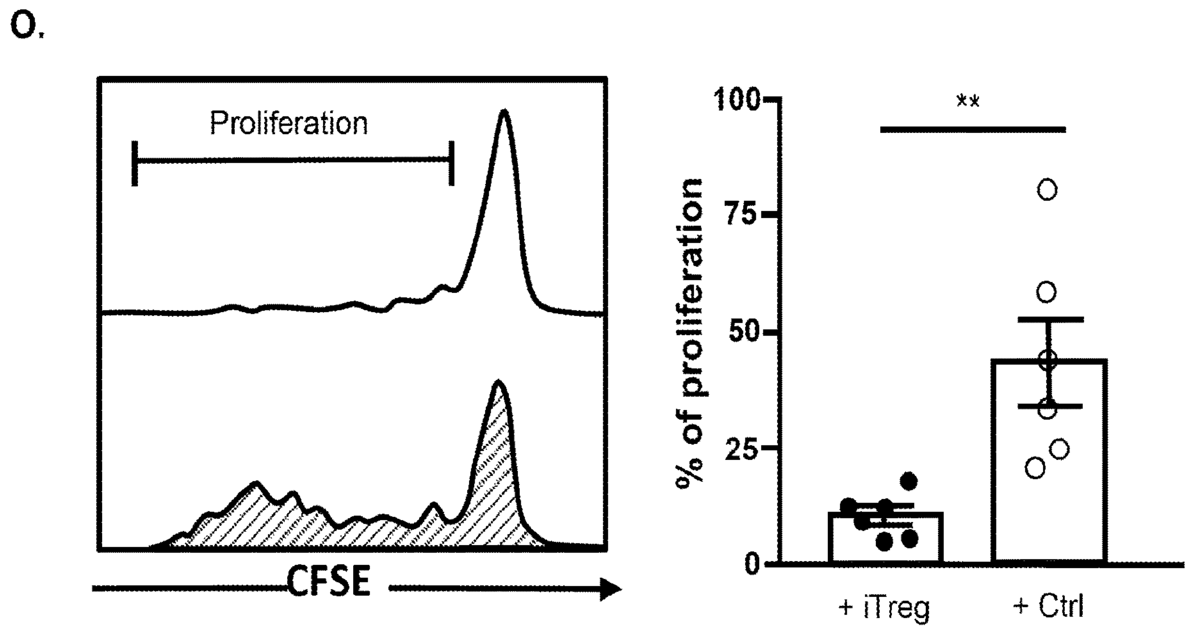
Figure 5P:
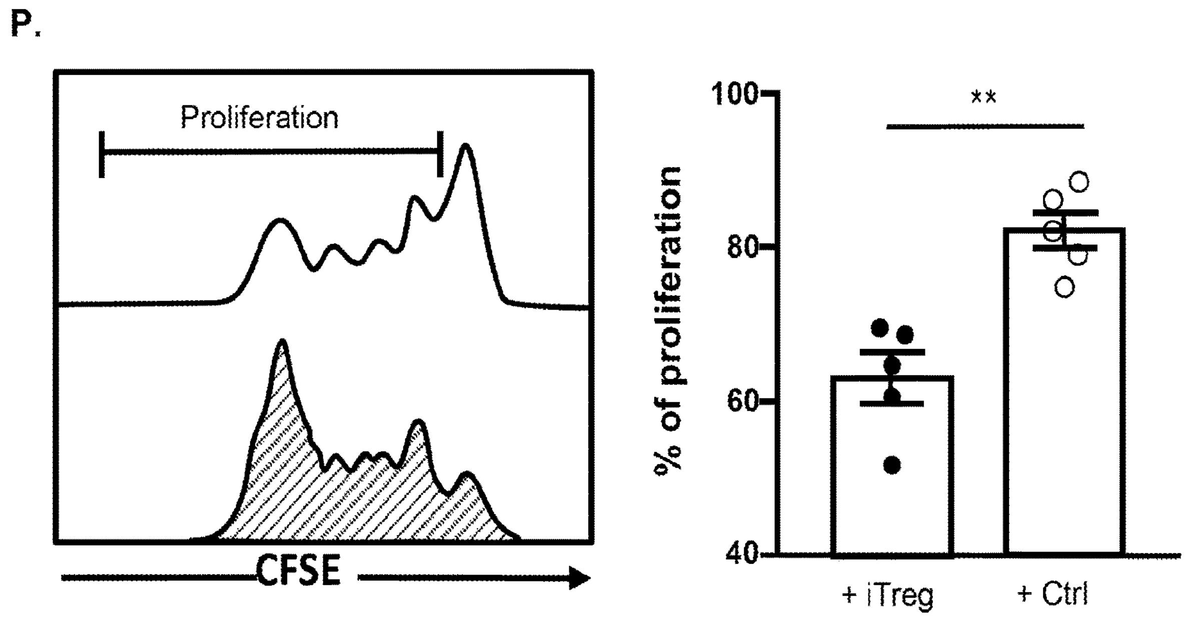

Equal amounts of CBir1Tg iTreg Rapa and CFSE labelled congenic naïve CD4+ responder cells (CBir1Tg or OT-II) were co-transferred into C57BL/6 mice, and the recipient mice were challenged with CBir1 p456-479 or MEP1, respectively. Mice transferred with CBir1Tg naïve CD4+ T cells plus responder cells, that received the same challenge, served as the corresponding control group. The proliferation of responder cells was inhibited in both manners when CBir1Tg iTreg Rapa cells were present (FIGS. 5O and 5P). These data showed that rapamycin favors the induction of phenotypic and functional Treg differentiation in addition to metabolic inhibition of other helper T cell subsets, thus providing the potential for both antigen-specific and bystander suppression of other responding CD4+ T cells.

Figure 6A:
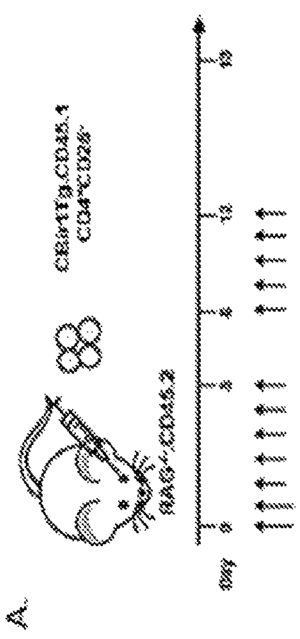
FIGS. 6A-6G show that simultaneous rapamycin treatment with peripheral antigen activation prevents the development of naïve CD4+ T cell mediated colitis in immunocompromised mice. Strategy of adoptive transfer and colitis induction is shown in (A). Rag−/− mice were transferred with $1\times10^6$ CD4+CD25-naïve T cells isolated from the spleen of CBir1Tg mice, followed by 5 μg of MEP i.v. injection on Day 1. Recipient mice were then treated with rapamycin (1 μg/g/day) or vehicle alone (0.2% CMC) on days 1-5 and days 8-12. Rag−/− mice receiving CBir1Tg CD4+CD25− cells without MEP1 stimulation served as colitic controls. Weight loss of recipient mice are shown in (B). Mice were sacrificed on day 18, when cecum and colon tissue were collected for histological analysis. Representative microscopic views of murine distal colon in each group are shown in (C), and histology severity scores are shown in (D). Colonic lamina propria cells were isolated from the recipient mice upon sacrifice for analyses of $CD4^+$ $T_E$ cell composition, and the absolute numbers of total CD4, Th1 and Th17 of transferred CBir1Tg cells in each group are shown in (E-G).
Figure 6B:
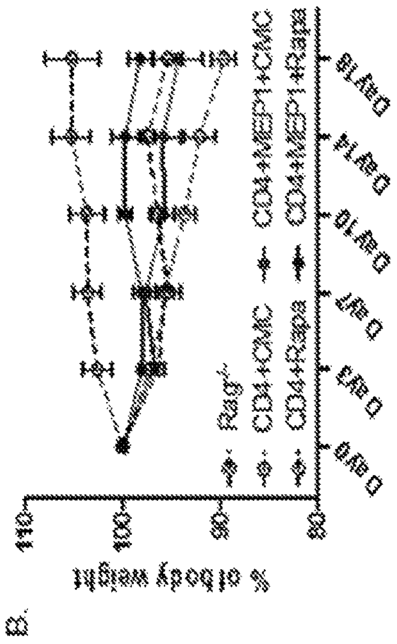
Figure 6C:
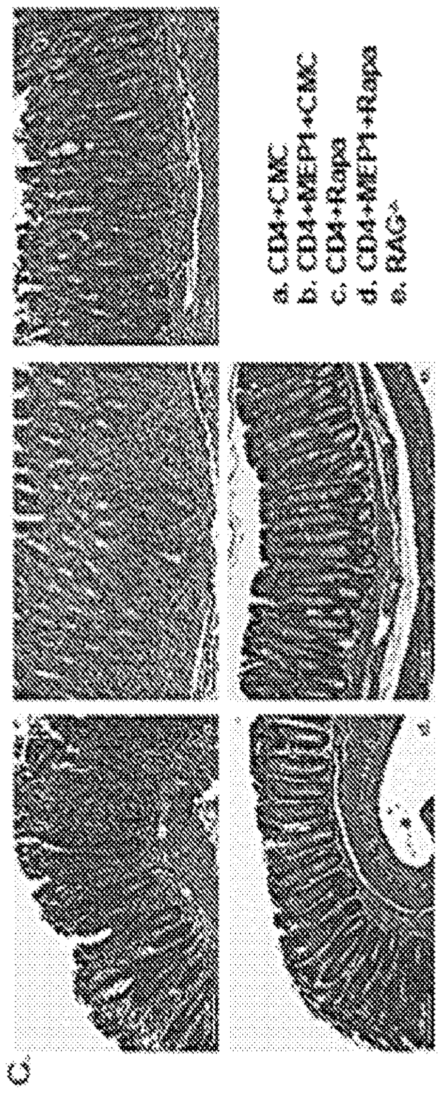
Figure 6E:
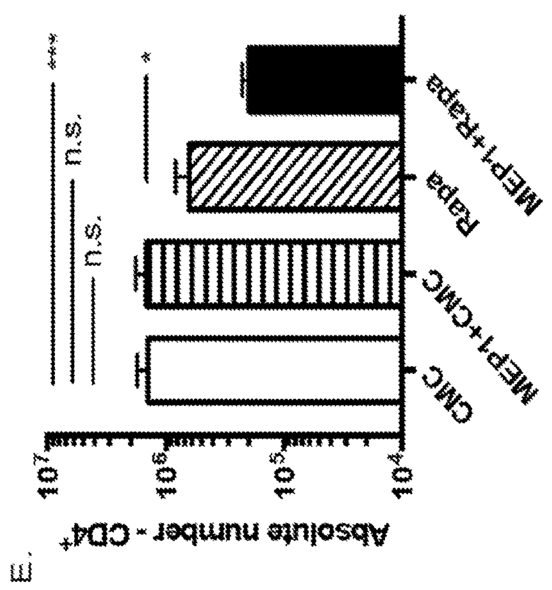
Figure 6G:
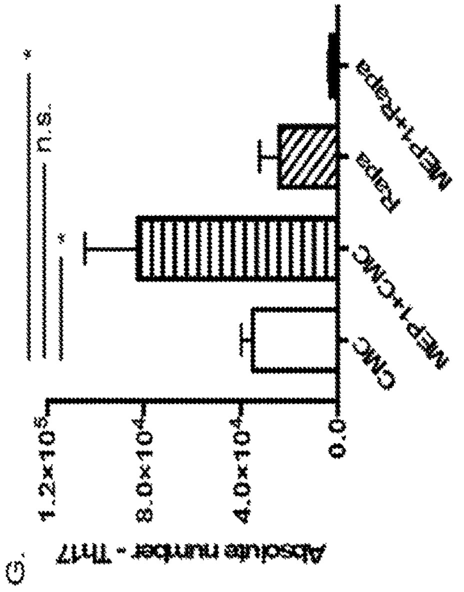
Figure 6D:
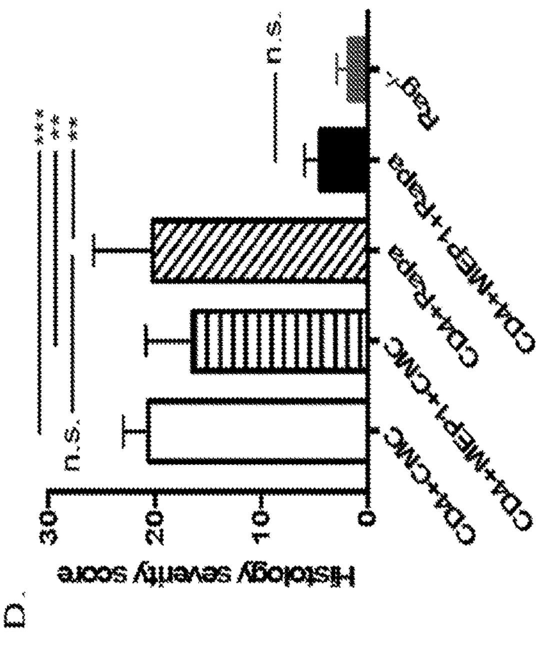
Figure 6F:
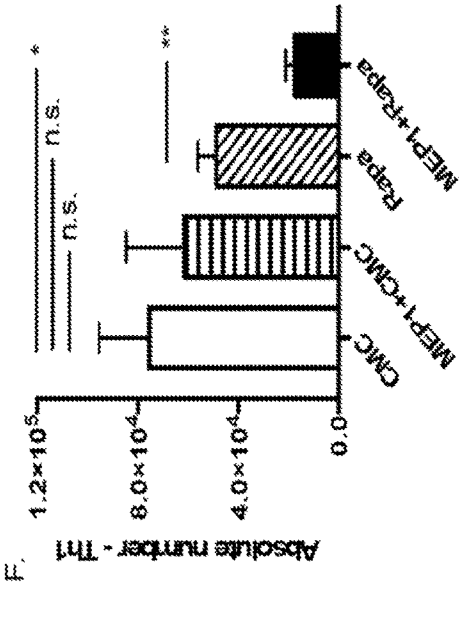
Figure 7D:
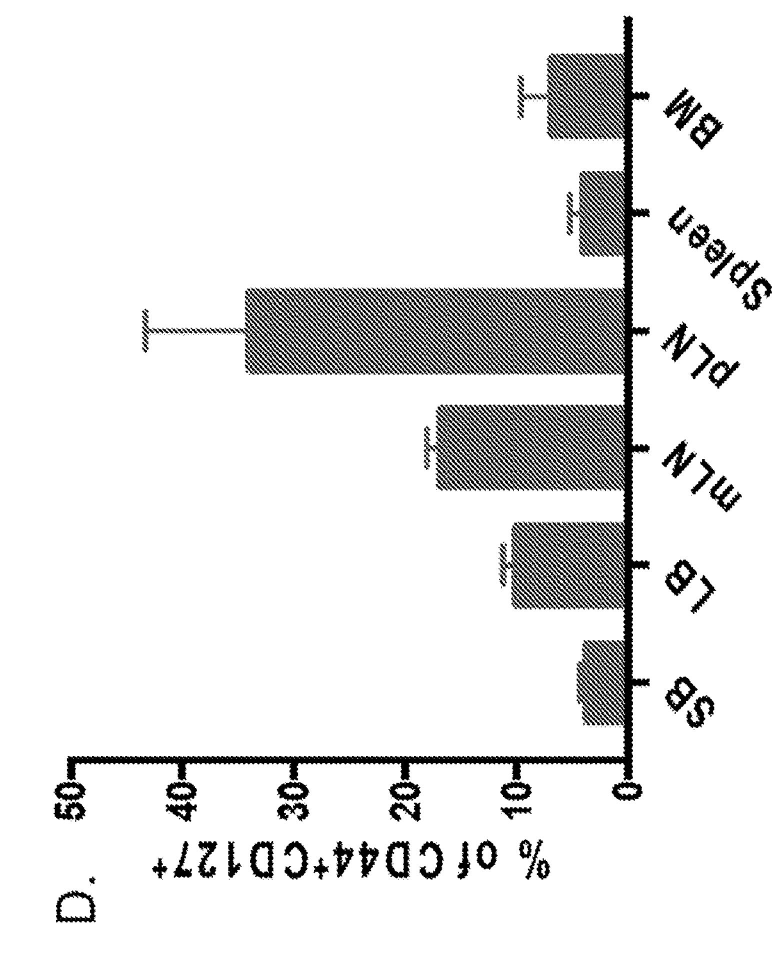
Figure 7E:
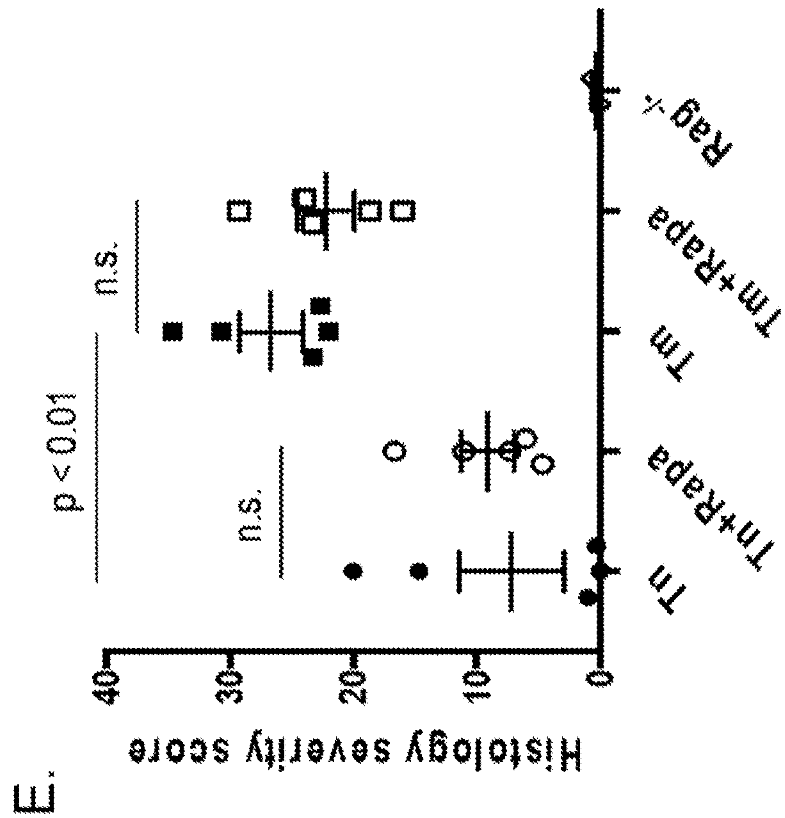

Simultaneous Rapamycin Treatment with Peripheral Antigen Activation Prevents the Development of Naïve CD4+ T Cell Mediated Colitis in Immunocompromised Mice Based on the in vitro and in vivo data above, it was hypothesized that metabolic inhibition with rapamycin during microbiota antigen-specific $CD4^+$ T cell activation would suppress the proliferation of effector cells, thus limiting the intensity of intestinal inflammation. However, the environment in the intestine is heavily suppressive due to constant presence of IL-10 and TGF-β, under which circumstances the inhibitory effect of rapamycin might be impeded. Therefore, it was postulated that microbiota antigen-specific cells need to be attracted to the periphery. This mimics the dissemination of microbial antigens during the disruption of the intestinal mucosa, thus allowing for better metabolic inhibition by rapamycin. To test this hypothesis, an adoptive transfer model of naïve CBir1Tg $CD4^+$ T cells into Rag−/− mice was used to induce T cell mediated colitis with or without peripheral activation by MEP1. On days 1-5 and 8-12, the recipient mice were treated with rapamycin or vehicle control (0.2% CMC) intraperitoneally (i.p.) daily, and then mice were sacrificed on day 18 for histological and cellular assessment (FIG. 6A). Although weight loss was not the best reflection for the severity of colitis, especially when disease course was fairly short in the experimental setup, mice receiving peripheral MEP1 activation and rapamycin treatment had the least wasting symptoms compared to all of the other recipient groups (FIG. 6B). Correspondingly, histological assessment showed that Rag−/− mice receiving CD4 cells, with and without peripheral MEP1 activation, both developed severe colitis; rapamycin treatment, but without peripheral MEP1, was not able to prevent colitis development. However, with the combination of peripheral MEP1 activation and rapamycin treatment, the development of $CD4^+$ T cell mediated colitis was fully prevented, with a comparable histological appearance and disease severity score of the control, healthy Rag−/− mice (FIGS. 6C and 6D). This was because of the successful metabolic inhibition of CBir1Tg CD4 cells in the periphery, resulting in significantly fewer CBir1Tg CD4 cells (FIG. 6E), and, in particular, fewer pathologic effector Th1 and Th17 cells in the colon of the recipient mice as compared to other groups (FIGS. 6F and 6G). Therefore, simultaneous application of rapamycin with microbiota antigen-specific $CD4^+$ T cell peripheral activation could serve as a preventative immunotherapy for the restraint of intestinal inflammation when naïve $CD4^+$ T cells encounter their cognate microbiota antigens for the first time.

Figure 8A:
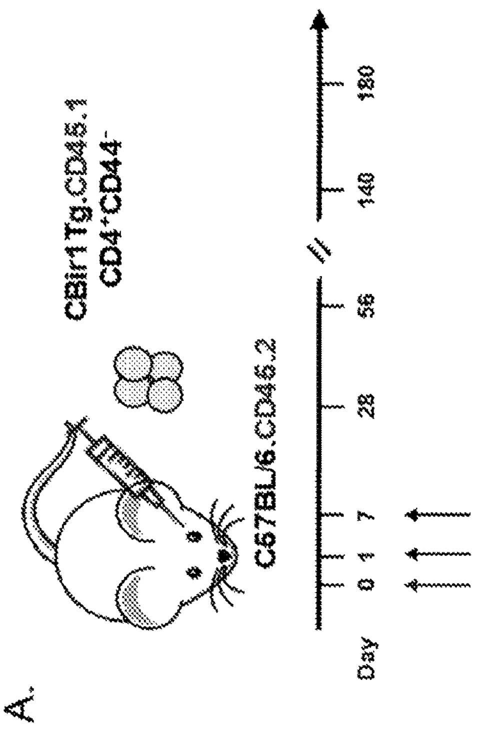
FIGS. 8A-8M show that rapamycin prevents the development of $CD4^+$ $T_M$ while promotes Treg in vivo, in an antigen-specific manner. (A) C57BL/6.CD45.2 mice were adoptively transferred with $2\times10^6$ CBir1Tg·CD45.1 $CD4^+$ $CD44^-$ naïve splenic T cells (red arrow), followed by immunization with 50 μg CBir1 flagellin and 1 μg cholera toxin (CT) on Day 0 and Day 7 (black arrow). Recipient mice without immunization were used as controls. Mice were sacrificed or challenged with CBir1 flagellin (which were then sacrificed 7 days post challenge) on indicated days post transfer for the enumeration of remaining donor CD4+ T cells in the spleen (B). (C) Adoptive transfer, immunization and inhibition strategy with same color indications as in (A). Blue arrow indicates rapamycin i.p. injection at 1 ug/g body weight/day, while mice in the control group were treated only with drug vehicle 0.2% CMC. Day 28 post transfer, lymphocytes were isolated from the recipient mice and analyzed with FACS. Absolute numbers of $CD4^+$ $CD45.1^+$ T cells in spleen, mLN, BM and intestine are shown in (D). Representative plots of donor $CD4^+$ $T_M$, Treg, effector Th1 and Th17 cells ($T_E$), and Tfh in the spleen are shown in (E and H) (red: CMC group; blue: rapa group), whereas combined data of the percentage of donor CD4+ TM and ratios of Treg/$T_E$ based on absolute numbers in the spleen and mLN are shown in (F and G). Serum IgG antibodies specific to CBir1 flagellin and CTB on Day 28 are shown in (I and J). (K) shows adoptive transfer, immunization, and challenging strategy. Red dashed arrow indicates challenging with 3 μg MEP1 i.v. on day 28, and mice were then sacrificed 7 days after. Percentages of donor Treg, and ratios of donor Treg/$T_E$ in the spleen are shown in (L and M).
Figure 8B:
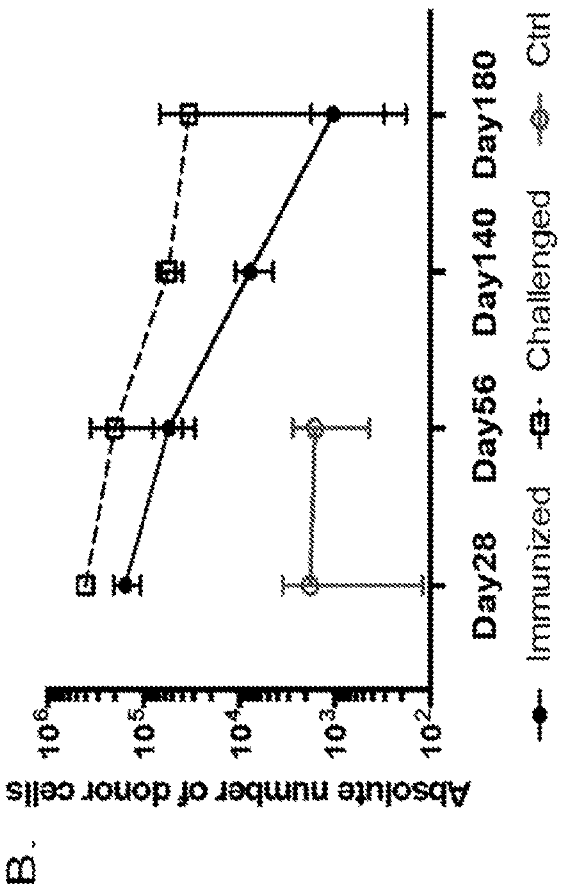
Figure 8C:
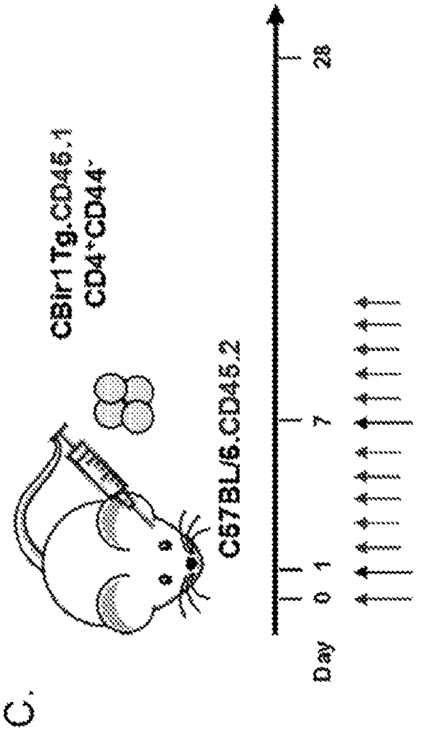
Figure 8D:
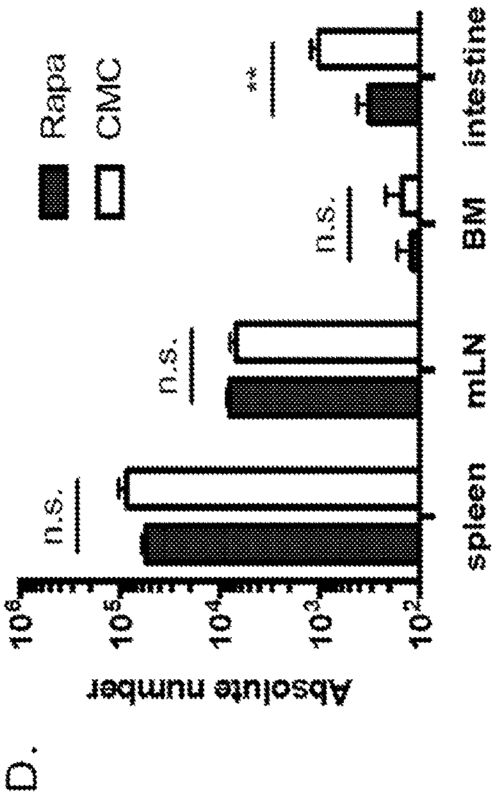
Figure 8E:
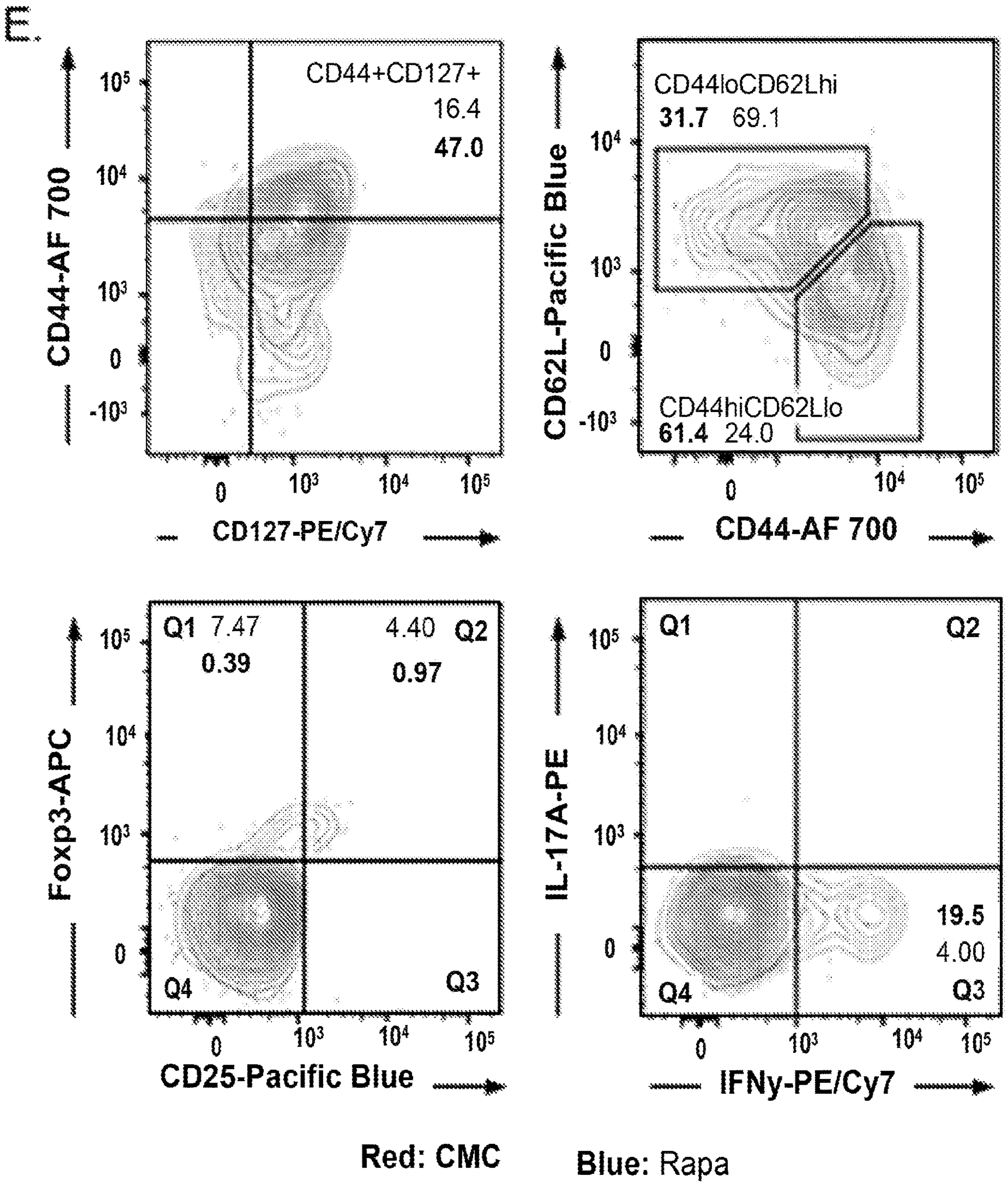
Figure 8G:
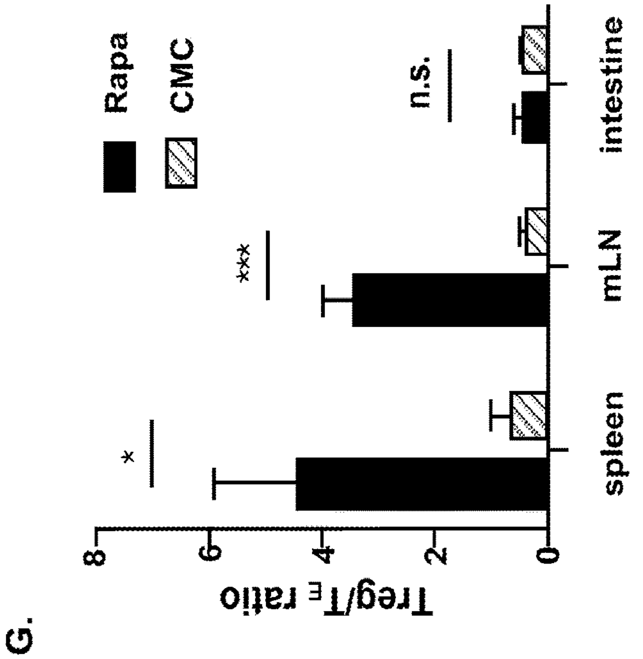
Figure 8F:
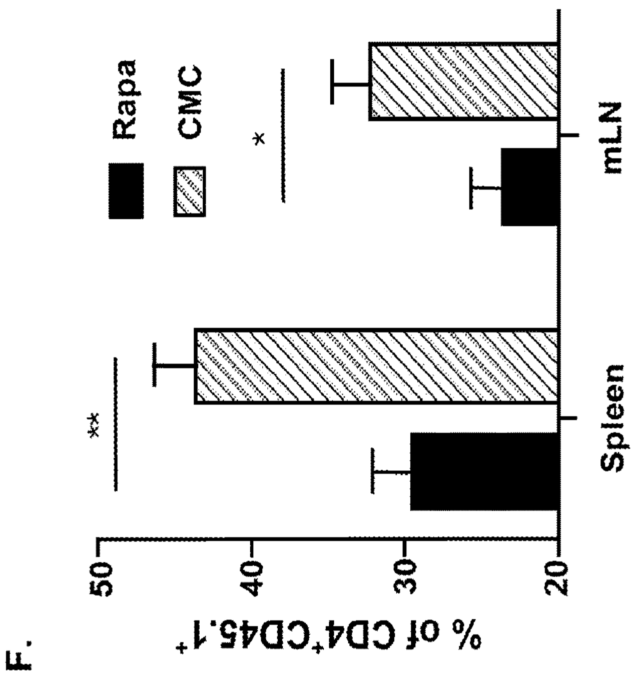
Figure 8H:
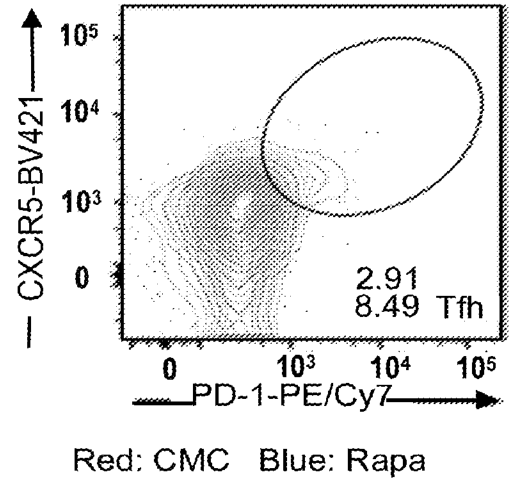
Figure 8I:
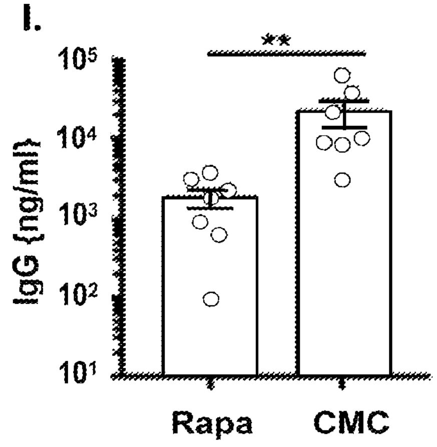
Figure 8J:
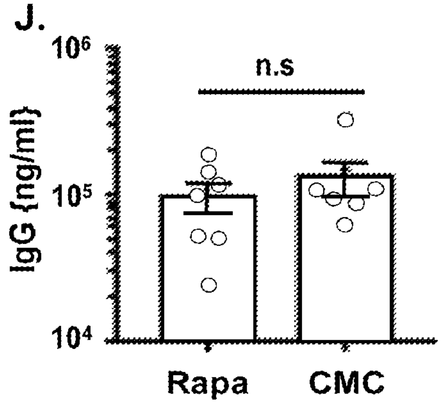
Figure 8K:
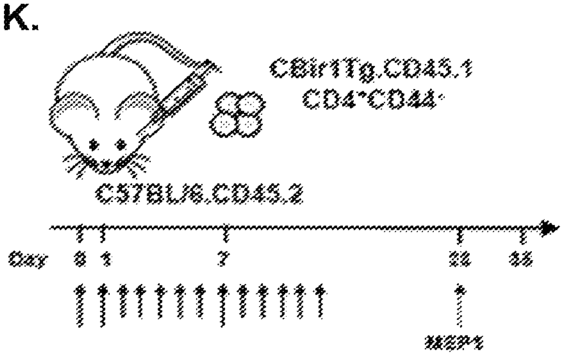
Figure 8L:
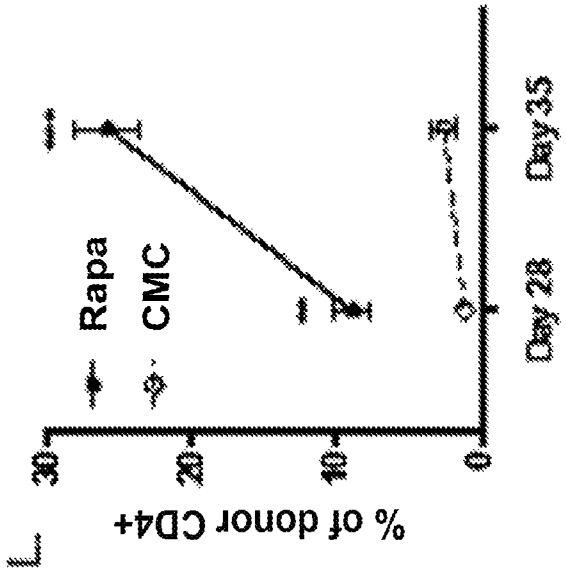
Figure 8M:
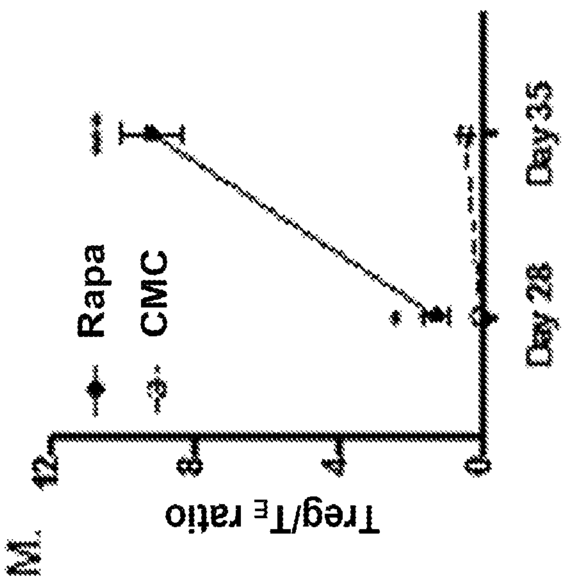
Figure 9B:
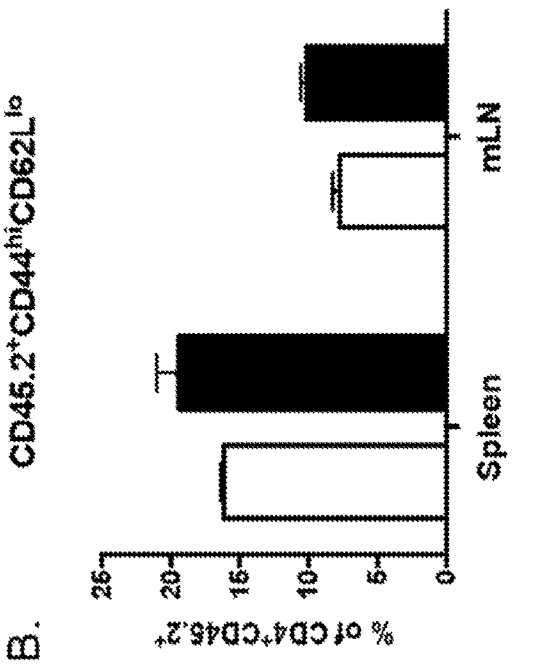
FIGS. 9A-9C show that rapamycin has no effect on host $CD4^+$ $T_M$ and Treg development. B6.CD45.2 mice were transferred with $2\times10^6$ naïve $CD4^+$ T cells from CBir1Tg·CD45.1 mice, followed by i.p. immunization of CBir1 flagellin on day 0) and 7. Recipient mice were treated with 5 days of rapamycin injection at 1 μg/g body weight/day after each immunization, while the control group were treated only with drug vehicle 0.2% CMC. On day 28, lymphocytes were isolated from the spleen and mLN and analyzed with FACS. Percentages of $CD4^+$ $T_M$ cells in the recipient mice are shown in (A and B), whereas host $CD4^+$ Treg cells and their ratio over effector Th1 and Th17 cells ($T_E$) is shown in (C).
Figure 9A:
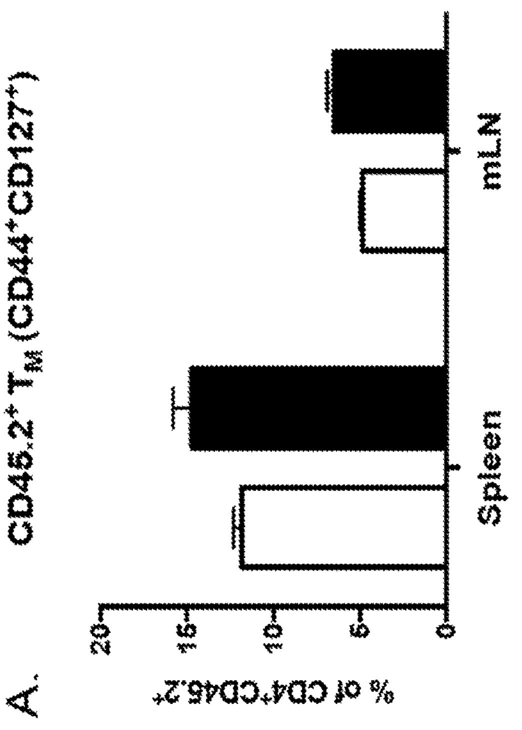
Figure 9C:
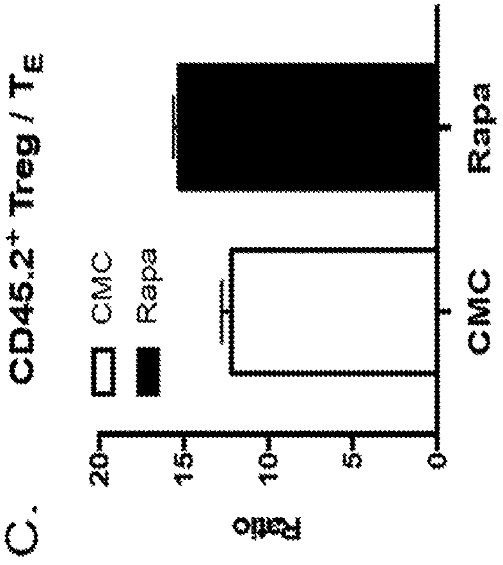

Rapamycin Prevents the Development of CD4+ $T_M$ Cell Response, but Favors the Differentiation of Treg Cells In Vivo, in an Antigen-Specific Manner During acute gastroenteric infection, low levels of $CD4^+$ T cell response against the gut microbiota could also be elicited and thus form long-lasting memory responses. Data provided herein showed that microbiota flagellin-specific $T_M$ cells can also be induced during colitis, using the CBir1Tg naïve $CD4^+$ T cells transfer model, and that these cells circulate through the intestine, bone marrow, and secondary lymphoid organs (FIGS. 7A-7E). Therefore, preventing the formation of microbiota-reactive CD4+ $T_M$ cells with rapamycin during initial antigen encounter diminishes the possibility of upcoming intestinal inflammation. To test this hypothesis, the physiologic development of microbiota-reactive $CD4^+$ TM response in the periphery was mimicked by immunizing C57BL/6 mice, which were transferred with CBir1Tg·CD45.1 $CD4^+CD44^-$ cells, twice with 50 μg CBir1 flagellin i.p. (FIG. 8A). The majority of the transferred $CD4^+$ T cells expressed memory markers ($CD44^+CD127^+$, and CD62Llow) 3 weeks post immunization, and they were present in the recipient mice up to 6 months post immunization for rapid expansion upon CBir1 flagellin challenge (FIG. 8B). Then, whether simultaneous rapamycin treatment during immunization had any impact on the development of memory $CD4^+$ response was analyzed. C57BL/6 mice transferred with congenic CBir1Tg naïve $CD4^+$ T cells received 5 days of rapamycin injection i.p. following immunization, whereas mice receiving drug vehicle 0.2% CMC were used as controls (FIG. 8C). At day 28, the absolute numbers of transferred CD4 cells in both groups were not significantly different, except that fewer CBir1Tg $CD4^+$ T cells were recovered from the intestines of rapamycin-treated mice (FIG. 8D). Compared to the control group. CBir1Tg $CD4^+$ T cells isolated from the spleen and mLN of rapamycin treated mice displayed less memory phenotype but more of a naïve status, by lower expression of CD44 and CD127 (FIGS. 8E and 8F), and higher expression of CD62L (FIG. 8E). In the meanwhile, rapamycin treatment facilitated the expression of Foxp3, but inhibited effector cytokines in transferred cells (FIG. 8E), resulting in dramatic differences of the Treg/Teff ratio in the spleen and mLN of the recipient mice compared to the control group (FIG. 8G). Rapamycin treatment also inhibited the differentiation of antigen-specific T follicular helper (Tfh) cells, assessed by the expression of CXCR5 and PD-1 (FIG. 8H). Correspondingly, rapamycin treated mice had substantially lower anti-CBir1 flagellin IgG in the serum compared to control mice (FIG. 8I). All of these effects derived from rapamycin treatment were antigen-specific, because no such differences were found in the CD4+ cells of the hosts (FIGS. 9A-9C), as well as serum IgG response against cholera toxin B subunit (CTB) (FIG. 8J). In summary, rapamycin treatment during initial antigen encounter in the periphery prevents the development of antigen-specific CD4+ memory response and Tfh cell differentiation, while promoting the differentiation of Treg cells. Furthermore, when these mice were challenged with CBir1 flagellin on day 28, there was a dramatic expansion of Treg cells in the donor portion (FIG. 8L), but not Teff cells (FIG. 8M), indicating that rapamycin imprints the antigen-specific $CD4^+$ T cells during initial antigen encounter, and favors their fate towards Treg cells upon antigen re-challenge.

Figure 10A:
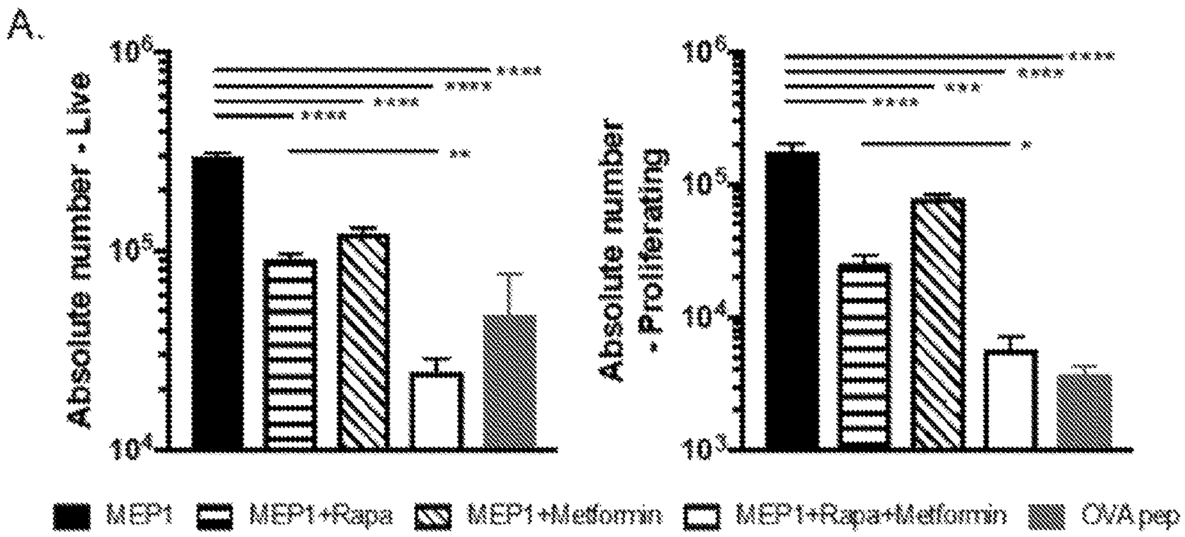
FIGS. 10A-10I show that the combination of rapamycin and metformin ablates pre-existing microbiota antigen-specific $CD4^+$ $T_M$ cells in the periphery in vitro and in vivo. (A) CBir1Tg $CD4^+CD44^+$ $T_M$ cells were isolated from the spleen, labeled with CFSE, and co-cultured with irradiated APCs isolated from C57BL/6 mice in the presence of 1 μg/ml of MEP1, and 100 nM rapamycin, 1 mM metformin, or both. Absolute numbers of live and proliferating $CD4^+$ T cells post 90 hrs of culturing are shown respectively. OVA p323-339 stimulation was used as negative control. (B) Strategy of adoptive transfer, immunization, and ablation of donor $CD4^+$ $T_M$ cells. C57BL/6.CD45.2 mice were adoptively transferred with $2\times10^6$ CBir1Tg·CD45.1 $CD4^+CD44^-$ naïve splenic T cells on Day −1, followed by immunization with 50 μg CBir1 flagellin and 1 μg CT on Day 0 and Day 7 for $CD4^+$ $T_M$ induction. Recipient mice were challenged with 3 μg MEP1 i.v. on Day 28 and Day 35 (black dashed arrow), then followed by i.p. injection of rapamycin (1 μg/g/day), metformin (150 μg/g/day), or the combination of both for 5 days (grey arrow). Mice without challenge and mice treated with 0.2% CMC post challenge were used as controls. Lymphocytes were isolated from the spleen on Day 42 and analyzed with FACS. Representative plots of donor/host $CD4^+$, donor $CD4^+$ $T_M$, Treg, and Tfh are shown in (C), whereas statistics of corresponding absolute numbers are shown in (D-G). Serum IgG antibodies specific to CBir1 flagellin and CTB in the recipient mice are shown in (H and I), respectively.
Figure 10B:
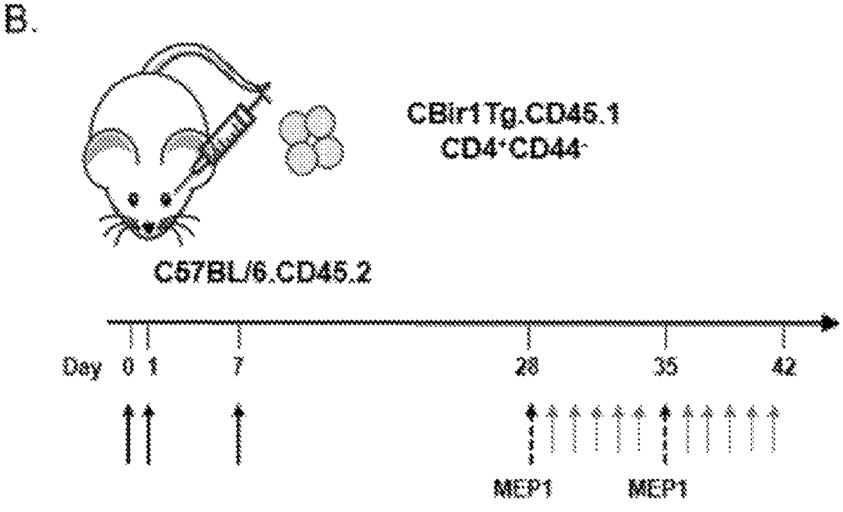
Figure 10C:
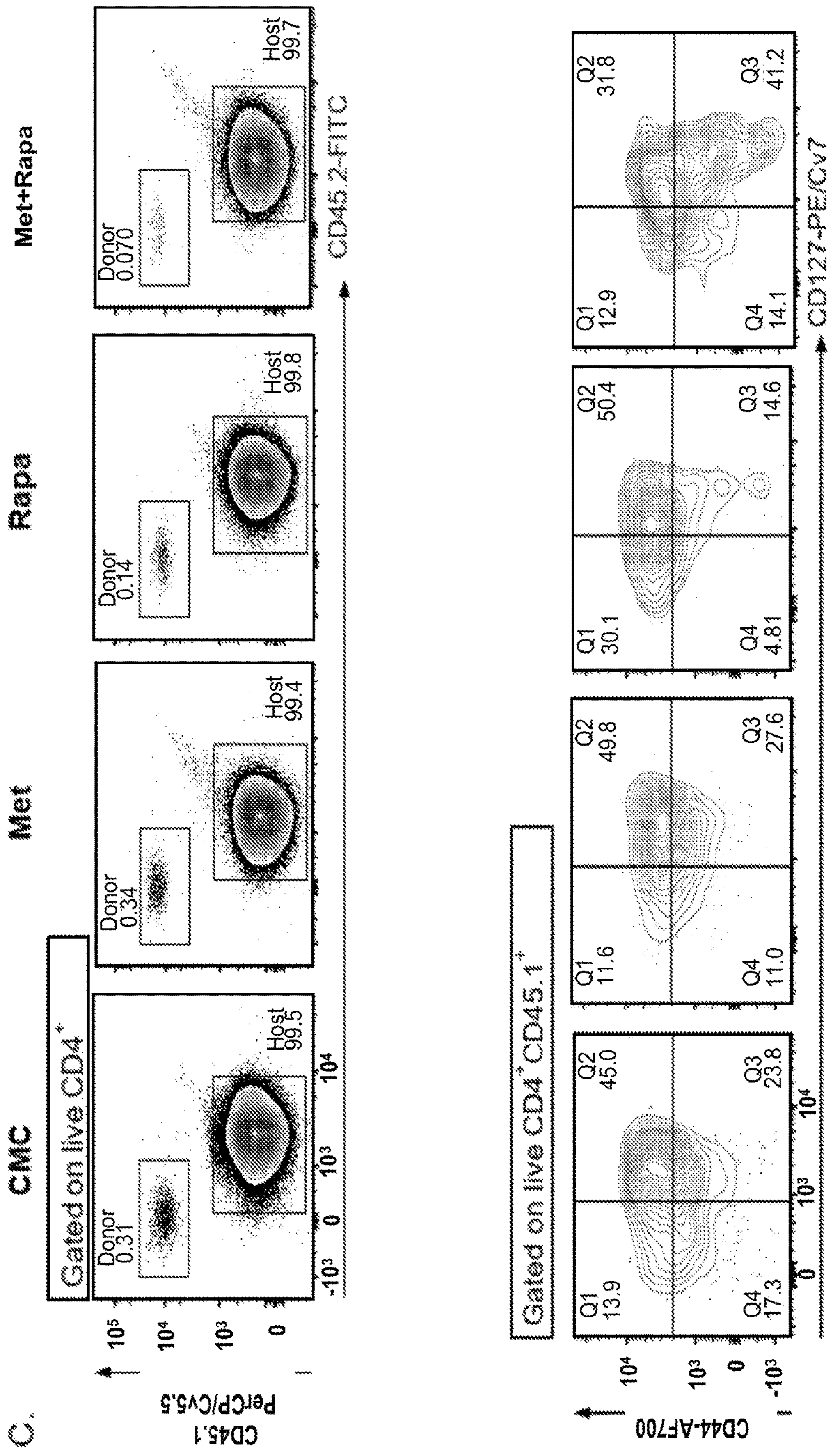
Figure 10E:
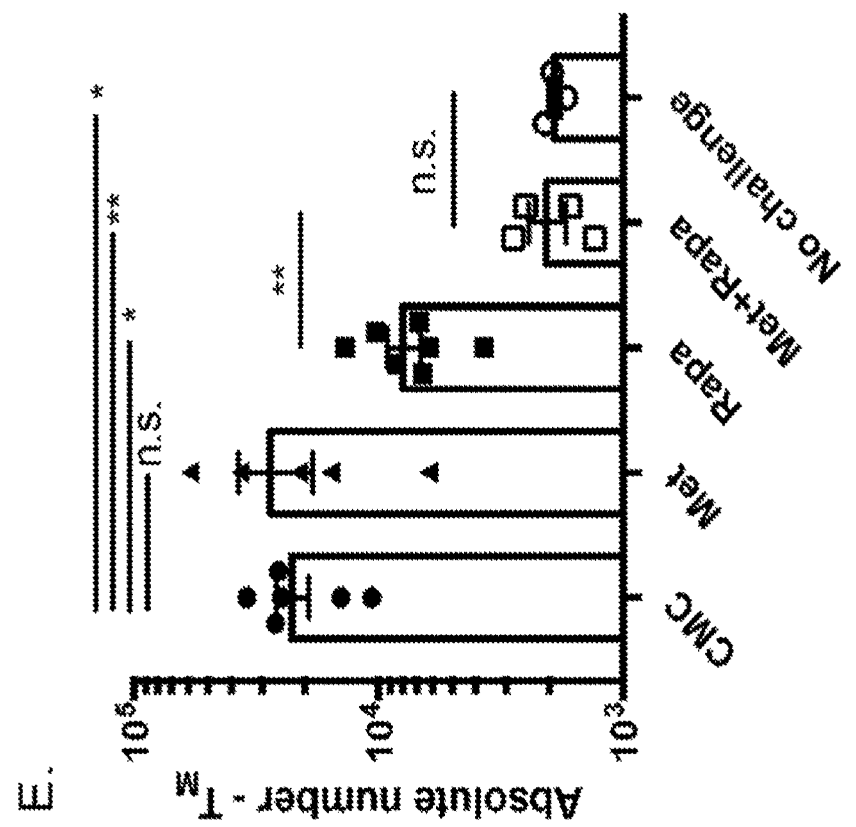
Figure 10D:
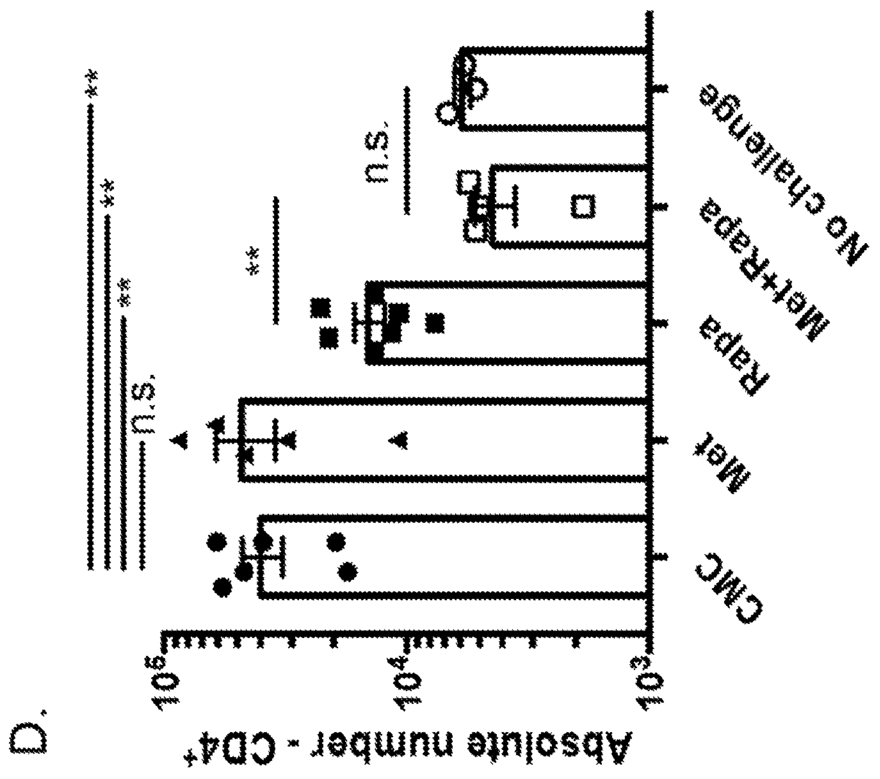
Figure 10G:
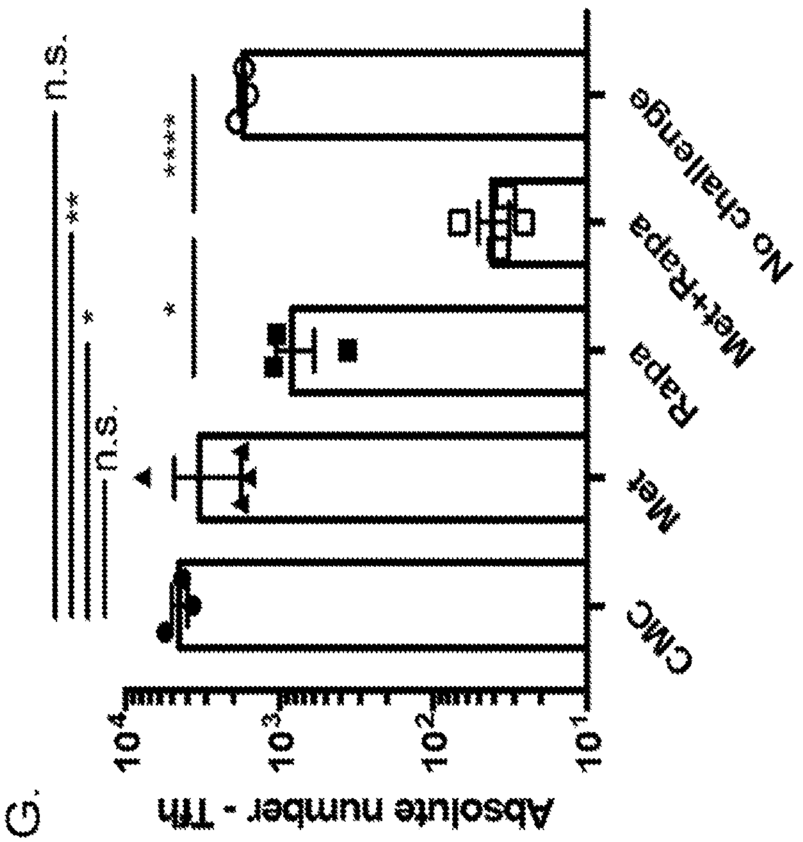
Figure 10F:
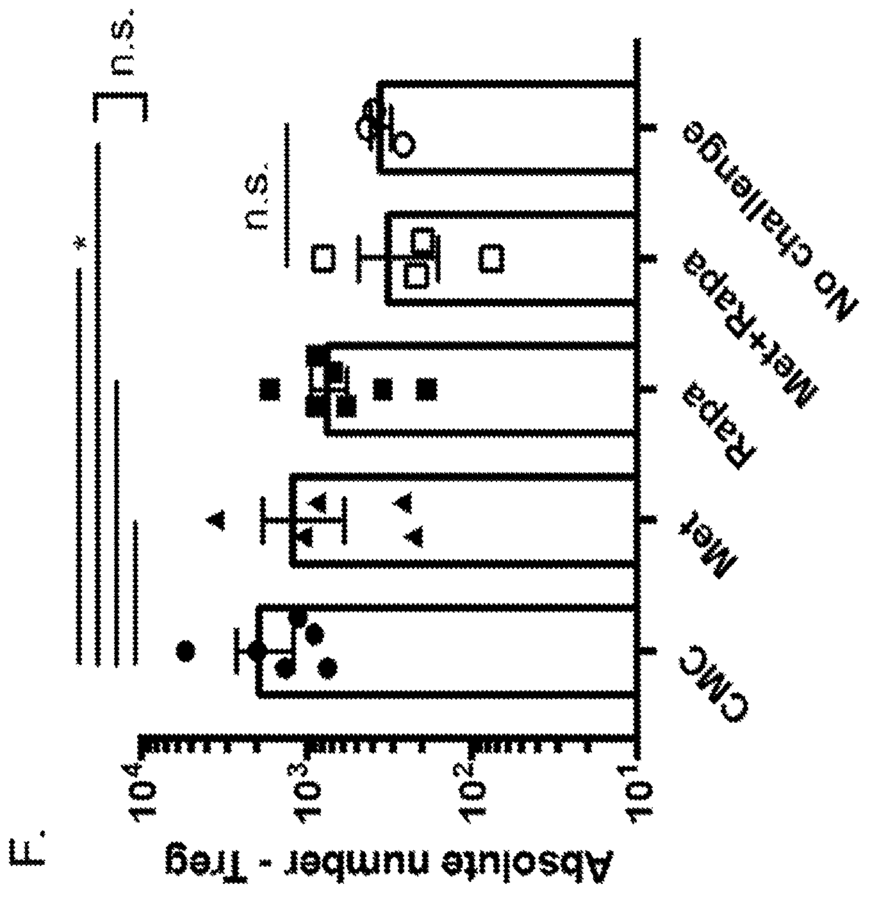
Figure 10H:
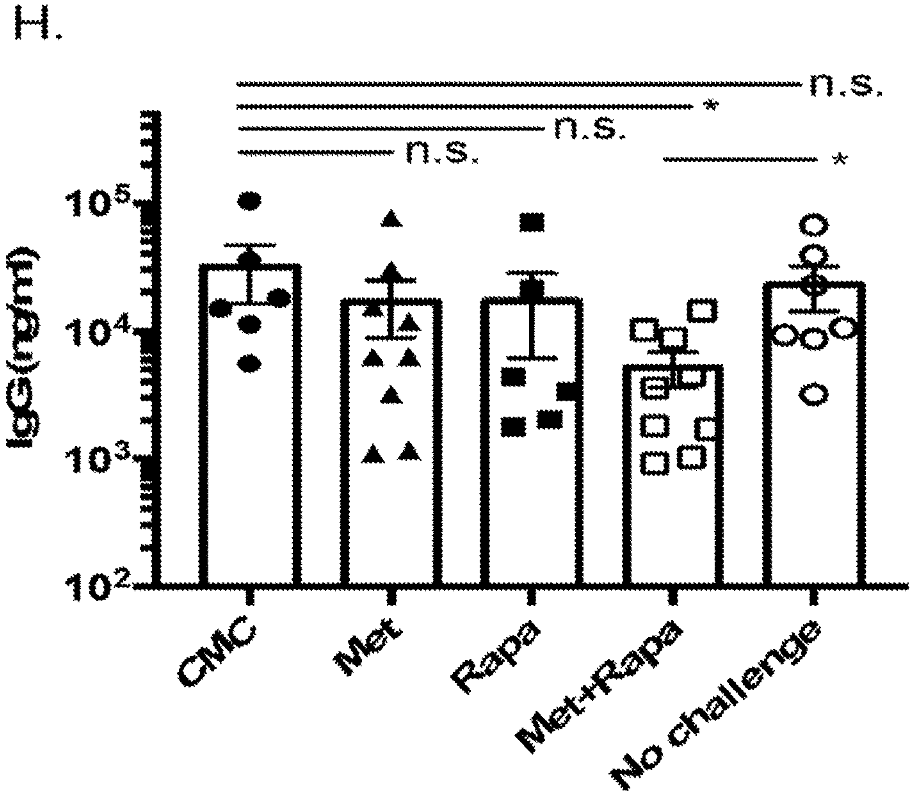
Figure 10I:
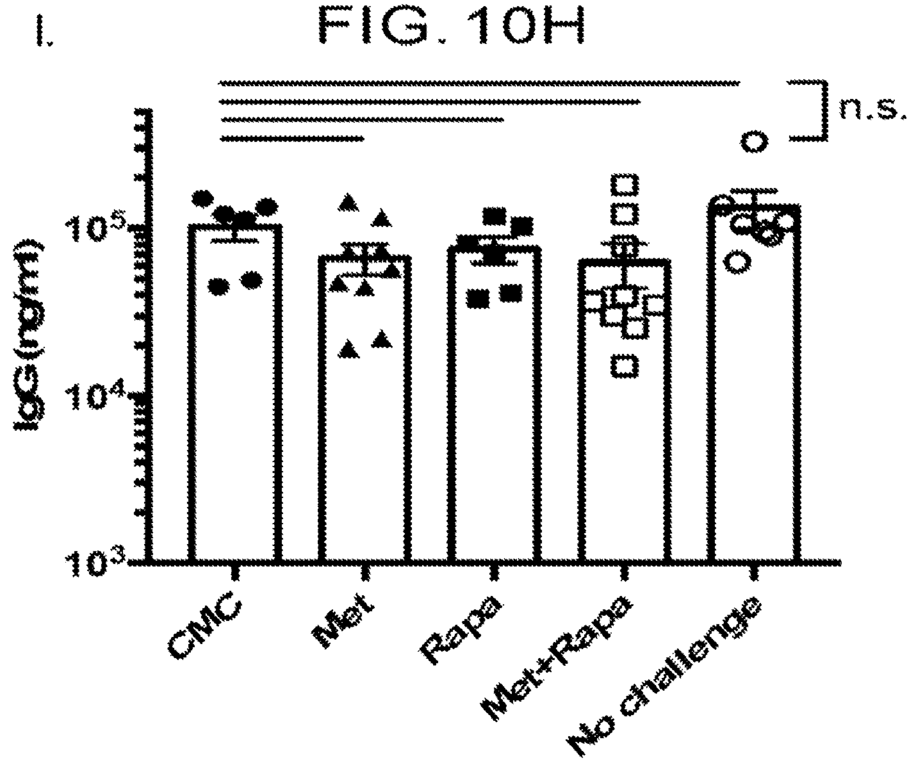

Combination of Rapamycin and Metformin Ablates Existing Microbiota Antigen-Specific $CD4^+$ Ty Cells in the Periphery In Vitro and In Vivo The goal for preventing the relapse of Crohn's disease is to eliminate the circulating microbiota antigen-reactive $CD4^+$ $T_M$ cells during disease remission. These cells are present at low frequencies in the periphery, in patients with Crohn's disease, as well as in experimental models of colitic mice. Unlike naïve $CD4^+$ T cells, when CBir1Tg $CD4^+$ $T_M$ cells were co-cultured with MEP1 and rapamycin in vitro, significant but much less intense cell death and inhibition of cell proliferation was observed. $T_M$ cells engage in minimum mTOR activity but mainly rely on upregulated AMPK activity for their metabolism. Therefore, whether the metabolic inhibitor metformin, which targets the AMPK pathway, or the combination of rapamycin and metformin. could achieve a better inhibitory effect on $CD4^+$ $T_M$ cells was studied. Data from in vitro culturing showed that inhibition with metformin had a comparable effect, or even worse, than rapamycin on activated CD4+ $T_M$ cells. However, the combination of rapamycin and metformin showed a more robustly effective inhibition on cell survival and proliferation, compared to either when used alone (FIG. 10A). This was tested in vivo by targeting established microbiota antigen-specific CD4+ $T_M$ cells in the periphery. C57BL/6·CD45.2 mice were transferred with congenic CBir1Tg CD4+$T_N$ cells and immunized with CBir1 flagellin i.p. twice for antigen-specific $CD4^+$ $T_M$ induction. Upon antigen challenge, on days 28 and 35, recipient mice were treated with metformin, rapamycin, the combination of both, or drug vehicle for 5 consecutive days, respectively. Recipient mice with immunization but no antigen challenge were used as controls (FIG. 10B). Assessed by the absolute numbers recovered from the spleen. CBir1Tg CD4+ cells vastly expanded after antigen challenge, with no inhibitory result seen when mice were treated with metformin alone. Moderate inhibition was observed with rapamycin alone. However, when mice were treated with the combination of rapamycin and metformin. the expansion of CBir1Tg CD4+ $T_M$ cells was completely prohibited, which was not different from mice without challenge (FIGS. 10C and 10D). Furthermore, their remaining CBir1Tg CD4+ T cells displayed a less activated phenotype, with significantly decreased co-expression of CD44 and CD127, and increased expression of CD62L (FIGS. 10C and 10E). On the other hand, although the expansion of CBir1Tg CD4+ T cells was inhibited with rapamycin or rapamycin+metformin treatment, there was a significant induction of $T_{reg}$ population in the remaining CBir1Tg $CD4^+$ cells, which was not seen in other groups (FIGS. 10C and 10F). Of note, rapamycin, especially the combination of rapamycin and metformin, also inhibited the differentiation of antigen-specific Tfh cells upon challenge (FIGS. 10C and 10G), resulting in a decreased level of serum anti-CBir1 flagellin IgG (FIG. 10H), whereas the level of pre-existing antibody irrelevant to antigen challenge had no difference (FIG. 10I). In summary, these results indicated that $CD4^+$ $T_M$ cells engage different metabolic pathways with $CD4^+$ $T_N$ cells. Therefore, the combination of mTOR inhibitor rapamycin and AMPK activator metformin resulted in a more robust ablation of pre-existing microbiota antigen-specific $CD4^+$ $T_M$ and Tfh cells, as well as induction of Treg cells.

Figure 11A:
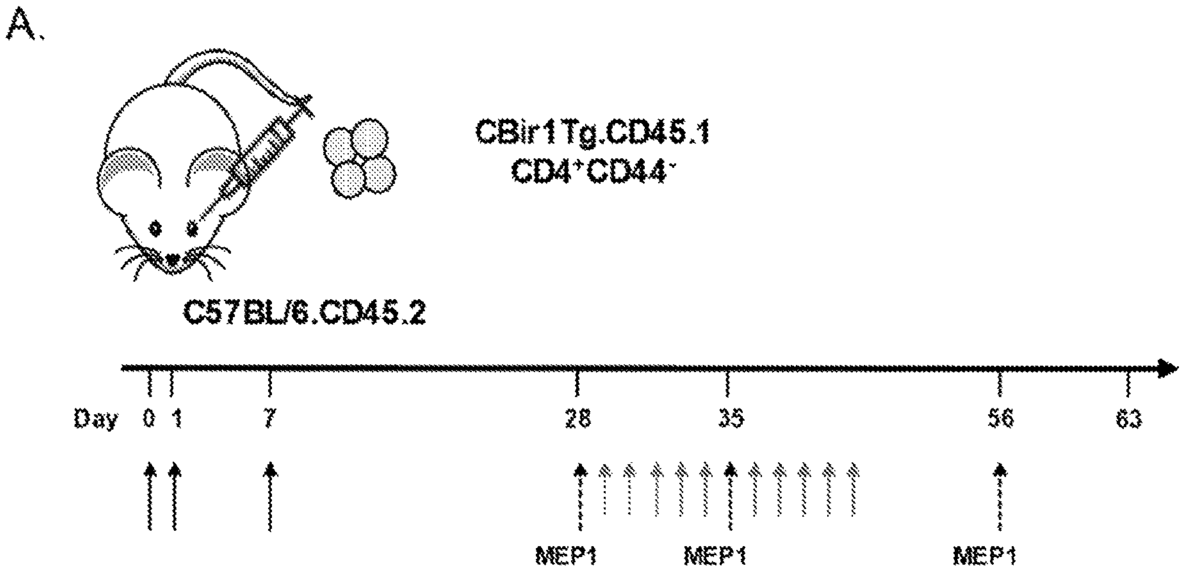
FIGS. 11A-11G show that metabolic checkpoint inhibition dampens antigen-specific $CD4^+$ T cell recall response post ablation. (A) Strategy of adoptive transfer, immunization, and ablation of donor $CD4^+$ $T_M$ cells. C57BL/6.CD45.2 mice were adoptively transferred with $2\times10^6$ CBir1Tg·CD45.1 $CD4^+CD44^-$ naïve splenic T cells on Day −1, followed by immunization with 50 μg CBir1 flagellin and 1 μg CT on Day 0 and Day 7 for $CD4^+$ $T_M$ induction. Recipient mice were challenged with 3 μg MEP1 i.v. on Day 28 and Day 35 (black dashed arrow), then followed by i.p. injection of rapamycin (1 μg/g/day), metformin (150 μg/g/day), or the combination of both for 5 days (grey arrow). Mice without MEP1 challenge on Day 28 and 35 were used as no treatment controls; and mice treated with 0.2% CMC post MEP1 challenge were used as drug vehicle controls. All groups received a MEP1 challenge on Day 56. Lymphocytes were isolated from the spleen on Day 63 and analyzed with FACS. Representative plots of donor $CD4^+$ $T_M$ are shown in (B), whereas statistics of absolute numbers of donor $CD4^+$ T cells, $T_{EM}$ cells, To cells, and CD27 expression in donor $CD4^+$ T cells were shown in (C-F). RNA-sequencing was performed with flow sorted donor $CD4^+$ T cells (n=3-4 mice per group), and log 2 fold change of gene expression levels in treated mice compared to no treatment group were shown in (G).
Figure 11B:
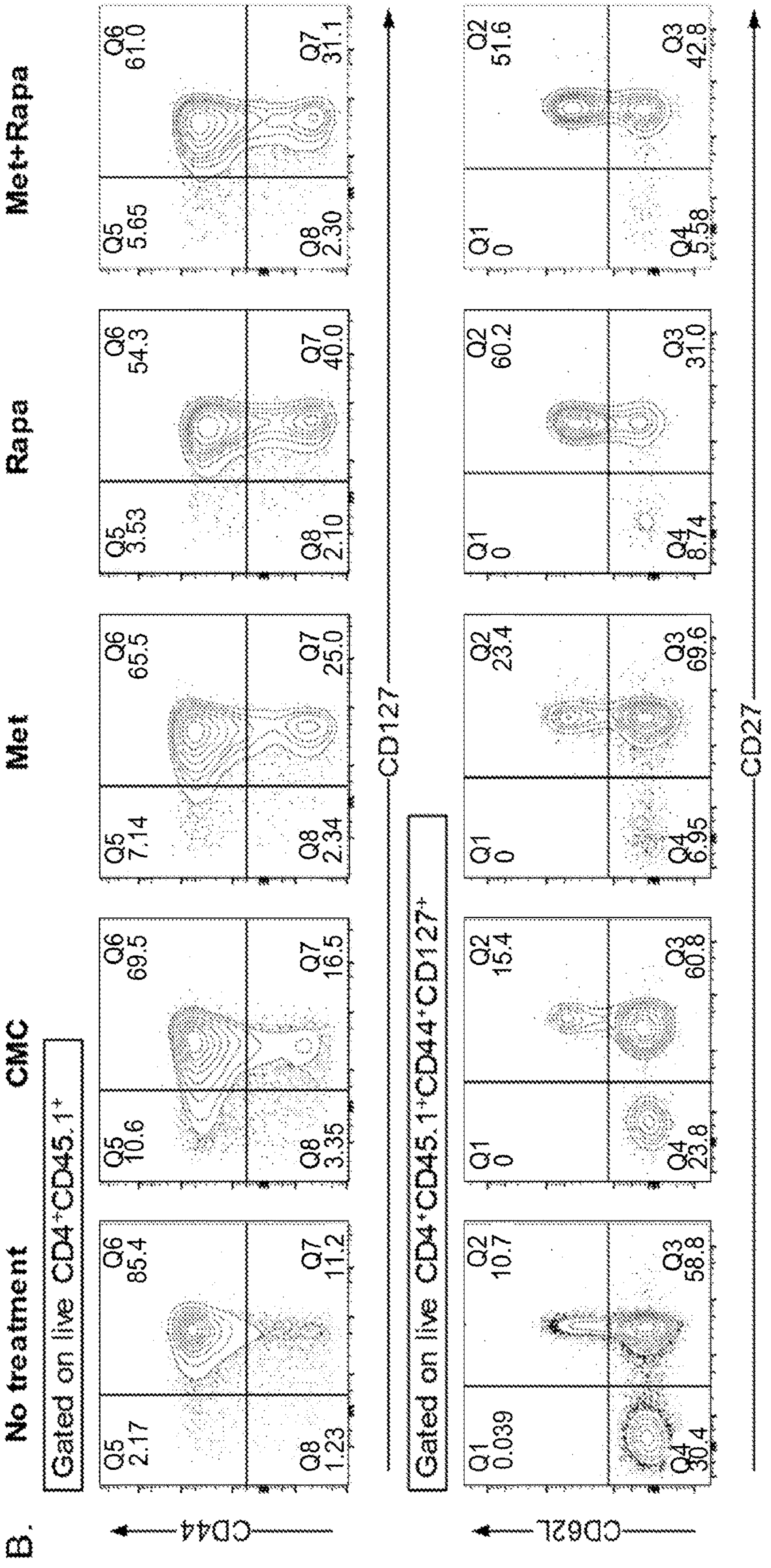
Figure 11D:
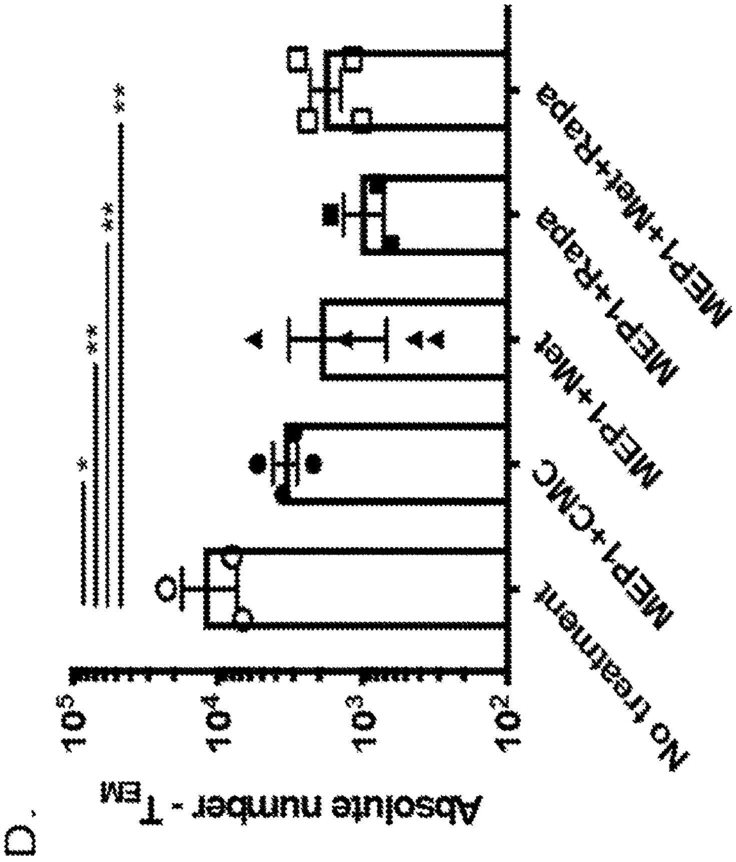
Figure 11C:
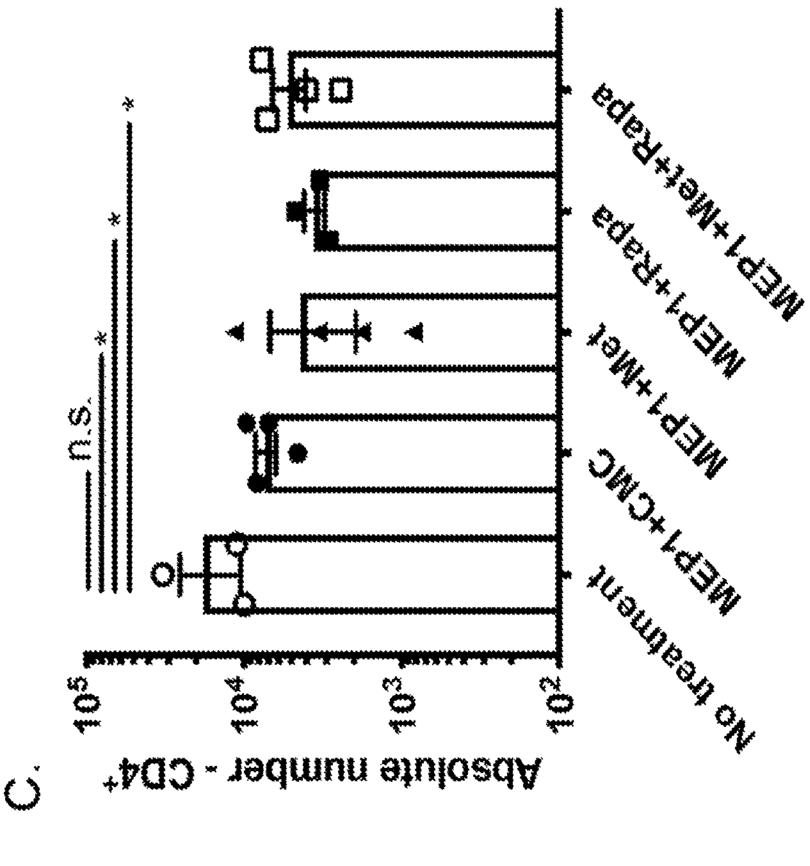
Figure 11E:
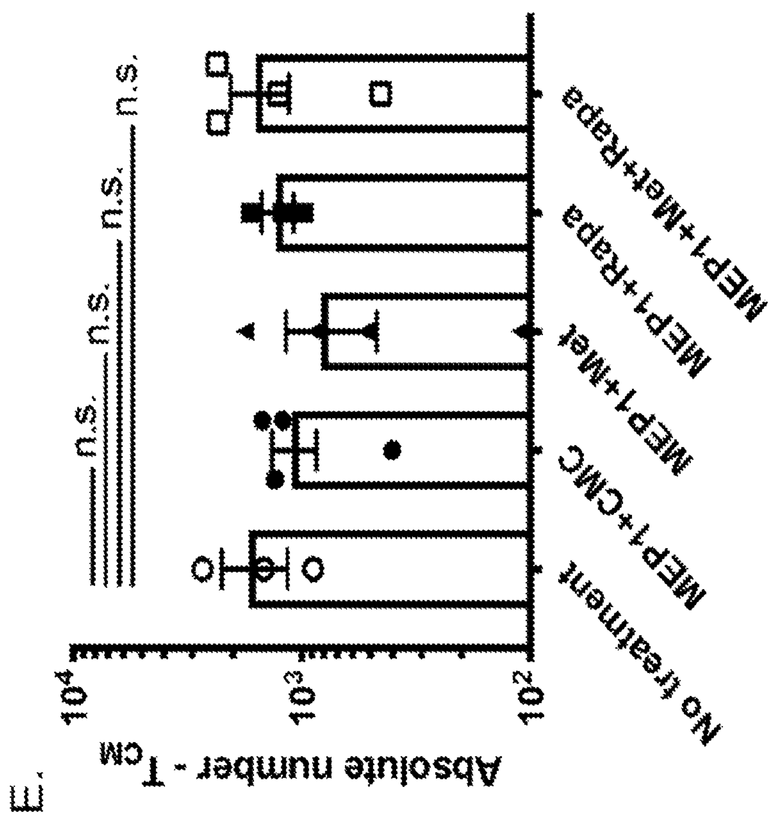
Figure 11F:
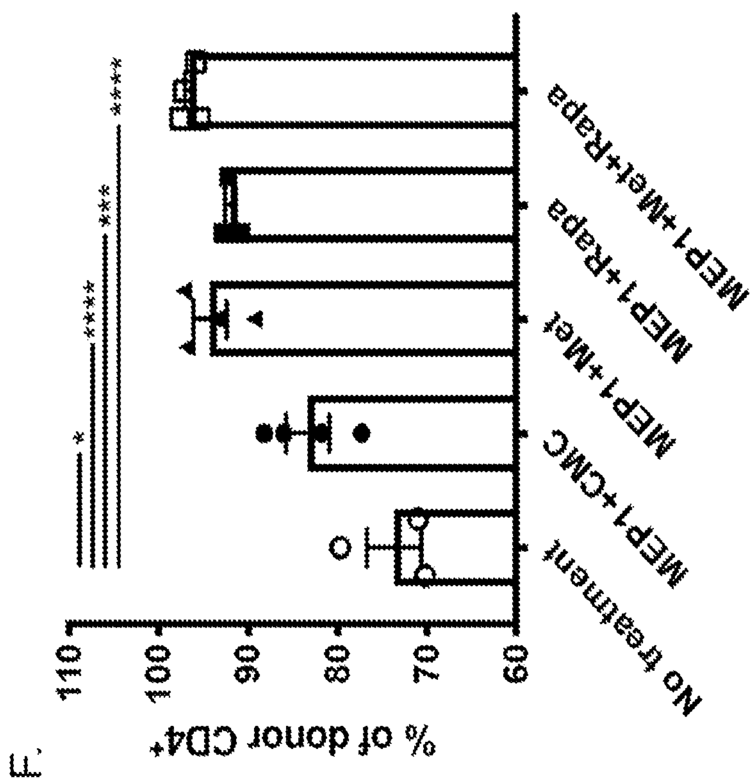
Figure 11G:
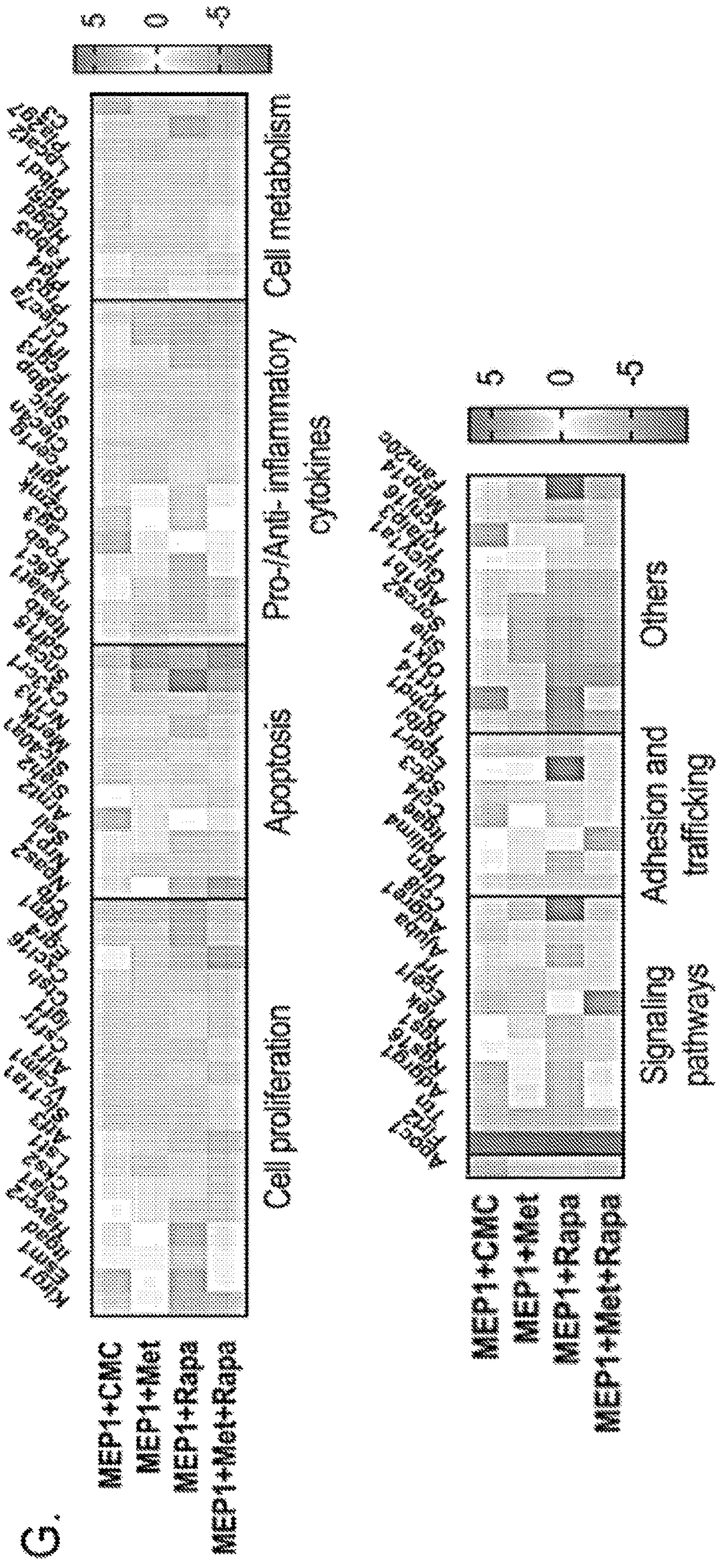

MIdCA with Rapamycin and Metformin Successfully Inhibits the Survival and Proliferation of Circulating Microbiota Antigen-Specific CD4+ T Cells in Crohn's Patients Microbiota antigen-specific $CD4^+$ $T_M$ cells are found circulating in both healthy people and patients with Crohn's disease. However, significantly elevated serum anti-microbiota flagellin IgG response was only found in Crohn's patients, not in healthy people, indicating a functional difference of these $CD4^+$ T cells under disease conditions. Whether microbiota-specific $CD4^+$ $T_M$ cells in patients with Crohn's disease could be depleted with the MIdCA strategy described herein was investigated. Using the published antigen-reactive T cell enrichment (ARTE) protocol, $CD154^+CD69^+$ antigen-specific $CD4^+$ T cells were isolated from peripheral blood mononuclear cells (PBMCs) obtained from patients with Crohn's disease and healthy controls upon stimulation with pooled flagellin antigens including CBir1, 14-2 Fla1, A4 Fla3, and A4 FlaX (FIGS. 11A and 11B). Consistent with serologic data the frequencies of microbiota flagellin-specific $CD4^+$ T cells in PBMCs were significantly elevated in patients with high serum IgG antibody response against multi-flagellin-antigens (reactive to >50% of Lachnospiraceae flagellin antigens tested), but not in patients with low anti-flagellin serum IgG or healthy donors (FIG. 11C). Also, pooled flagellin-specific CD154+ cells isolated from Crohn's patients had significantly higher expression of effector cytokines including IFNγ, TNFα, and IL 17-A post 7 hr stimulation. With magnetic beads labeling, these cells were enriched from ~0.5% to ~30% out of the total CD4+ population (FIG. 11B) and further sorted with flow cytometry for ex vivo expansion with IL-2 and IL-7. Different from a previous study, the percentage of memory cells (CD45RO+) in flagellin-specific CD4+ T cells freshly post sorting ranged widely, from less than 20% to over 80% in different patients (FIGS. 11E and 11F). Therefore, in order to target the metabolism of both naïve and memory CD4+ subsets, rapamycin, metformin, or both were tested, for their inhibitory effects on these cells post expansion. Similar to the murine data, rapamycin treatment alone upon re-stimulation with pooled flagellin greatly inhibited the phosphorylation of S6K to ~50% reduction compared to antigen alone (FIGS. 11G and 11J), leading to significantly increased cell death (FIGS. 11H and 11K) and decreased cell proliferation (FIGS. 11I and 11L). As expected, metformin treatment alone had no inhibitory effect on the mTOR pathway and resulted in a lesser extent of increased cell death and decreased proliferation. Although a synergetic inhibitory effect of rapamycin and metformin on cell proliferation was not observed, the survival of flagellin-specific CD4+ T cells post re-stimulation was significantly lower than either of the drugs when applied alone. Of note, neither rapamycin or metformin treatment altered the cytokine production, such as IFNγ, TNFα and IL-17A, in microbiota flagellin-specific CD4+ T cells upon re-stimulation (FIG. 12).

Metabolic Checkpoint Inhibition Dampens Antigen-Specific $CD4^+$ T Cell Recall Response Post Ablation In order to further determine the cellular response of remaining CBir1 TCR Tg $CD4^+$ T cells post treatment when they re-encounter their cognate antigen, recipient mice with the experimental setup above were challenged with MEP1 on day 56 (FIG. 11A). The total numbers of donor CBir1Tg $CD4^+$ T cells a week post challenge in mice treated with MEP1 plus different metabolic inhibitors were significantly decreased than those in mice without treatment (FIG. 11C). Further analysis showed that the phenotype of donor CBir1Tg $CD4^+$ T cells was overall similar among different treatment groups, with significantly increased naïve $CD4^+$ T cell population and decreased effector $CD4^+$ T cells and memory $CD4^+$ T cells compared to the non-treatment group, assessed by expression of CD44, CD127, and CD62L (FIG. 11B). The decrease of the memory $CD4^+$ T cell population was particularly due to the ablation of effector memory $CD4^+$ T cell subset ($CD44^+CD127^+CD62L^{lo}$), but not central memory $CD4^+$ T cells ($CD44^+CD127^+CD62L^{hi}$) (FIGS. 11D and 11E). Consistently. CD27 expression, which indicates an enhanced cell survival, was upregulated in the remaining CBir1 TCR Tg $CD4^+$ T cells in mice treated with metabolic inhibitors (FIGS. 11B and 11F). These results suggest that multiple rounds of intermittent peptide plus metabolic inhibition may be needed to completely convert the remaining $CD4^+$ $T_{CM}$ into $T_{EM}$ cells in order to fully ablate the circulating microbiota-reactive memory $CD4^+$ T cells in the host. Furthermore. RNA-seq on the remaining CBir1Tg $CD4^+$ T cells post challenge revealed that treatment with MEP1 plus metabolic inhibition significantly affected the expression of genes involved in cell proliferation (Cxcl16, Ctsh, Tgm1, Esm1, Havcr2, Slc11a1, Vcam1, Klrg1, Igf1, Csf1r, Aif1, Itgad, cfb, Atf3, Lst1, (ks2), apoptotic process (Snca, Ctsh, Mertk, Nrlh3, Sell, Nrp1, Npas2, Slc40a1, Siah2), pro/anti-inflammatory cytokine production (Fosb, Il18bp, Il1r1, Clec7a, Slc11a1, Clec4n, Fegr3), cell glucose and lipid metabolism (Snca, Pla2g7, C3, Lpcat2, Igf1, Pld4, Fabp5, Plbd1, Nr1h3, Hpgd), and cell signaling and trafficking (Adgrg1, Rgs16, Rgs1, Ecell, Pdlim4, Itgae, Ccl4) (FIG. 11G), demonstrating that MEP1 plus metabolic inhibition immunotherapy ablates circulating microbiota-reactive $CD4^+$ T cells by inhibiting the survival and proliferation of antigen-specific $CD4^+$ T cells as well as dampening their pro-inflammatory functions.

Figure 12A:
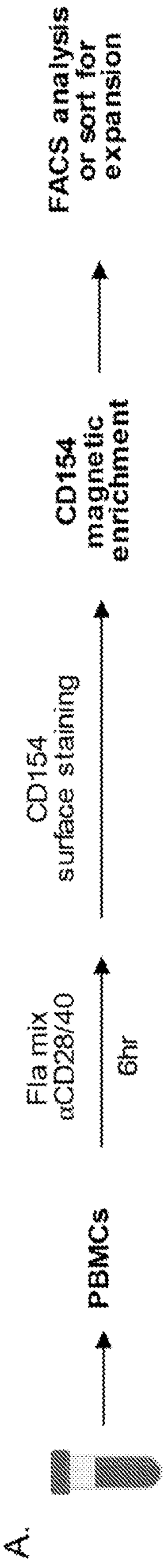
FIGS. 12A-12M show that metabolic checkpoint inhibition dampens the survival and proliferation of circulating microbiota antigen-specific $CD4^+$ T cells isolated from Crohn's patients. (A) At least $10^7$ PBMCs isolated from Crohn's patients with high serologic responses to multiple Lachnospiraceae flagellins (CD high, n=10), Crohn's patients with low serologic responses to Lachnospiraceae flagellins (CD low, n=10), and healthy controls (HC, n=10) were stimulated with a mix of four flagellin antigens (Fla mix, composed of A4 Fla-3, A4 Fla-4, 14-2 Fla-1 and CBir1 Fla, 10 μg/ml each) and 1 μg/ml anti-CD28 and anti-CD40 for 7 hours before enrichment with CD154-biotin/anti-biotin magnetic beads. Cells stimulated without antigens, but only anti-CD28/CD40 were used to assess non-specific CD154 up-regulation. Cells were then stained for CD154, CD69, CD45RO, and intracellular cytokines, and analyzed by flow cytometry. Representative plots of $CD69^+CD154^+$ cells in $CD3^+CD4^+$ gate pre- and post-enrichment are shown in (B), and percent of $CD154^+$ cells in total viable $CD4^+$ cells are shown in (C), where each dot represents an individual. Representative flow plots and statistics of IFNγ expression in $CD4^+CD154^+$ cells post stimulation are shown in (D and E). A representative flow plot and the percentage of $CD45RO^+$ cells in $CD69'CD154^+$ cells post-enrichment and in $CD3^+CD4^+$ cells pre-enrichment is shown in (F and G). Microbiota flagellin-specific $CD4^+$ T cells were labeled with proliferation dye and re-stimulated with autologous APCs plus Fla mix in the presence of 50 nM rapamycin, 1 mM metformin, or both. Phosphorylation of S6K was examined after 6 hours of stimulation (H and K), whereas $CD4^+$ T cell survival (I and L) and proliferation (J and M) were examined after 6-7 days.
Figure 12C:
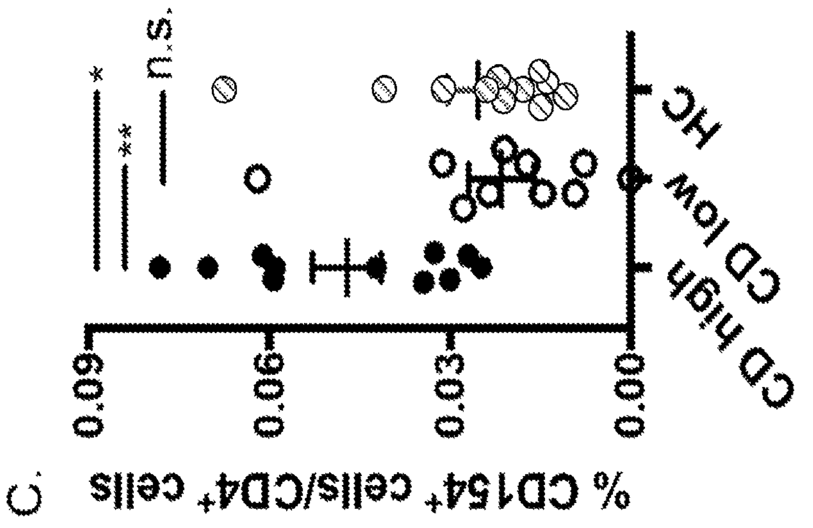
Figure 12B:
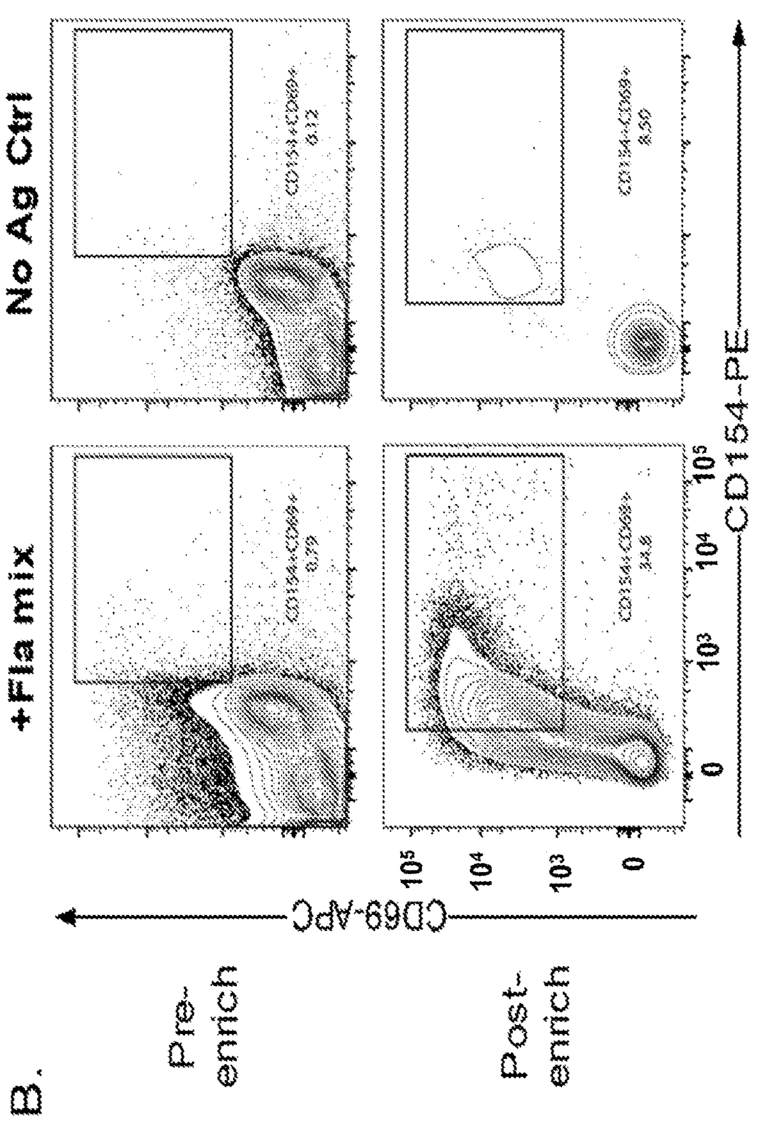
Figure 12E:
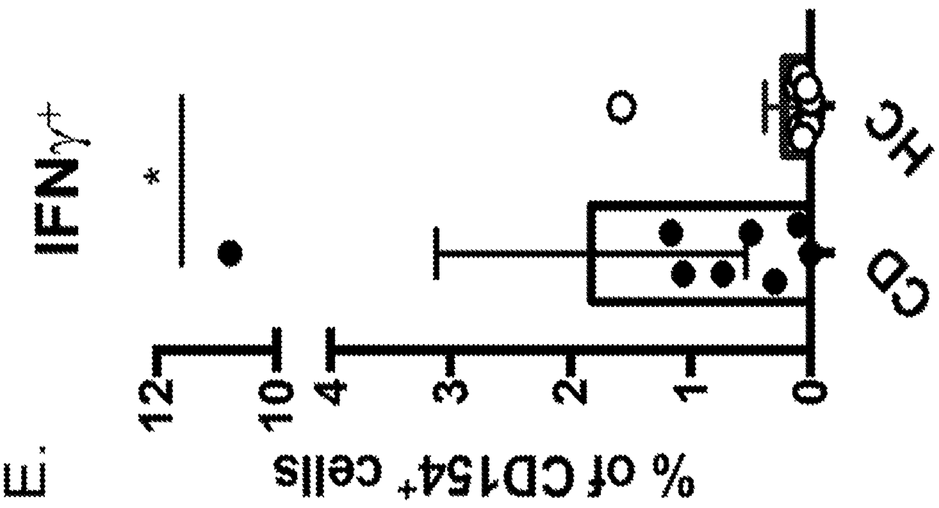
Figure 12D:
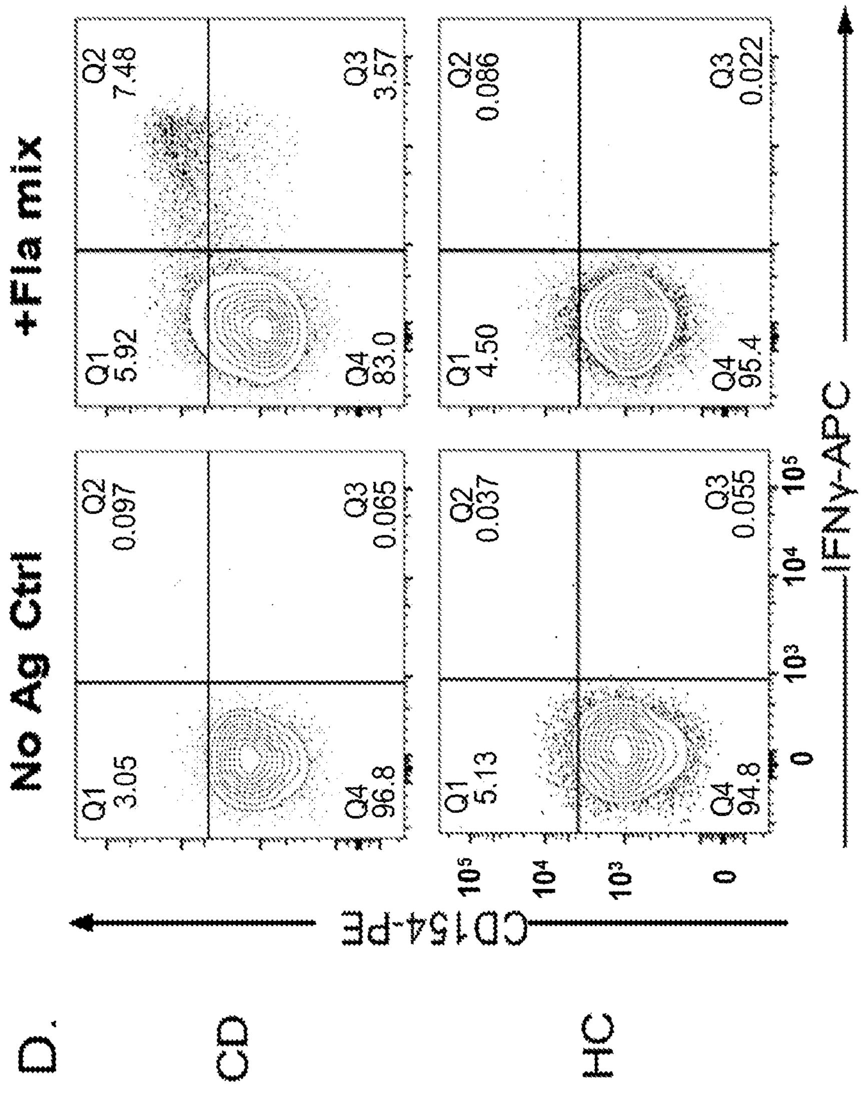
Figure 12G:
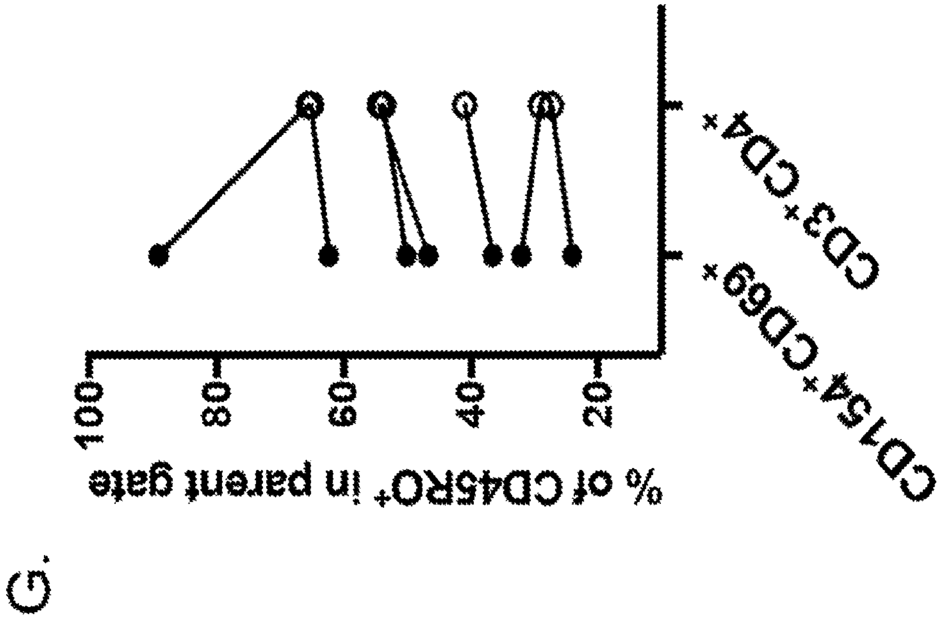
Figure 12F:
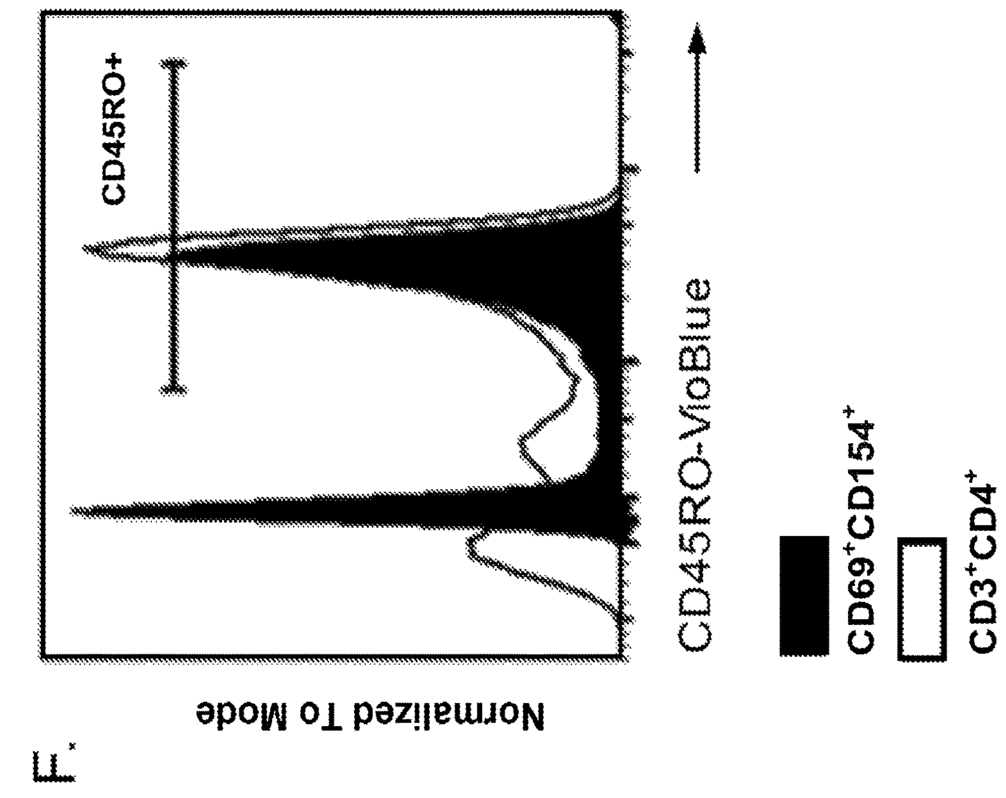
Figure 12H:
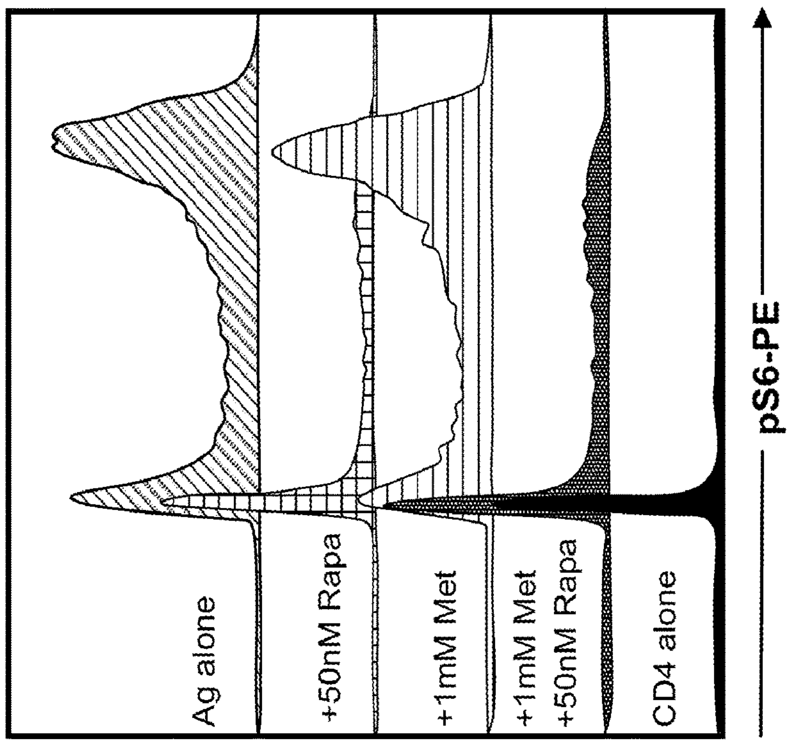
Figure 12I:
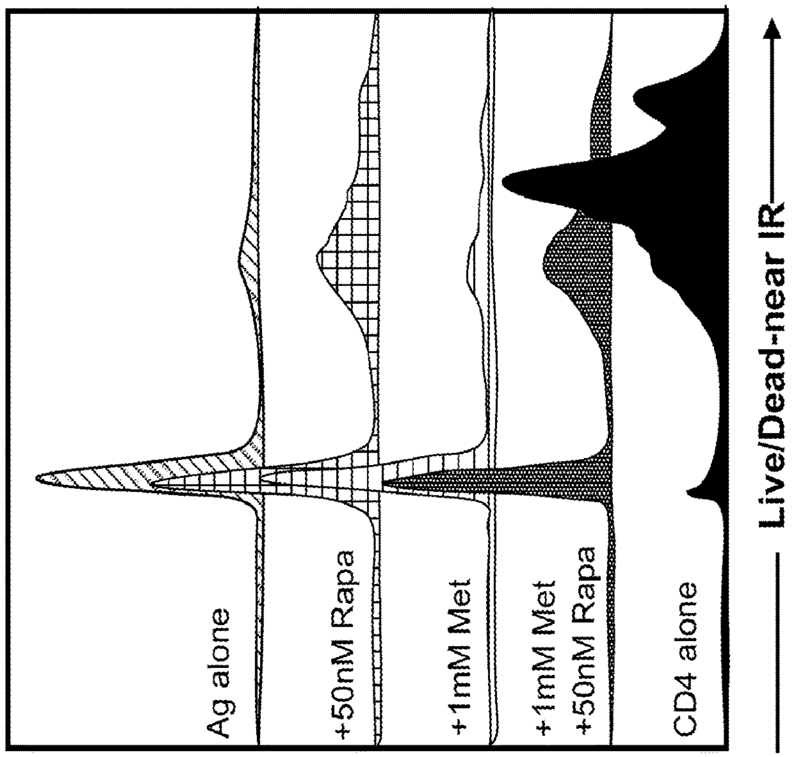
Figure 12J:
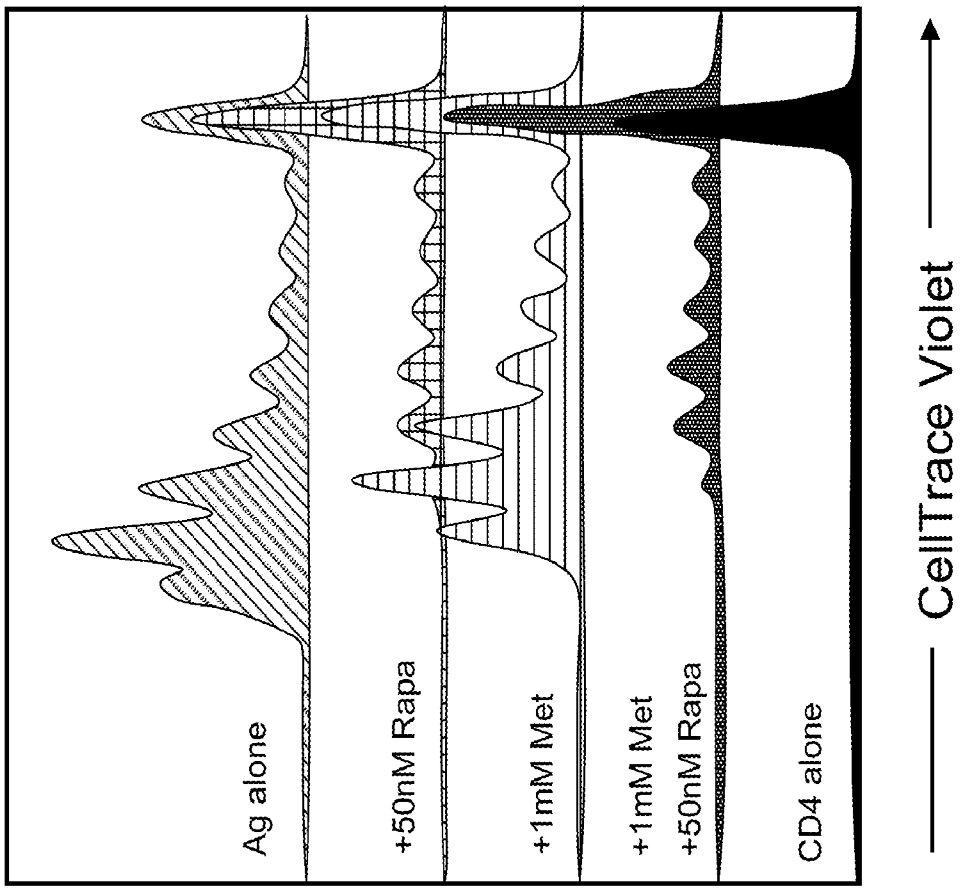
Figure 12L:
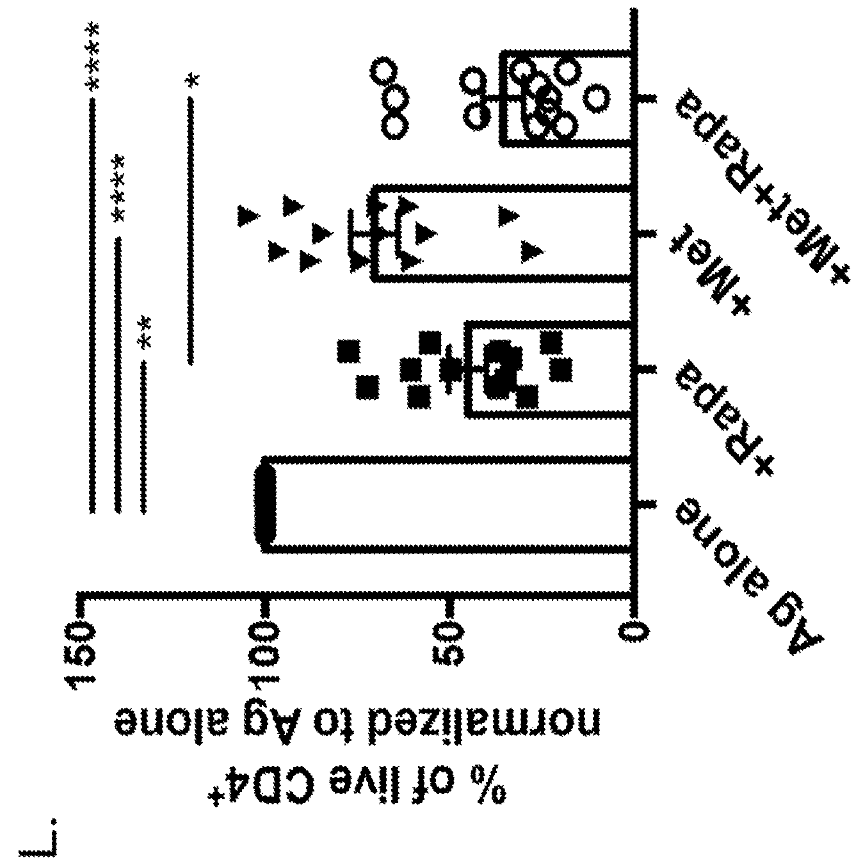
Figure 12K:
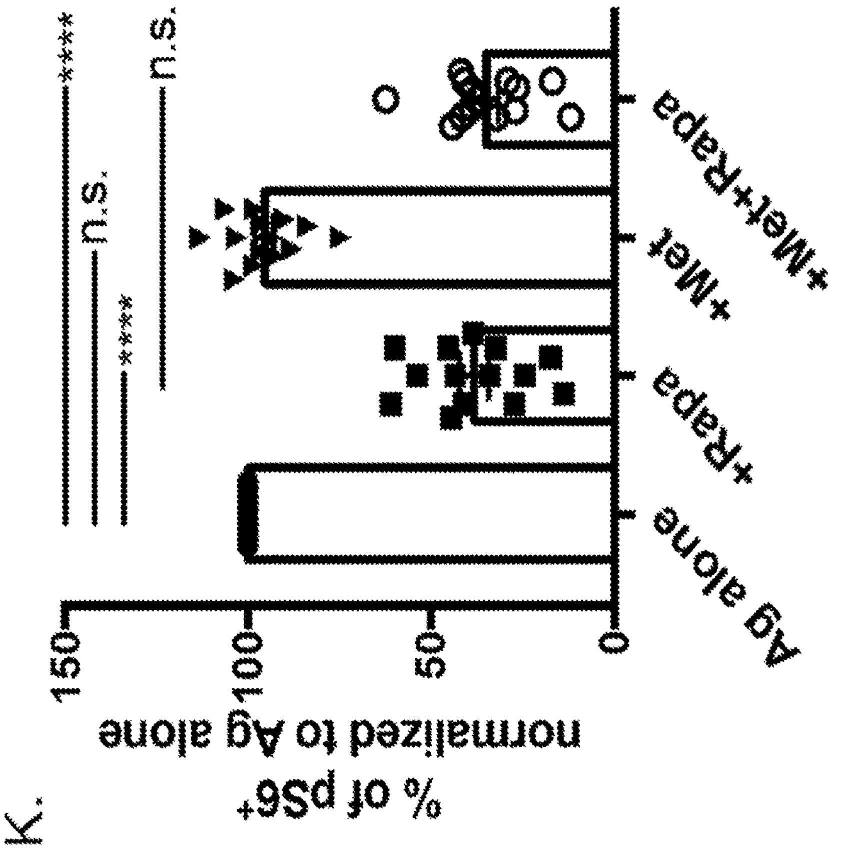
Figure 12M:
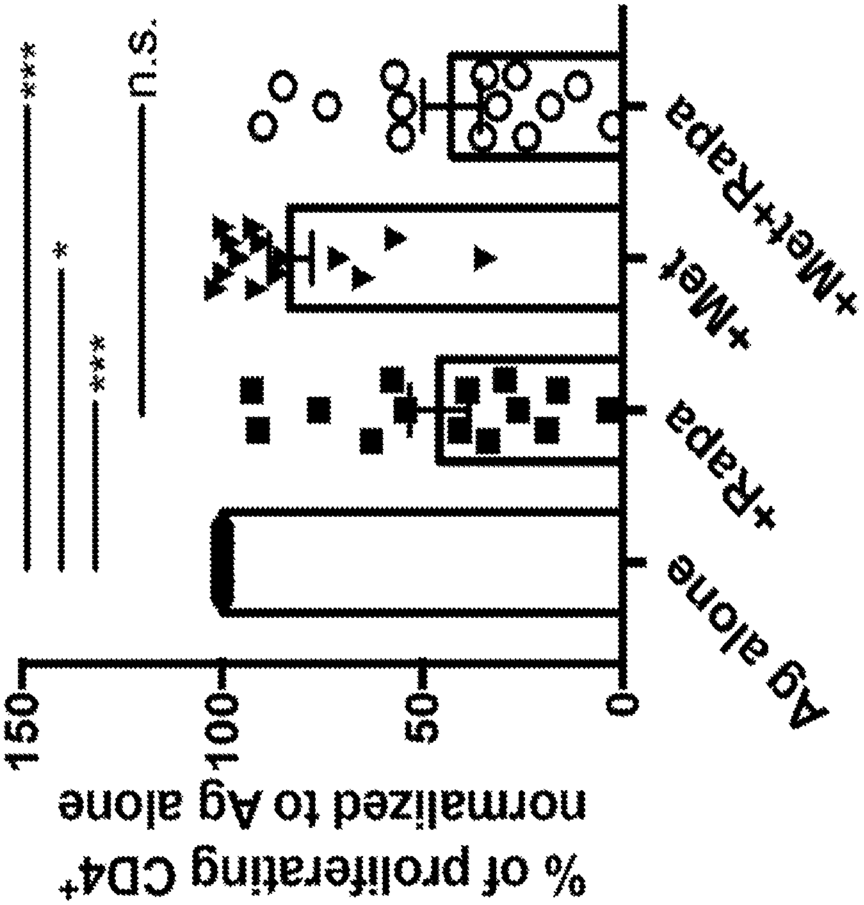
Figure 13:
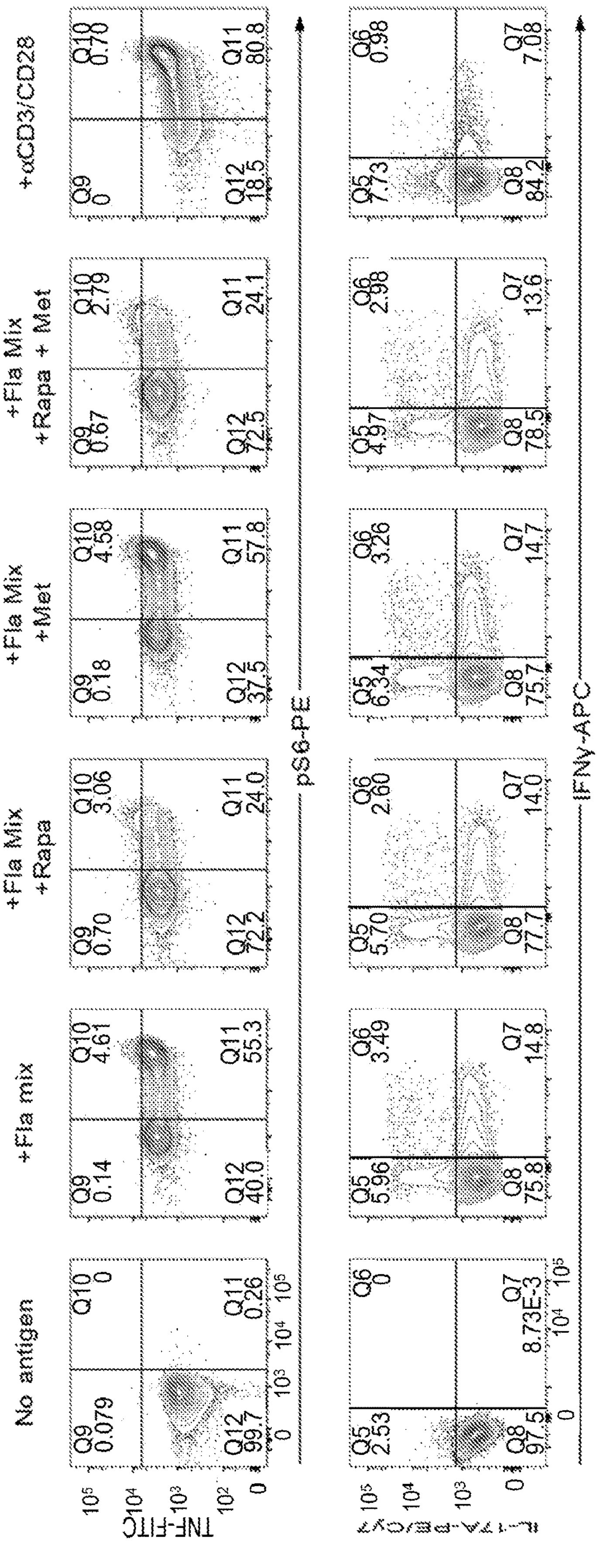
FIG. 13 shows that rapamycin has no effect on microbiota flagellin-specific $CD4^+$ T cell cytokine production. Expanded $CD154^+$ antigen-specific $CD4^+$ T cells were re-stimulated with autologous APCs and Fla mix, Fla mix with rapamycin, Fla mix with metformin, or Fla mix with rapamycin and metformin for 6-7 hours, with BFA added for the last 4 hours. $CD4^+$ T cells stimulated with CD3/CD28 beads were used as a positive control, whereas cells with no antigen added were used as a negative control. The cells were then stained for cytokines (TNF and IL-17A), activation of mTOR via the downstream marker phospho-S6K and analyzed by flow cytometry.

Metabolic Checkpoint Inhibition Dampens the Survival and Proliferation of Circulating Microbiota Antigen-Specific $CD4^+$ T Cells Isolated from Crohn's Patients As shown in previous studies, patients with Crohn's disease have significantly elevated serum anti-microbiota flagellin IgG response compared to healthy people. Whether the circulating microbiota flagellin-specific $CD4^+$ T cells are also increased in Crohn's patients was contemplated. To test this hypothesis, peripheral blood mononuclear cells (PBMCs) obtained from patients with Crohn's disease and healthy controls were stimulated with pooled flagellin antigens including CBir1, 14-2 Fla1, A4 Fla3, and FlaX. Antigen-specific $CD4^+$ T cells were identified based on their up-regulation of CD154 and CD69 (FIGS. 12A and 12B), an assay established from the antigen-reactive T cell enrichment (ARTE) protocol. Consistent with our serologic data (FIG. 2), the frequencies of microbiota flagellin-specific $CD4^+$ T cells in PBMCs were significantly elevated in patients with high serum IgG antibody response against multiple flagellin antigens (reactive to >50% of Lachnospiraceae flagellin antigens tested), but not in patients with low anti-flagellin serum IgG or healthy donors (FIG. 12C). Also, flagellin-specific $CD154^+$ cells isolated from Crohn's patients had significantly higher expression of effector cytokine IFNγ post 7 hr stimulation (FIGS. 12D and 12E). With magnetic bead labeling, these cells were enriched from ~0.5% to ~30% out of the total $CD4^+$ population (FIG. 12B) and further sort them with flow cytometry for ex vivo expansion with IL-2 and IL-7. Different from a previous study, the percentage of memory cells ($CD45RO^+$) in flagellin-specific $CD4^+$ T cells freshly post sorting ranged widely from less than 20% to over 80% in different patients, similar to the level of the memory subset in total $CD4^+$ cells without antigen stimulation (FIGS. 12F and 12G). Therefore, in order to target the metabolism of both naïve and memory CD4$^+$ subsets, rapamycin, metformin, or both, were tested for their inhibitory effects on these cells post expansion. Similar to the murine data, rapamycin treatment upon re-stimulation with pooled flagellin greatly inhibited the phosphorylation of ribosomal protein S6 kinase to ~50% reduction compared to antigen alone (FIGS. 12H and 12K), leading to significantly increased cell death (FIGS. 12I and 12L) and decreased cell proliferation (FIGS. 12J and 12M). Metformin treatment alone had no inhibitory effect on the mTOR pathway and resulted in a lesser extent of increased cell death and decreased proliferation. Although a synergetic inhibitory effect of rapamycin and metformin on cell proliferation was not observed, the survival of flagellin-specific CD4+ T cells post re-stimulation was significantly lower than either of the drugs when applied alone. Of note, neither rapamycin or metformin treatment altered the cytokine production, such as IFNγ, TNFα and IL-17A, in microbiota flagellin-specific CD4+ T cells upon re-stimulation (FIG. 13).

Figure 14:
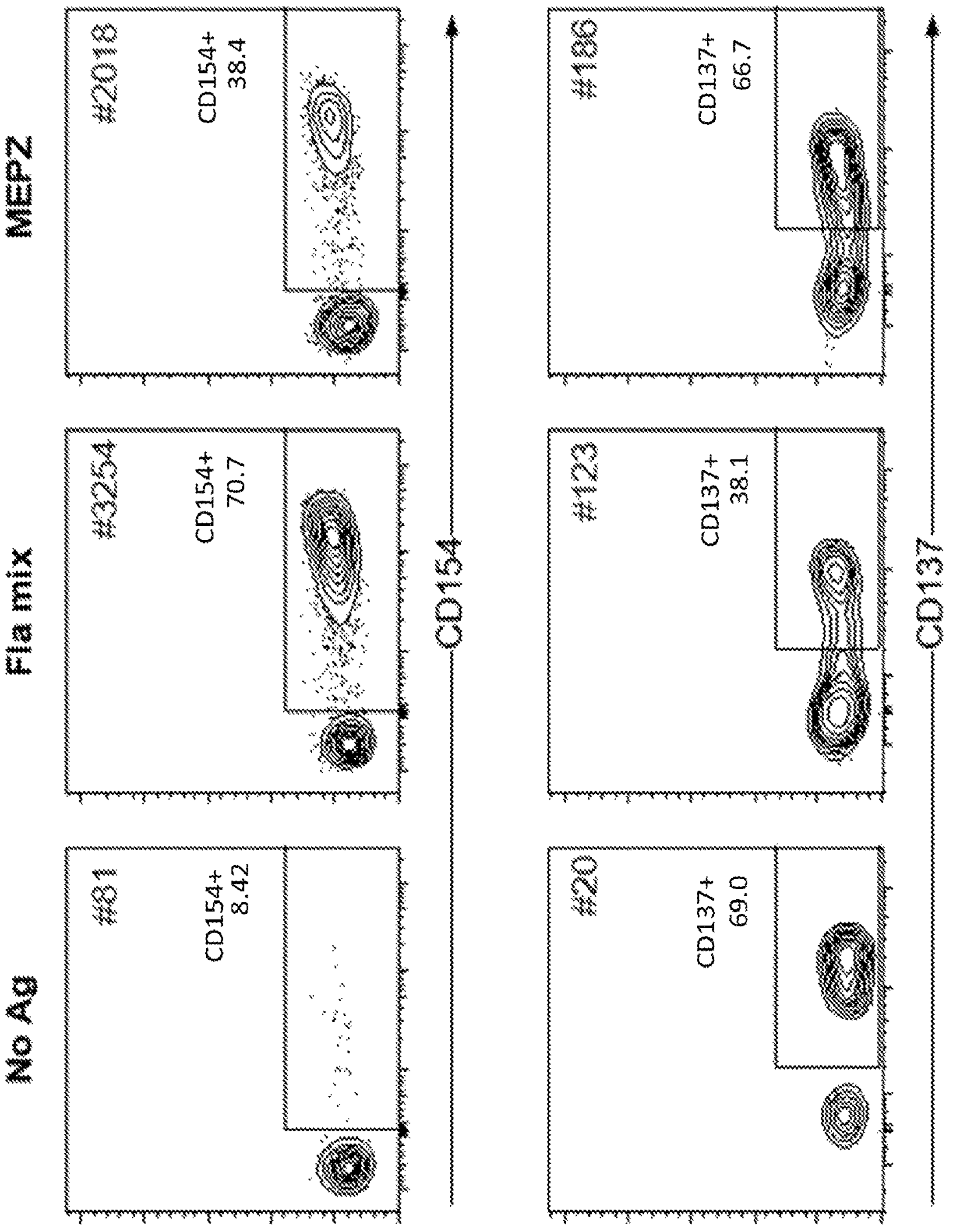
FIG. 14 shows a Crohn's patient/s CD4 T cell response to a flagellin multiepitope peptide (MEP1, also referred to as MEPZ) compared to a mixture of the recombinant flagellin proteins. The multiepitope peptide stimulated both Tconv (CD154+) and Treg (CD137+) CD4+ T cells that are reactive to microbiota flagellin. Numbers in the upper right hand corner of each panel show absolute numbers of cells that are reactive to different stimulations.

FIG. 14 shows a Crohn's patient CD4 T cell response to a flagellin multiepitope peptide (MEP1) compared to a mixture of the recombinant flagellin proteins. The multi-epitope peptide (MEP1) stimulated both Tconv (CD154+) and Treg (CD137+) CD4+ T cells that are reactive to microbiota flagellin. Numbers in the upper right hand corner of each panel show absolute numbers of cells that are reactive to different stimulations.

Preventive Immunotherapy

In some examples, the methods provided herein can be used to prevent inflammatory bowel disease, for example, Crohn's disease. For example, flagellin peptide(s) (for example, the multi-epitope peptide described herein) can be administered to a patient in remission, for example, surgery or medically induced remission. The peptide(s) can be administered to the patient intradermally or subcutaneously and an mTOR inhibitor, for example, rapamycin can be administered orally for 5 days. This administration schedule can be repeated, for example, at 2, 4, 6 or 12 month intervals.

In summary, these studies show showed that metabolic inhibition during cell activation (MIdCA) by targeting key metabolic regulators mTORC and AMPK resulted in CD4$^+$ naïve and memory T cell death and anergy, but enhanced the induction of CD4$^+$ regulatory T (Treg) cells. This metabolic inhibition treatment successfully prevented the development of intestinal inflammation in the CBir1 TCR Tg CD4$^+$ T cell transfer colitis model. Microbiota-specific CD4$^+$ T cells, especially the pathogenic $T_E$ subsets, were decreased 10 fold in the intestinal lamina propria. Furthermore, the MIdCA strategy was able to prevent antigen-specific $T_M$ cell formation upon initial antigen encounter, and ablate existing $T_M$ cells upon re-activation in mice. Human microbiota flagellin-specific CD4$^+$ T cells isolated from Crohn's patients, treated with MIdCA, were ablated in a similar manner with half of the antigen-specific T cells undergoing apoptosis. These results indicate that metabolic inhibition of activated microbiota-specific CD4$^+$ T cells is an effective way to eliminate pathogenic CD4$^+$ $T_M$ cells and to induce Treg cells that provide antigen-specific and bystander suppression, serving as an immunotherapy for inflammatory bowel disease.

What is claimed is:

1. A method for treating or preventing inflammatory bowel disease comprising administering to a subject having inflammatory bowel disease or at risk of developing inflammatory bowel disease a) an effective amount of a multi-epitope polypeptide comprising two or more flagellin T-cell receptor (TCR) epitopes selected from the group consisting of SEQ ID NO: 6, SEQ ID NO: 7 SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO; 27, SEQ ID NO: 34, SEQ ID NO: 35, SEQ ID NO: 36, and SEQ ID NO: 37; and b) an effective amount of an agent that reduces flagellin antigen-specific memory T cells and/or increases regulatory T cells in the subject.

2. A method for delaying or reducing the intensity of a relapse or flare of an inflammatory bowel disease in a subject comprising administering to a subject a) an effective amount of a polypeptide comprising two or more flagellin T-cell receptor (TCR) epitopes selected from the group consisting of SEQ ID NO: 6, SEQ ID NO: 7 SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO; 27, SEQ ID NO: 34, SEQ ID NO: 35, SEQ ID NO: 36, and SEQ ID NO: 37; and b) an effective amount of an agent that increases regulatory T cells in the subject.

3. The method of claim 1, wherein the agent that reduces flagellin antigen-specific memory T cells and/or increases regulatory T cells in the subject is selected from the group consisting of a mutant IL-2 polypeptide selected from the group consisting of SEQ ID NO: 29 and SEQ ID NO: 30, a metabolic inhibitor and a combination thereof.

4. The method of claim 1, wherein the inflammatory bowel disease is Crohn's disease or ulcerative colitis.

5. The method of claim 1, wherein the two or more TCR epitopes activate flagellin-specific $CD4^+$ T cells.

6. The method of claim 3, wherein the metabolic inhibitor inactivates flagellin-specific activated T cells.

7. The method of claim 3, wherein the metabolic inhibitor is an FK506-binding protein 12-rapamycin-associated protein 1 (mTOR) inhibitor.

8. The method of claim 7, wherein the mTOR inhibitor is rapamycin.

9. The method of claim 1, further comprising administering a protein kinase AMP-activated catalytic subunit alpha 1 (AMPK) activator to the subject.

10. The method of claim 9, wherein the AMPK activator is metformin.

11. The method of claim 1, wherein an increase in Treg cells and/or a decrease in memory ($T_M$) cells occurs in the subject.

12. The method of claim 1, wherein the subject has an increased anti-flagellin response as compared to a control.

13. The method of claim 1, wherein the polypeptide comprises two or more T-cell receptor (TCR) epitopes selected from the group consisting of SEQ ID NO: 6 (MVVQHNMQAMNANRMLNVTT), SEQ ID NO: 7 (LTEVHSMLQRMNELAVQASNG), SEQ ID NO: 8 (MVVQHNMTAANANRM), and SEQ ID NO: 9 (GETHSILQRMNELATQAAN).

14. The method of claim 13, wherein the polypeptide comprises the amino acid sequences of SEQ ID NO: 5.

* * * * *

SEQUENCE LISTING

```
<160> NUMBER OF SEQ ID NOS: 38

<210> SEQ ID NO 1
<211> LENGTH: 20
<212> TYPE: PRT
<213> ORGANISM: Artificial sequence
<220> FEATURE:
<223> OTHER INFORMATION: Synthetic construct

<400> SEQUENCE: 1

Asp Met Ala Thr Glu Met Val Lys Tyr Ser Asn Ala Asn Ile Leu Ser
1               5                   10                  15

Gln Ala Gly Gln
            20


<210> SEQ ID NO 2
<211> LENGTH: 17
<212> TYPE: PRT
<213> ORGANISM: Artificial sequence
<220> FEATURE:
<223> OTHER INFORMATION: Synthetic construct

<400> SEQUENCE: 2

Ile Ser Gln Ala Val His Ala Ala His Ala Glu Ile Asn Glu Ala Gly
1               5                   10                  15

Arg


<210> SEQ ID NO 3
<211> LENGTH: 14
<212> TYPE: PRT
<213> ORGANISM: Artificial sequence
<220> FEATURE:
<223> OTHER INFORMATION: Synthetic construct
```

-continued

<400> SEQUENCE: 3

Glu Ala Trp Gly Ala Leu Ala Asn Trp Ala Val Asp Ser Ala
1 5 10

<210> SEQ ID NO 4
<211> LENGTH: 162
<212> TYPE: PRT
<213> ORGANISM: Artificial sequence
<220> FEATURE:
<223> OTHER INFORMATION: Synthetic construct

<400> SEQUENCE: 4

Met Arg Gly Ser His His His His His His Gly Ser Met Arg Lys Gln
1 5 10 15

Ile Arg Gly Leu Thr Gln Ala Ser Thr Asn Ala Glu Asp Gly Ile Ser
20 25 30

Ser Val Gln Thr Ala Glu Gly Ala Leu Thr Glu Val His Asp Met Leu
35 40 45

Gln Arg Met Asn Glu Leu Ala Ile Gln Ala Ala Asn Gly Thr Asp Met
50 55 60

Ala Thr Glu Met Val Lys Tyr Ser Asn Ala Asn Ile Leu Ser Gln Ala
65 70 75 80

Gly Gln Asp Met Ala Thr Glu Met Val Lys Tyr Ser Asn Ala Asn Ile
85 90 95

Leu Ser Gln Ala Gly Gln Asp Met Ala Thr Glu Met Val Lys Tyr Ser
100 105 110

Asn Ala Asn Ile Leu Ser Gln Ala Gly Gln Ile Ser Gln Ala Val His
115 120 125

Ala Ala His Ala Glu Ile Asn Glu Ala Gly Arg Glu Ala Trp Gly Ala
130 135 140

Leu Ala Asn Trp Ala Val Asp Ser Ala Arg Gly Ser His His His His
145 150 155 160

His His

<210> SEQ ID NO 5
<211> LENGTH: 471
<212> TYPE: PRT
<213> ORGANISM: Artificial sequence
<220> FEATURE:
<223> OTHER INFORMATION: Synthetic construct

<400> SEQUENCE: 5

Met Val Val Gln His Asn Met Gln Ala Met Asn Ala Asn Arg Met Leu
1 5 10 15

Asn Val Thr Thr Leu Thr Glu Val His Ser Met Leu Gln Arg Met Asn
20 25 30

Glu Leu Ala Val Gln Ala Ser Asn Gly Met Val Val Gln His Asn Met
35 40 45

Thr Ala Ala Asn Ala Asn Arg Met Gly Glu Thr His Ser Ile Leu Gln
50 55 60

Arg Met Asn Glu Leu Ala Thr Gln Ala Ala Asn Met Val Val Gln His
65 70 75 80

Asn Leu Thr Ala Met Asn Ala Asn Arg Gln Leu Val Gly Thr Thr Gly
85 90 95

Met Val Val Gln His Asn Met Gln Ala Ala Asn Ala Asn Arg Met Leu
100 105 110

Gly Ile Thr Ser Val His Ser Met Leu Gln Arg Met Asn Glu Leu Ala

-continued

```
        115                 120                 125

Val Gln Ala Ala Ser Asn Gly Thr Asn Ser Met Val Val Gln His Asn
    130                 135                 140

Met Gln Ala Ala Asn Ala Asn Arg Met Leu Asn Val Thr Thr Leu Thr
145                 150                 155                 160

Glu Val His Ser Met Leu Gln Arg Met Asn Glu Leu Ala Thr Gln Ser
                165                 170                 175

Ala Asn Gly Leu Thr Glu Val His Ser Met Leu Gln Arg Met Asn Glu
            180                 185                 190

Leu Ala Val Gln Ser Ser Asn Gly Asp Met Ala Glu Glu Met Val Glu
        195                 200                 205

Tyr Ser Lys Asn Asn Ile Leu Ala Gln Ala Gly Gln Ser Met Leu Ala
    210                 215                 220

Gln Ala Asn Gln Ser Met Ala Glu Glu Met Val Asn Tyr Ser Lys Asn
225                 230                 235                 240

Asn Ile Leu Ala Ala Gln Ala Gly Gln Ser Met Leu Ala Gln Ala Asn
                245                 250                 255

Gln Met Ala Lys Glu Met Val Asn Tyr Ser Lys Asn Asn Ile Leu Ala
            260                 265                 270

Gln Ala Gly Gln Ser Met Leu Ala Gln Ala Asn Asp Met Ala Glu Glu
        275                 280                 285

Met Val Thr Tyr Ser Lys Asn Asn Ile Leu Ala Gln Ala Gly Gln Ser
    290                 295                 300

Met Leu Ala Gln Ala Asn Gln Met Val Val Gln His Asn Leu Arg Ala
305                 310                 315                 320

Met Asn Ser Asn Arg Met Leu Gly Ile Thr Gln Ser Ala Gln Arg Ser
                325                 330                 335

Leu Leu Gly Ala Val Gln Asn Arg Leu Glu His Thr Ile Asn Asn Asn
            340                 345                 350

Glu Ala His Ser Ile Leu Gln Arg Met Asn Glu Leu Ala Val Gln Gly
        355                 360                 365

Ala Asn Asp Val Glu Tyr Ser Lys Asn Asn Ile Leu Ala Gln Ala Gly
    370                 375                 380

Gln Ser Met Leu Ala Gln Ala Asn Gln Met Val Val Gln His Asn Leu
385                 390                 395                 400

Arg Ala Met Asn Ser Asn Arg Met Leu Ser Ile Thr Gln Asp Met Ala
                405                 410                 415

Thr Glu Met Val Lys Phe Ser Asn Ser Asn Ile Leu Ala Gln Ala Gly
            420                 425                 430

Gln Met Val Val Gln His Asn Leu Arg Ala Met Asn Ala Asn Arg Met
        435                 440                 445

Leu Gly Ile Thr Thr Glu Val His Asp Met Leu Gln Arg Met Asn Glu
    450                 455                 460

Leu Ala Val Lys Ala Ala Asn
465                 470


<210> SEQ ID NO 6
<211> LENGTH: 20
<212> TYPE: PRT
<213> ORGANISM: Artificial sequence
<220> FEATURE:
<223> OTHER INFORMATION: Synthetic construct

<400> SEQUENCE: 6

Met Val Val Gln His Asn Met Gln Ala Met Asn Ala Asn Arg Met Leu
```

-continued 1 5 10 15

Asn Val Thr Thr
20

<210> SEQ ID NO 7
<211> LENGTH: 21
<212> TYPE: PRT
<213> ORGANISM: Artificial sequence
<220> FEATURE:
<223> OTHER INFORMATION: Synthetic construct

<400> SEQUENCE: 7

Leu Thr Glu Val His Ser Met Leu Gln Arg Met Asn Glu Leu Ala Val
1 5 10 15

Gln Ala Ser Asn Gly
20

<210> SEQ ID NO 8
<211> LENGTH: 15
<212> TYPE: PRT
<213> ORGANISM: Artificial sequence
<220> FEATURE:
<223> OTHER INFORMATION: Synthetic construct

<400> SEQUENCE: 8

Met Val Val Gln His Asn Met Thr Ala Ala Asn Ala Asn Arg Met
1 5 10 15

<210> SEQ ID NO 9
<211> LENGTH: 19
<212> TYPE: PRT
<213> ORGANISM: Artificial sequence
<220> FEATURE:
<223> OTHER INFORMATION: Synthetic construct

<400> SEQUENCE: 9

Gly Glu Thr His Ser Ile Leu Gln Arg Met Asn Glu Leu Ala Thr Gln
1 5 10 15

Ala Ala Asn

<210> SEQ ID NO 10
<211> LENGTH: 21
<212> TYPE: PRT
<213> ORGANISM: Artificial sequence
<220> FEATURE:
<223> OTHER INFORMATION: Synthetic construct

<400> SEQUENCE: 10

Met Val Val Gln His Asn Leu Thr Ala Met Asn Ala Asn Arg Gln Leu
1 5 10 15

Val Gly Thr Thr Gly
20

<210> SEQ ID NO 11
<211> LENGTH: 20
<212> TYPE: PRT
<213> ORGANISM: Artificial sequence
<220> FEATURE:
<223> OTHER INFORMATION: Synthetic construct

<400> SEQUENCE: 11

Met Val Val Gln His Asn Met Gln Ala Ala Asn Ala Asn Arg Met Leu
1 5 10 15

Asn Val Thr Thr

20

<210> SEQ ID NO 12
<211> LENGTH: 21
<212> TYPE: PRT
<213> ORGANISM: Artificial sequence
<220> FEATURE:
<223> OTHER INFORMATION: Synthetic construct

<400> SEQUENCE: 12

```
Leu Thr Glu Val His Ser Met Leu Gln Arg Met Asn Glu Leu Ala Thr
1               5                   10                  15

Gln Ser Ala Asn Gly
            20
```

<210> SEQ ID NO 13
<211> LENGTH: 21
<212> TYPE: PRT
<213> ORGANISM: Artificial sequence
<220> FEATURE:
<223> OTHER INFORMATION: Synthetic construct

<400> SEQUENCE: 13

```
Leu Thr Glu Val His Ser Met Leu Gln Arg Met Asn Glu Leu Ala Val
1               5                   10                  15

Gln Ser Ser Asn Gly
            20
```

<210> SEQ ID NO 14
<211> LENGTH: 29
<212> TYPE: PRT
<213> ORGANISM: Artificial sequence
<220> FEATURE:
<223> OTHER INFORMATION: Synthetic construct

<400> SEQUENCE: 14

```
Asp Met Ala Glu Glu Met Val Glu Tyr Ser Lys Asn Asn Ile Leu Ala
1               5                   10                  15

Gln Ala Gly Gln Ser Met Leu Ala Gln Ala Asn Gln Ser
            20                  25
```

<210> SEQ ID NO 15
<211> LENGTH: 28
<212> TYPE: PRT
<213> ORGANISM: Artificial sequence
<220> FEATURE:
<223> OTHER INFORMATION: Synthetic construct

<400> SEQUENCE: 15

```
Met Ala Glu Glu Met Val Asn Tyr Ser Lys Asn Asn Ile Leu Ala Ala
1               5                   10                  15

Gln Ala Gly Gln Ser Met Leu Ala Gln Ala Asn Gln
            20                  25
```

<210> SEQ ID NO 16
<211> LENGTH: 26
<212> TYPE: PRT
<213> ORGANISM: Artificial sequence
<220> FEATURE:
<223> OTHER INFORMATION: synthetic construct

<400> SEQUENCE: 16

```
Met Ala Lys Glu Met Val Asn Tyr Ser Lys Asn Asn Ile Leu Ala Gln
1               5                   10                  15
```

-continued

Ala Gly Gln Ser Met Leu Ala Gln Ala Asn
20 25

<210> SEQ ID NO 17
<211> LENGTH: 28
<212> TYPE: PRT
<213> ORGANISM: Artificial sequence
<220> FEATURE:
<223> OTHER INFORMATION: synthetic construct

<400> SEQUENCE: 17

Asp Met Ala Glu Glu Met Val Thr Tyr Ser Lys Asn Asn Ile Leu Ala
1 5 10 15

Gln Ala Gly Gln Ser Met Leu Ala Gln Ala Asn Gln
20 25

<210> SEQ ID NO 18
<211> LENGTH: 20
<212> TYPE: PRT
<213> ORGANISM: Artificial sequence
<220> FEATURE:
<223> OTHER INFORMATION: Synthetic construct

<400> SEQUENCE: 18

Met Val Val Gln His Asn Leu Arg Ala Met Asn Ser Asn Arg Met Leu
1 5 10 15

Gly Ile Thr Gln
20

<210> SEQ ID NO 19
<211> LENGTH: 20
<212> TYPE: PRT
<213> ORGANISM: Artificial sequence
<220> FEATURE:
<223> OTHER INFORMATION: Synthetic construct

<400> SEQUENCE: 19

Ser Ala Gln Arg Ser Leu Leu Gly Ala Val Gln Asn Arg Leu Glu His
1 5 10 15

Thr Ile Asn Asn
20

<210> SEQ ID NO 20
<211> LENGTH: 20
<212> TYPE: PRT
<213> ORGANISM: Artificial sequence
<220> FEATURE:
<223> OTHER INFORMATION: Synthetic construct

<400> SEQUENCE: 20

Asn Glu Ala His Ser Ile Leu Gln Arg Met Asn Glu Leu Ala Val Gln
1 5 10 15

Gly Ala Asn Asp
20

<210> SEQ ID NO 21
<211> LENGTH: 21
<212> TYPE: PRT
<213> ORGANISM: Artificial sequence
<220> FEATURE:
<223> OTHER INFORMATION: Synthetic construct

<400> SEQUENCE: 21

Val Glu Tyr Ser Lys Asn Asn Ile Leu Ala Gln Ala Gly Gln Met Leu
1 5 10 15

```
Ala Gln Ala Asn Gln
            20


<210> SEQ ID NO 22
<211> LENGTH: 20
<212> TYPE: PRT
<213> ORGANISM: Artificial sequence
<220> FEATURE:
<223> OTHER INFORMATION: Synthetic construct

<400> SEQUENCE: 22

Met Val Val Gln His Asn Leu Arg Ala Met Asn Ser Asn Arg Met Leu
1               5                   10                  15

Ser Ile Thr Gln
            20


<210> SEQ ID NO 23
<211> LENGTH: 20
<212> TYPE: PRT
<213> ORGANISM: Artificial sequence
<220> FEATURE:
<223> OTHER INFORMATION: Synthetic construct

<400> SEQUENCE: 23

Asp Met Ala Thr Glu Met Val Lys Phe Ser Asn Ser Asn Ile Leu Ala
1               5                   10                  15

Gln Ala Gly Gln
            20


<210> SEQ ID NO 24
<211> LENGTH: 19
<212> TYPE: PRT
<213> ORGANISM: Artificial sequence
<220> FEATURE:
<223> OTHER INFORMATION: Synthetic construct

<400> SEQUENCE: 24

Met Val Val Gln His Asn Leu Arg Ala Met Asn Ala Asn Arg Met Leu
1               5                   10                  15

Gly Ile Thr


<210> SEQ ID NO 25
<211> LENGTH: 19
<212> TYPE: PRT
<213> ORGANISM: Artificial sequence
<220> FEATURE:
<223> OTHER INFORMATION: Synthetic construct

<400> SEQUENCE: 25

Thr Glu Val His Asp Met Leu Gln Arg Met Asn Glu Leu Ala Val Lys
1               5                   10                  15

Ala Ala Asn


<210> SEQ ID NO 26
<211> LENGTH: 20
<212> TYPE: PRT
<213> ORGANISM: Artificial sequence
<220> FEATURE:
<223> OTHER INFORMATION: Synthetic construct

<400> SEQUENCE: 26

Met Lys Val Lys Val Leu Ser Leu Leu Val Pro Ala Leu Leu Val Ala
1               5                   10                  15
```

-continued

```
Gly Ala Ala Asn
            20


<210> SEQ ID NO 27
<211> LENGTH: 20
<212> TYPE: PRT
<213> ORGANISM: Artificial sequence
<220> FEATURE:
<223> OTHER INFORMATION: Synthetic construct

<400> SEQUENCE: 27

Val Asp Val Gly Ala Thr Tyr Tyr Phe Asn Lys Asn Met Ser Thr Tyr
1               5                   10                  15

Val Asp Tyr Lys
            20


<210> SEQ ID NO 28
<211> LENGTH: 36
<212> TYPE: PRT
<213> ORGANISM: Artificial sequence
<220> FEATURE:
<223> OTHER INFORMATION: Synthetic construct

<400> SEQUENCE: 28

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

His Pro Phe Thr
        35


<210> SEQ ID NO 29
<211> LENGTH: 133
<212> TYPE: PRT
<213> ORGANISM: Artificial sequence
<220> FEATURE:
<223> OTHER INFORMATION: Synthetic construct

<400> SEQUENCE: 29

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Ala Leu Asn Leu Ala Pro Ser Lys Asn Phe His Ile
65                  70                  75                  80

Arg Pro Arg Asp Leu Ile Ser Asp Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130


<210> SEQ ID NO 30
<211> LENGTH: 133
<212> TYPE: PRT
```

<213> ORGANISM: Artificial sequence
<220> FEATURE:
<223> OTHER INFORMATION: Synthetic construct

<400> SEQUENCE: 30

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Ala Leu Asn Leu Ala Pro Ser Lys Asn Phe His Leu
65                  70                  75                  80

Arg Pro Arg Asp Leu Ile Ser Asp Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Ile Asn Arg Trp Ile Thr Phe Ser Gln Ser Ile
        115                 120                 125

Ile Ser Thr Leu Thr
    130
```

<210> SEQ ID NO 31
<211> LENGTH: 8
<212> TYPE: PRT
<213> ORGANISM: Artificial sequence
<220> FEATURE:
<223> OTHER INFORMATION: Synthetic construct

<400> SEQUENCE: 31

```
Asp Tyr Lys Asp Asp Asp Asp Lys
1               5
```

<210> SEQ ID NO 32
<211> LENGTH: 6
<212> TYPE: PRT
<213> ORGANISM: Artificial sequence
<220> FEATURE:
<223> OTHER INFORMATION: Synthetic construct

<400> SEQUENCE: 32

```
His His His His His His
1               5
```

<210> SEQ ID NO 33
<211> LENGTH: 9
<212> TYPE: PRT
<213> ORGANISM: Artificial sequence
<220> FEATURE:
<223> OTHER INFORMATION: Synthetic construct

<400> SEQUENCE: 33

```
Tyr Pro Tyr Asp Val Pro Asp Tyr Ala
1               5
```

<210> SEQ ID NO 34
<211> LENGTH: 17
<212> TYPE: PRT
<213> ORGANISM: Artificial sequence
<220> FEATURE:
<223> OTHER INFORMATION: Synthetic construct

<400> SEQUENCE: 34

Met Val Val Gln His Asn Leu Gln Ala Met Asn Ser Asn Arg Met Leu
1 5 10 15

Gly

<210> SEQ ID NO 35
<211> LENGTH: 16
<212> TYPE: PRT
<213> ORGANISM: Artificial sequence
<220> FEATURE:
<223> OTHER INFORMATION: Synthetic construct

<400> SEQUENCE: 35

Ala Gly Ala Ile Lys Lys Val Ser Thr Gln Arg Ser Ala Leu Gly Ala
1 5 10 15

<210> SEQ ID NO 36
<211> LENGTH: 19
<212> TYPE: PRT
<213> ORGANISM: Artificial sequence
<220> FEATURE:
<223> OTHER INFORMATION: Synthetic construct

<400> SEQUENCE: 36

Met Ala Thr Glu Met Val Lys Tyr Ser Asn Ala Asn Ile Leu Ser Gln
1 5 10 15

Ala Gly Gln

<210> SEQ ID NO 37
<211> LENGTH: 20
<212> TYPE: PRT
<213> ORGANISM: Artificial sequence
<220> FEATURE:
<223> OTHER INFORMATION: Synthetic construct

<400> SEQUENCE: 37

Met Val Val Gln His Asn Met Gln Ala Ala Asn Ala Asn Arg Met Leu
1 5 10 15

Gly Ile Thr Ser
20

<210> SEQ ID NO 38
<211> LENGTH: 22
<212> TYPE: PRT
<213> ORGANISM: Artificial sequence
<220> FEATURE:
<223> OTHER INFORMATION: Synthetic construct

<400> SEQUENCE: 38

Val His Ser Met Leu Gln Arg Met Asn Glu Leu Ala Val Gln Ala Ala Ser
1 5 10 15

Asn Gly Thr Asn Ser
20